(12) United States Patent
Kriesel et al.

(10) Patent No.: US 6,174,300 B1
(45) Date of Patent: *Jan. 16, 2001

(54) FLUID DELIVERY DEVICE WITH TEMPERATURE CONTROLLED ENERGY SOURCE

(75) Inventors: Marshall S. Kriesel, St. Paul; Thomas N. Thompson, Richfield, both of MN (US)

(73) Assignee: Science Incorporated, Bloomington, MN (US)

(*) Notice: Under 35 U.S.C. 154(b), the term of this patent shall be extended for 0 days.

This patent is subject to a terminal disclaimer.

(21) Appl. No.: 09/387,447

(22) Filed: Sep. 1, 1999

Related U.S. Application Data

(62) Division of application No. 08/919,147, filed on Aug. 27, 1997, now Pat. No. 5,961,492.

(51) Int. Cl.[7] .................................................. A61M 37/00
(52) U.S. Cl. ................................... 604/132; 128/DIG. 12
(58) Field of Search ........................... 604/131, 132, 604/151, 153, 185, 257, 259, 262, 890.1, 67, 90; 128/DIG. 12, DIG. 1; 222/94–96

(56) References Cited

U.S. PATENT DOCUMENTS 5,961,492 * 10/1999 Kriesek et al. ..................... 604/132

* cited by examiner

Primary Examiner—A. T. Nguyen
(74) Attorney, Agent, or Firm—James E. Brunton

(57) ABSTRACT

A fluid delivery apparatus for infusing medicinal fluids into a patient which is of a compact, low profile, laminate construction. The apparatus embodies a novel thermal expanding polymer material which uniquely functions as an internal energy source for expelling the medicinal fluids from the device. The apparatus can be used for subdermal, intradermal and intramuscular infusion of fluids and in one form of the invention, includes a novel delivery cannula having a body portion disposed within a circuitous channel formed within the base superstructure of the apparatus and a pierceable portion which extends outwardly from the base of the apparatus. By constructing the cannula in a circuitous configuration and dynamically connecting it to the base assembly, movement of the cannula relative to the base assembly is permitted thereby minimizing needle related tissue necrosis. The heat-expandable mass which is heated by the patient's body temperature in a manner to controllably expel fluid from the device uniquely functions to provide a conformable ullage within the reservoir of the device which will effectively avoid extended flow delivery rate trail-off at the end of the fluid delivery period. Further, the heat expandable mass can be specifically tailored to provide precise, predictable protocol delivery of the medicinal agent stored within the reservoir of the device.

21 Claims, 34 Drawing Sheets

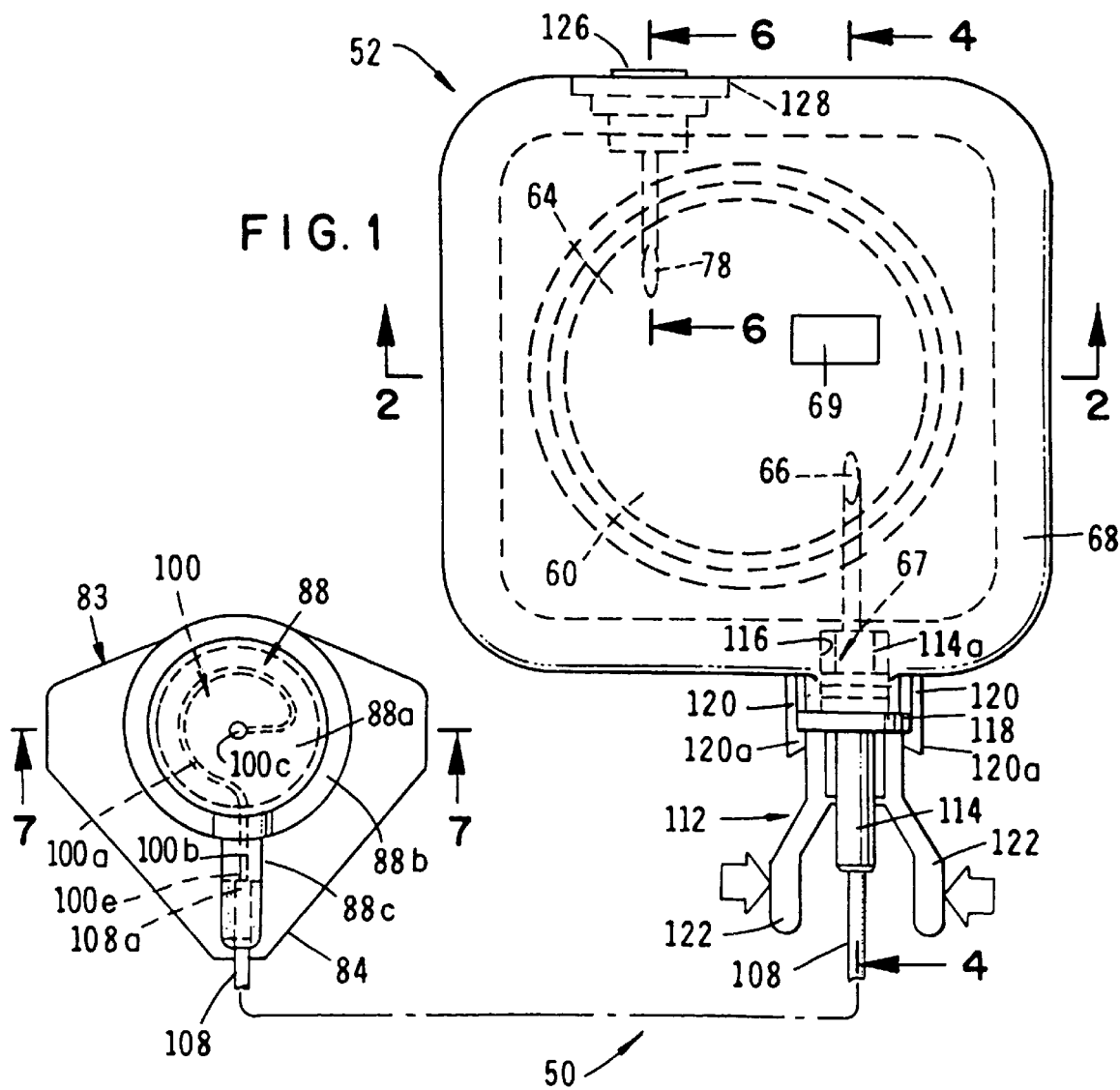
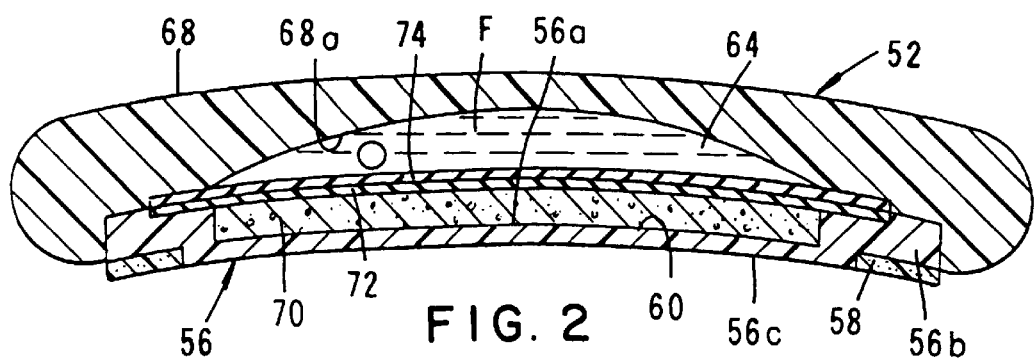

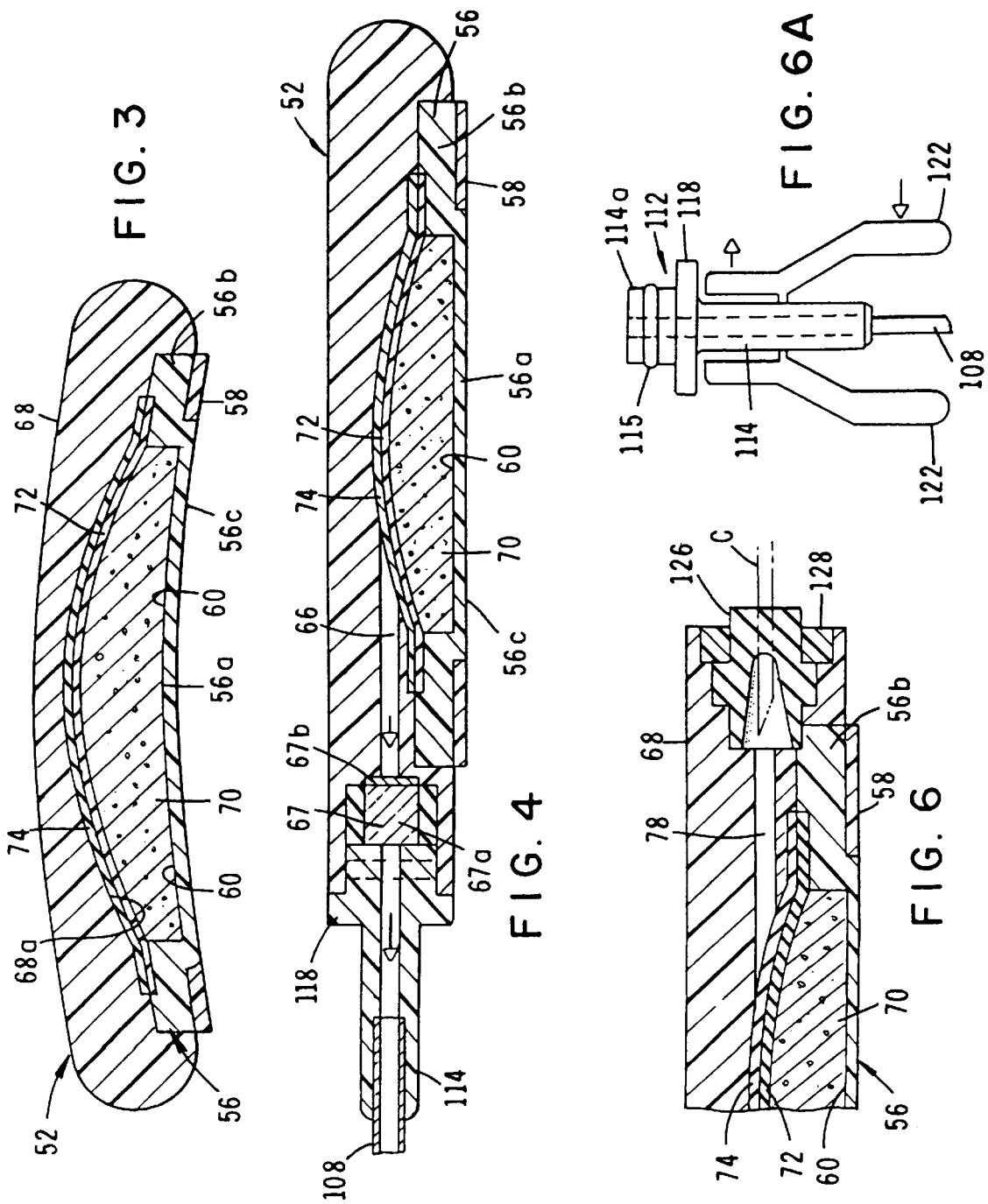

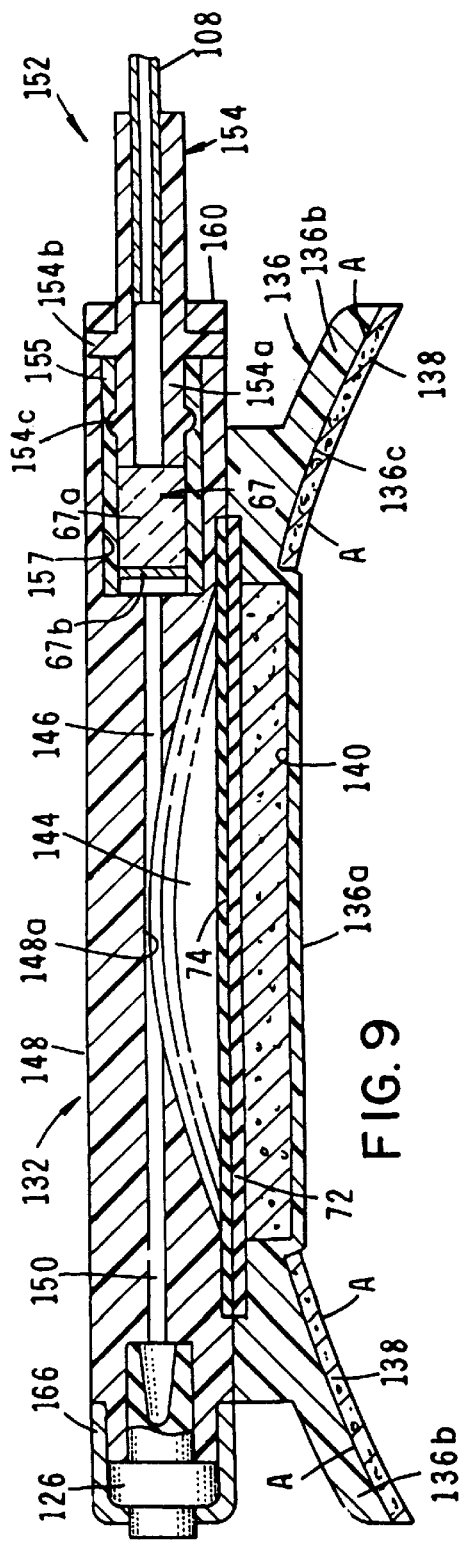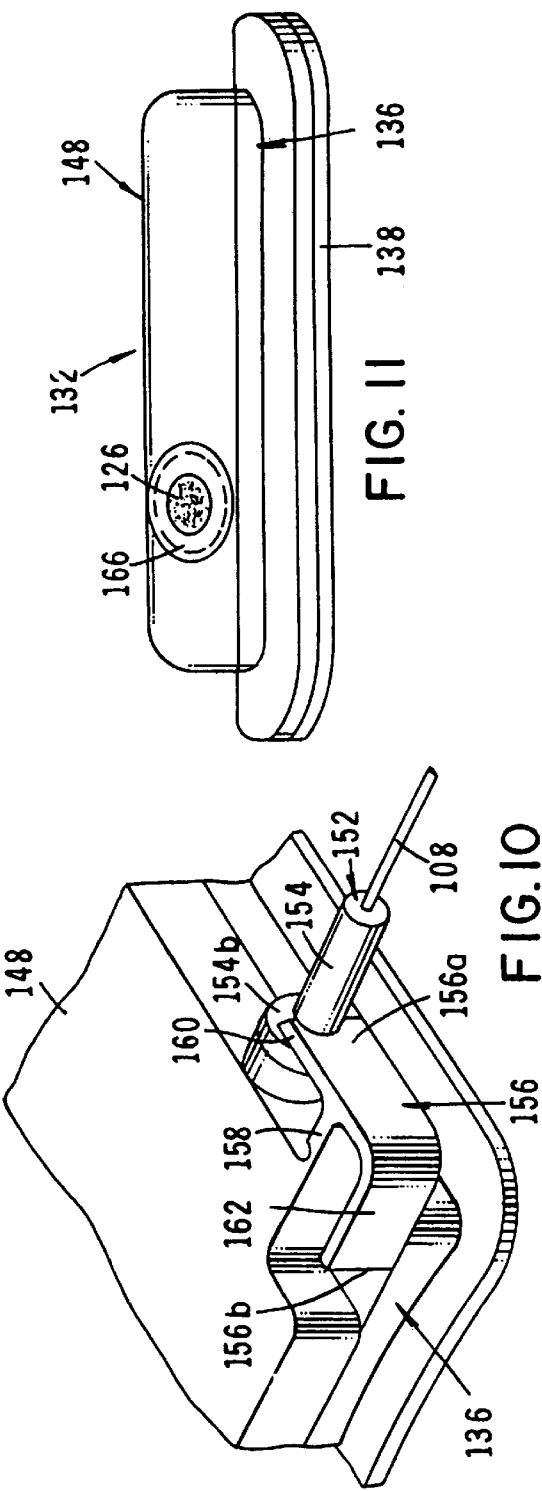

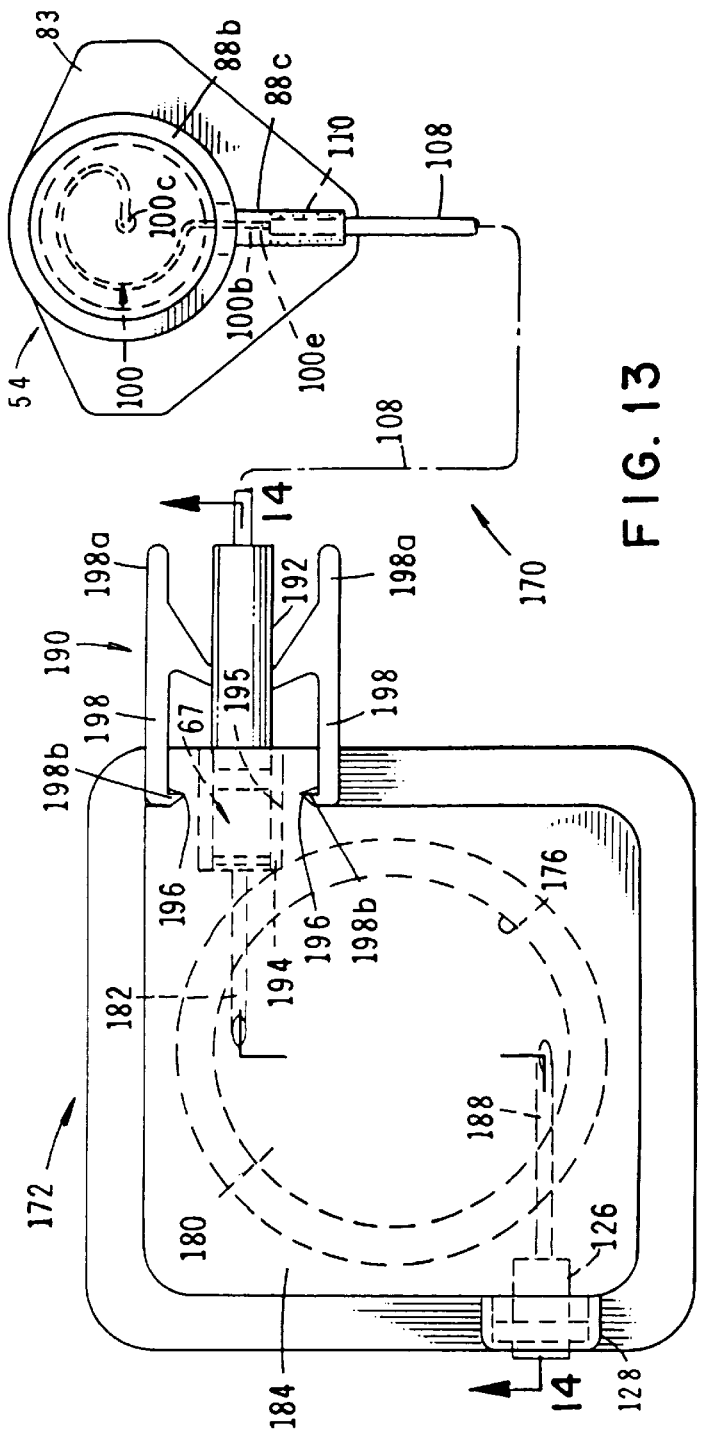
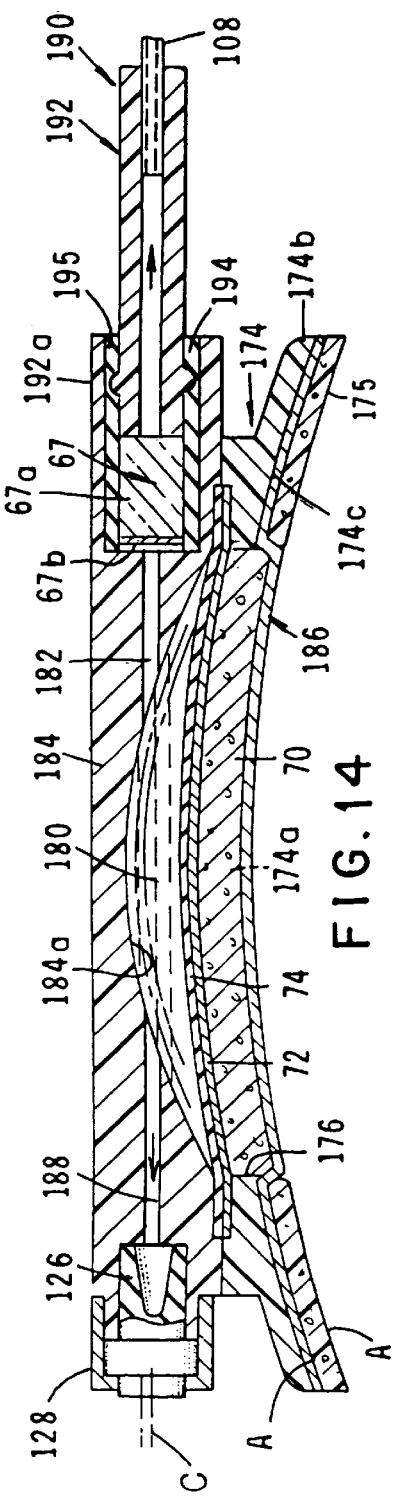
FIG. 13
FIG. 14

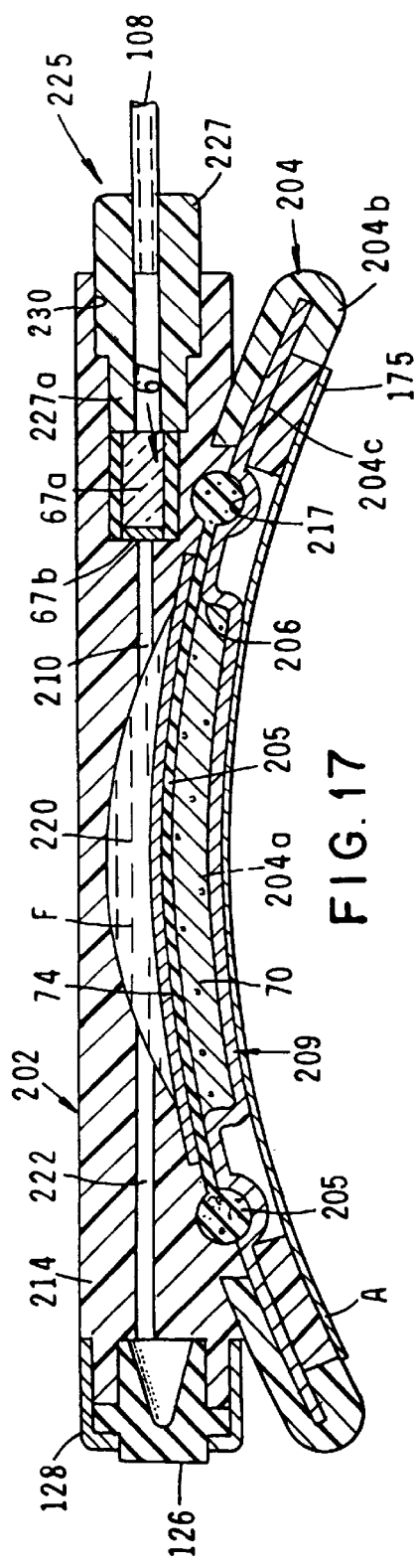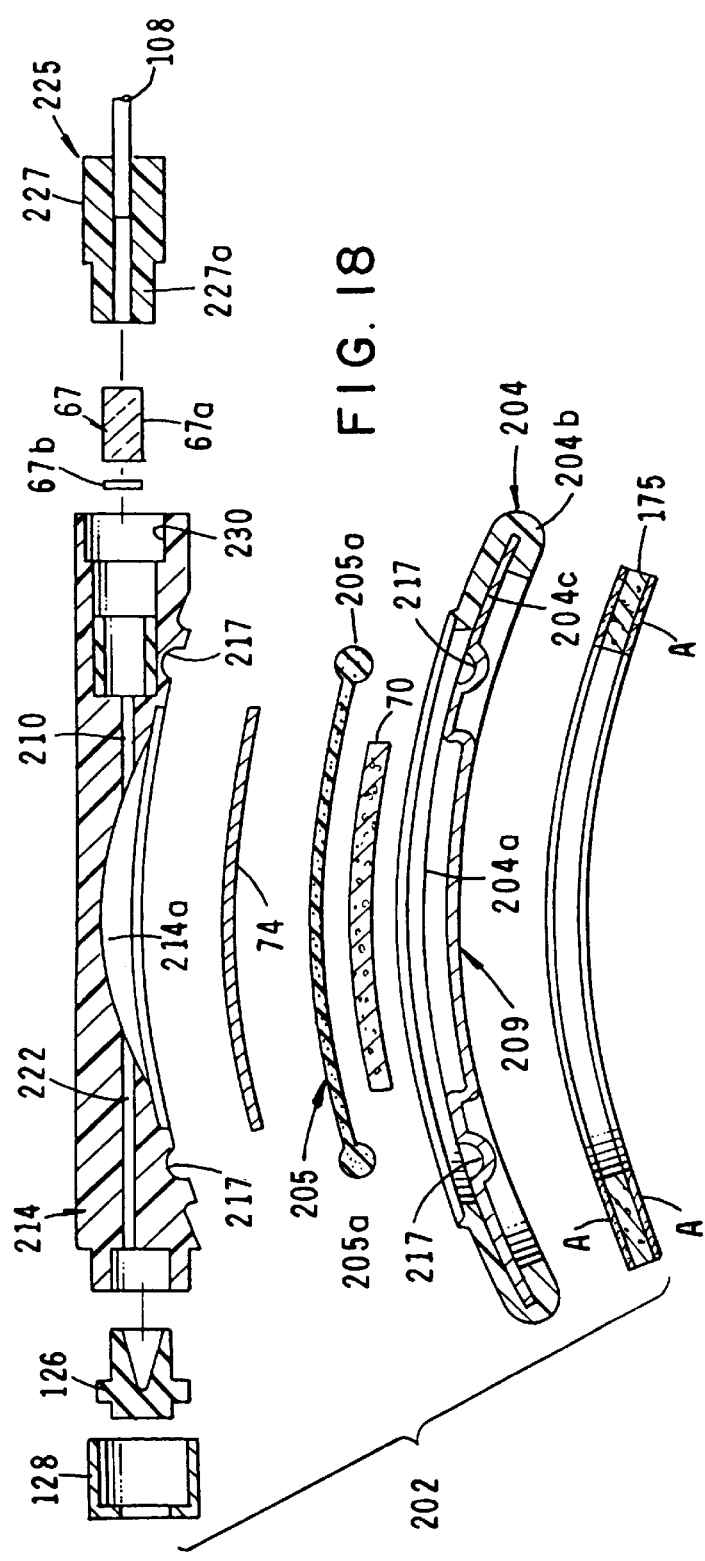

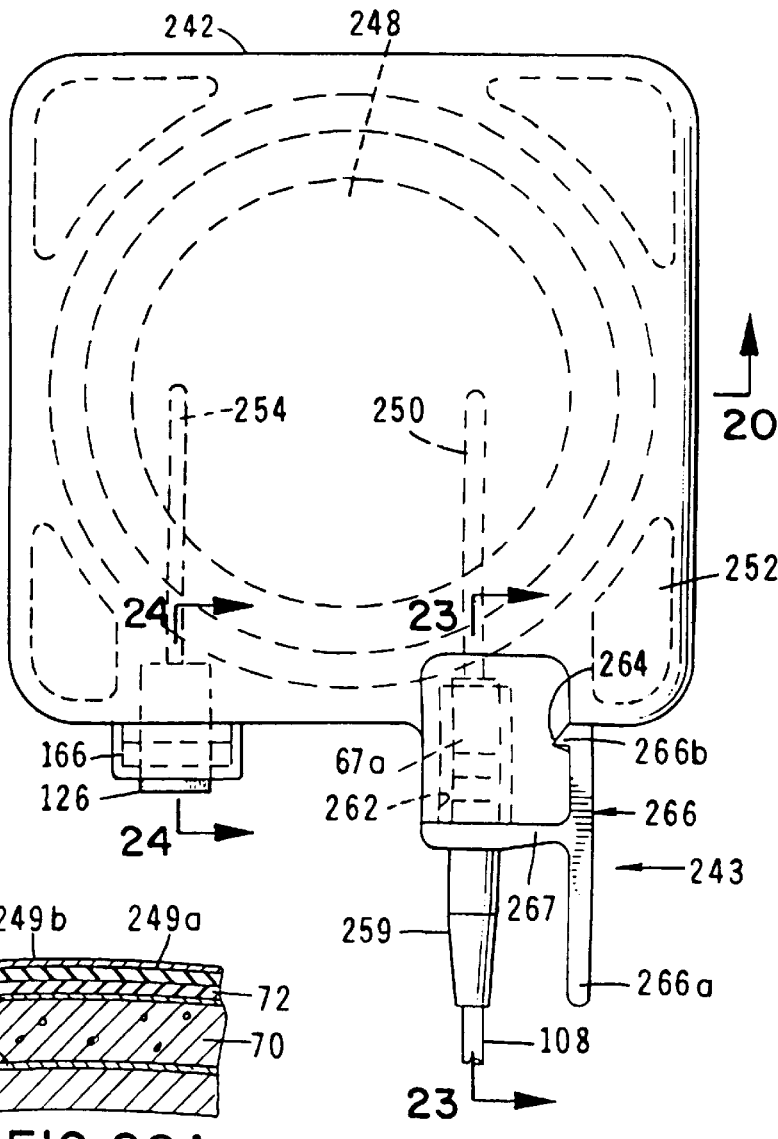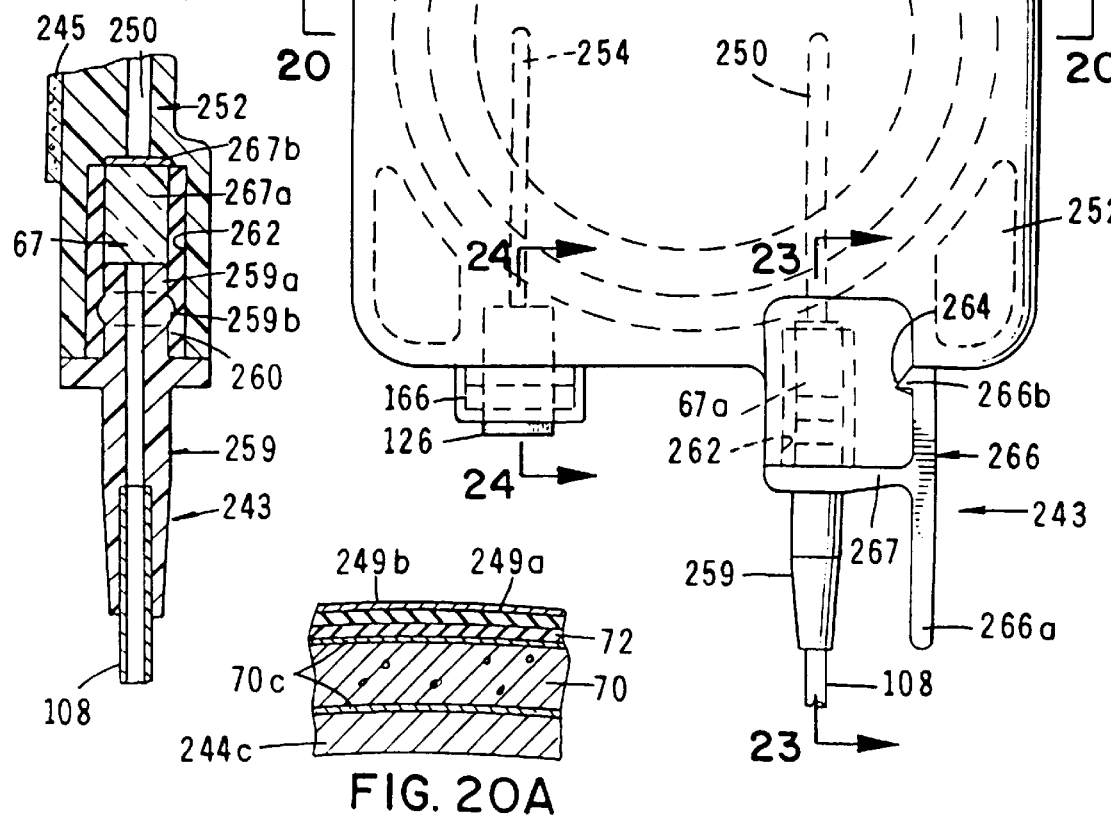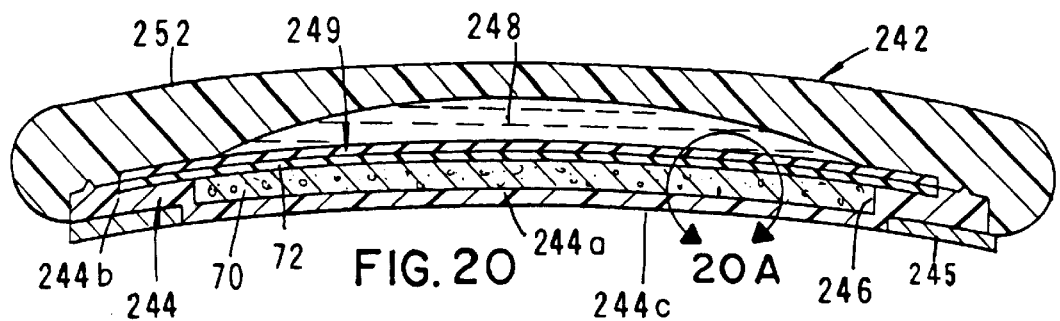

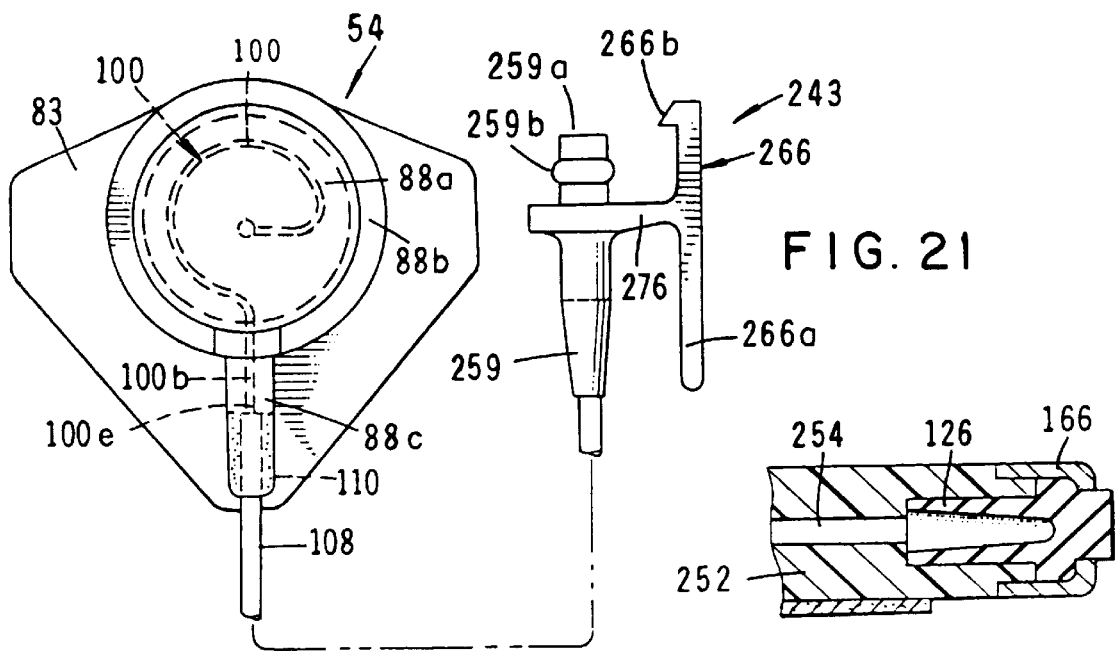
FIG. 21
FIG. 24
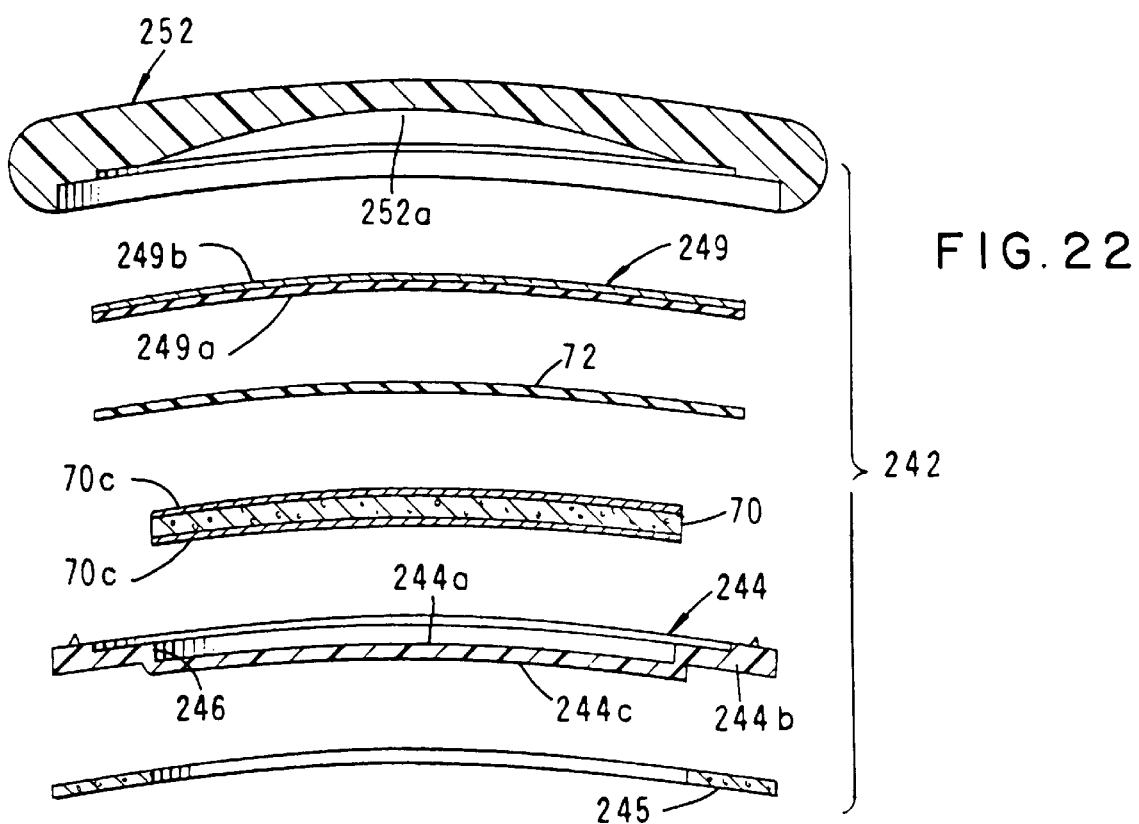
FIG. 22

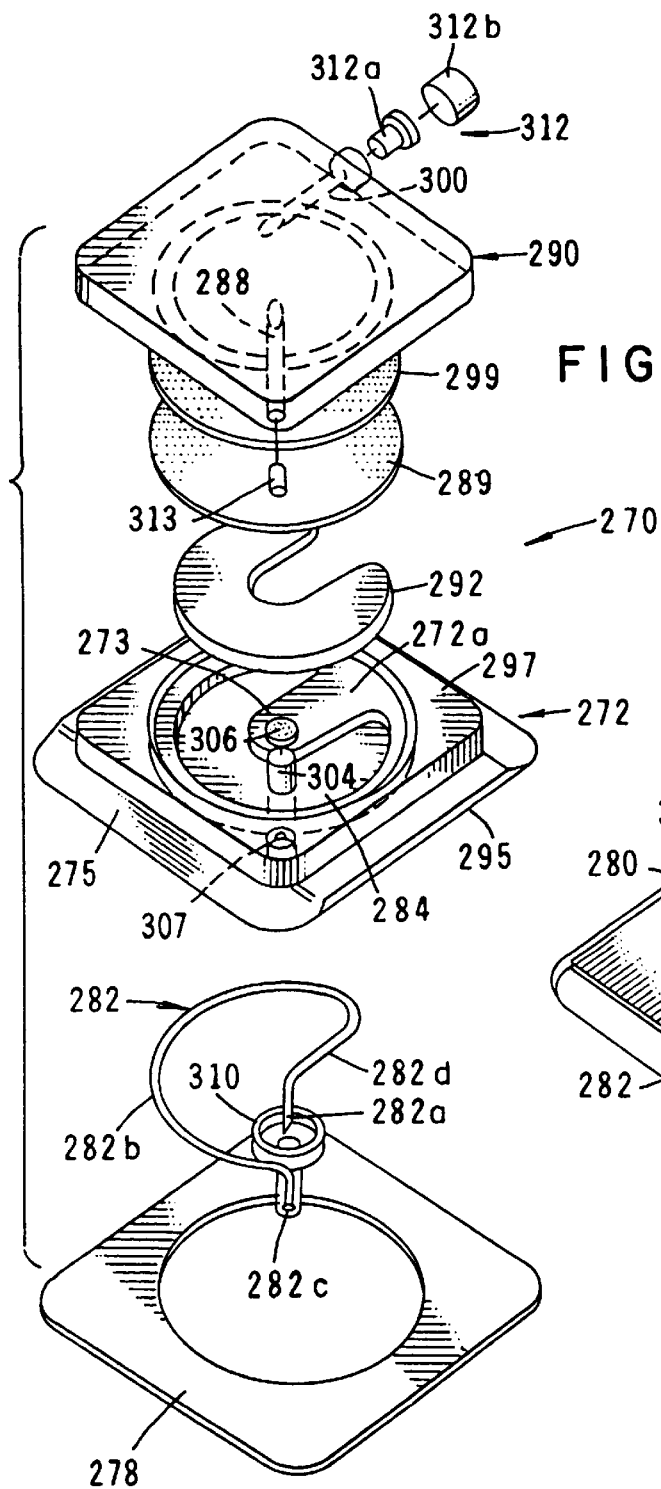
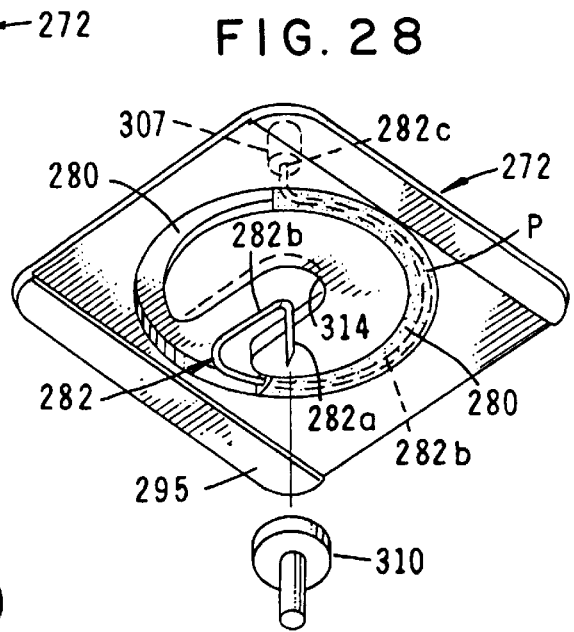
FIG. 27
FIG. 28

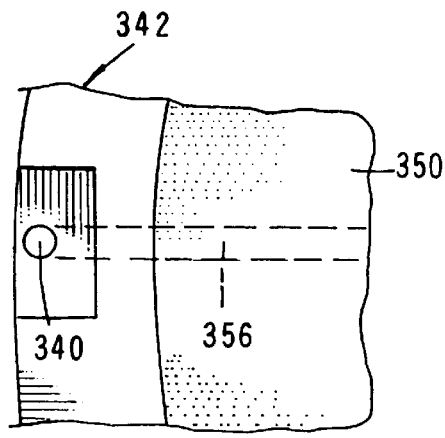
FIG. 34
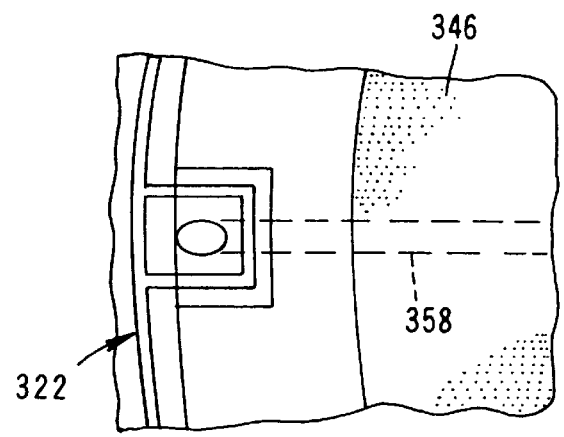
FIG. 35
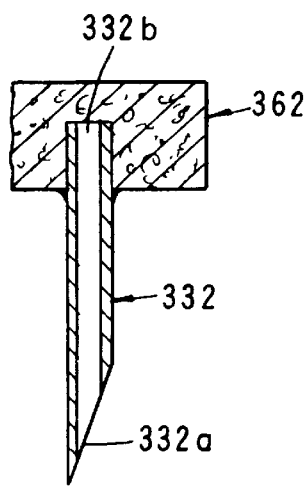
FIG. 38
FIG. 39
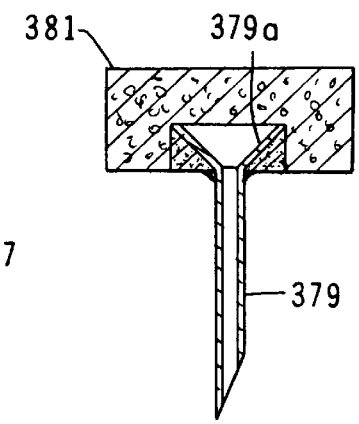
FIG. 40

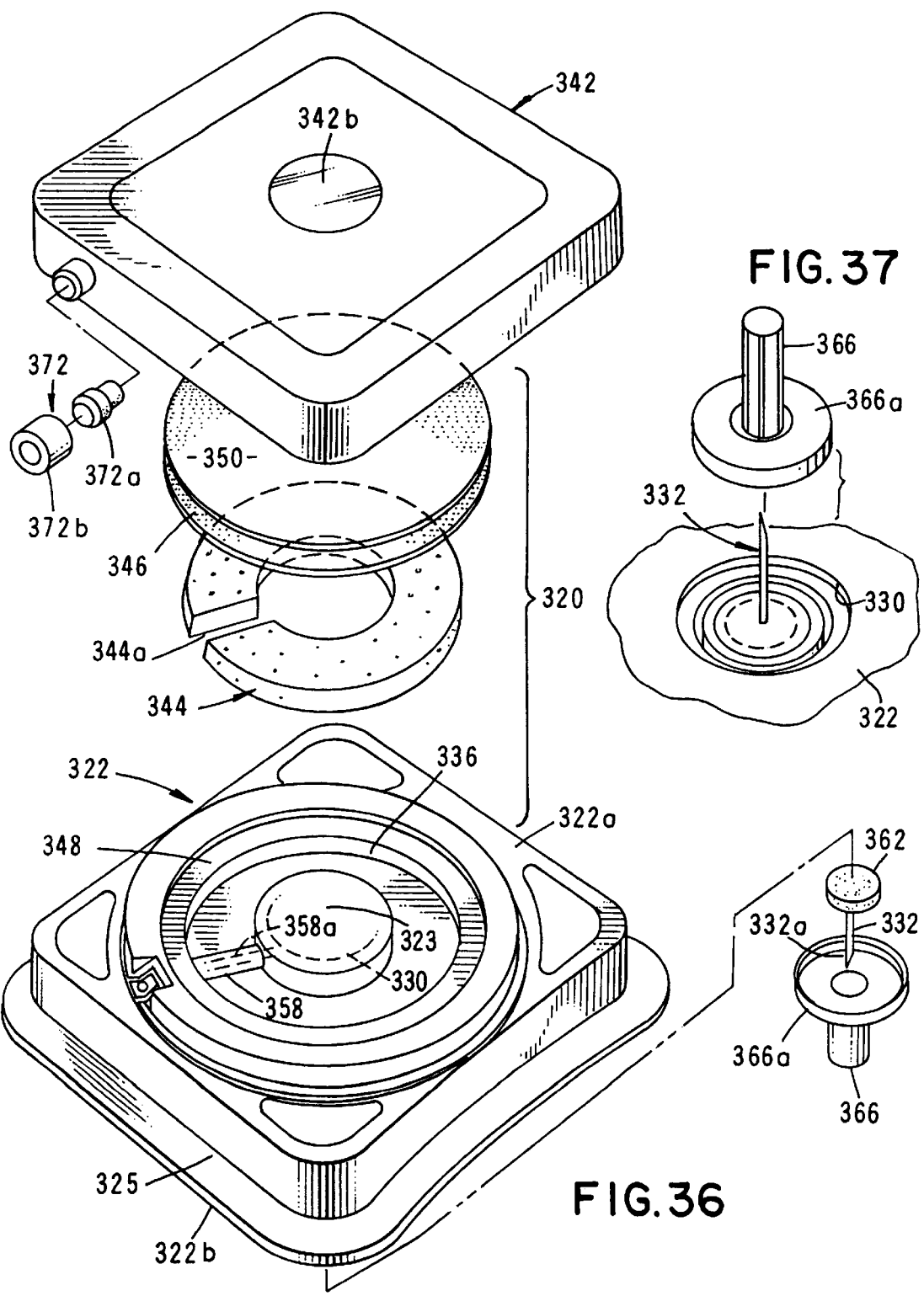

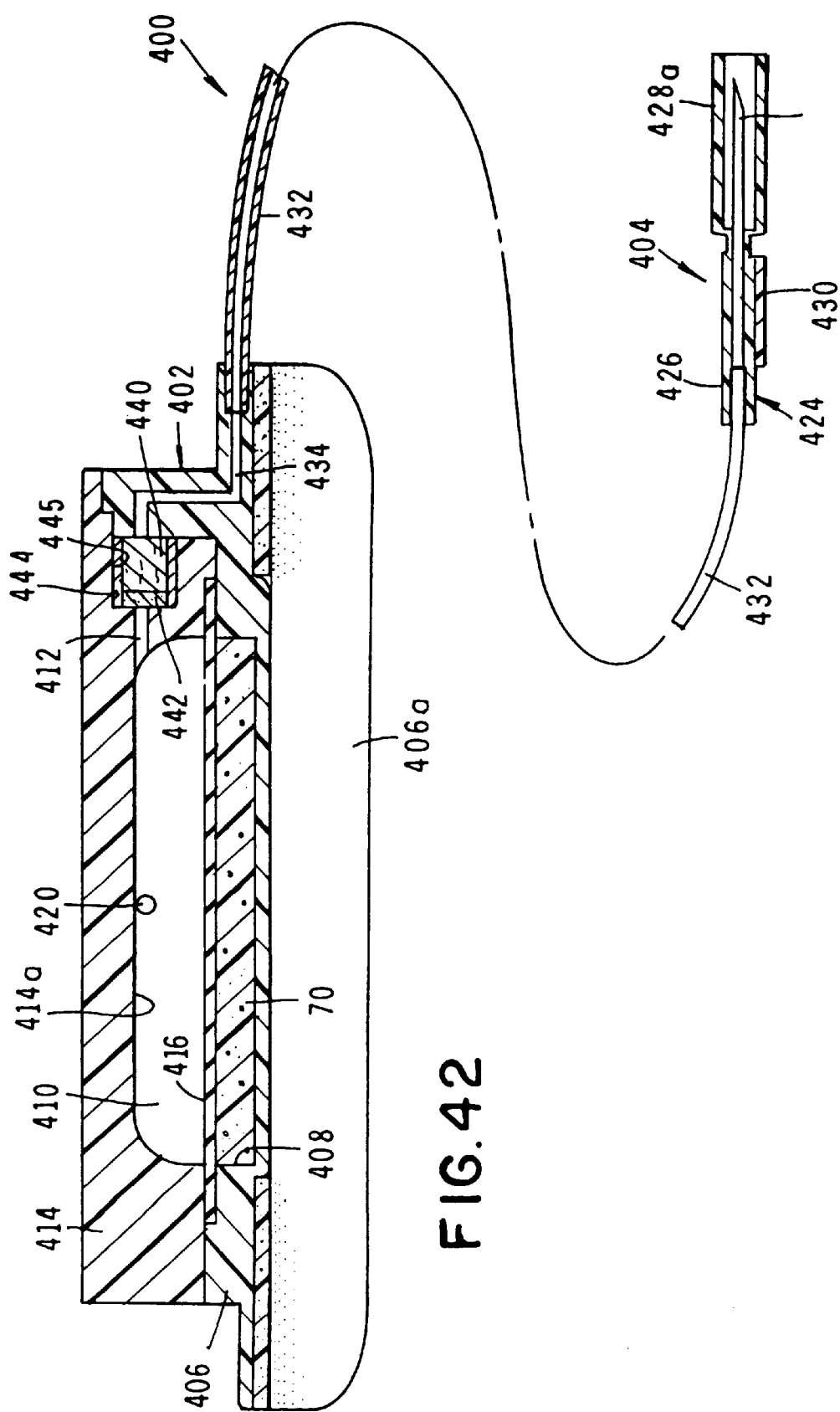

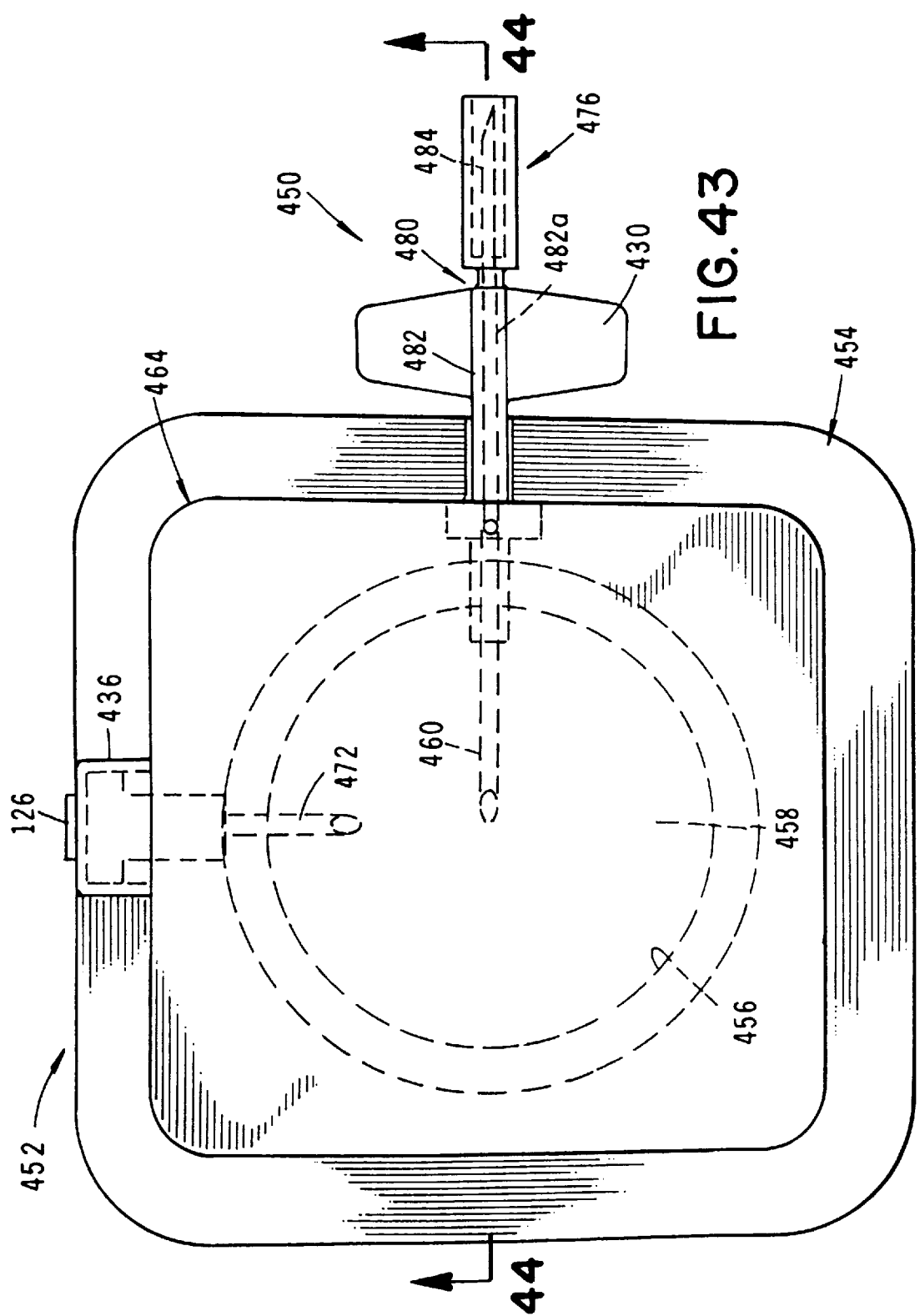

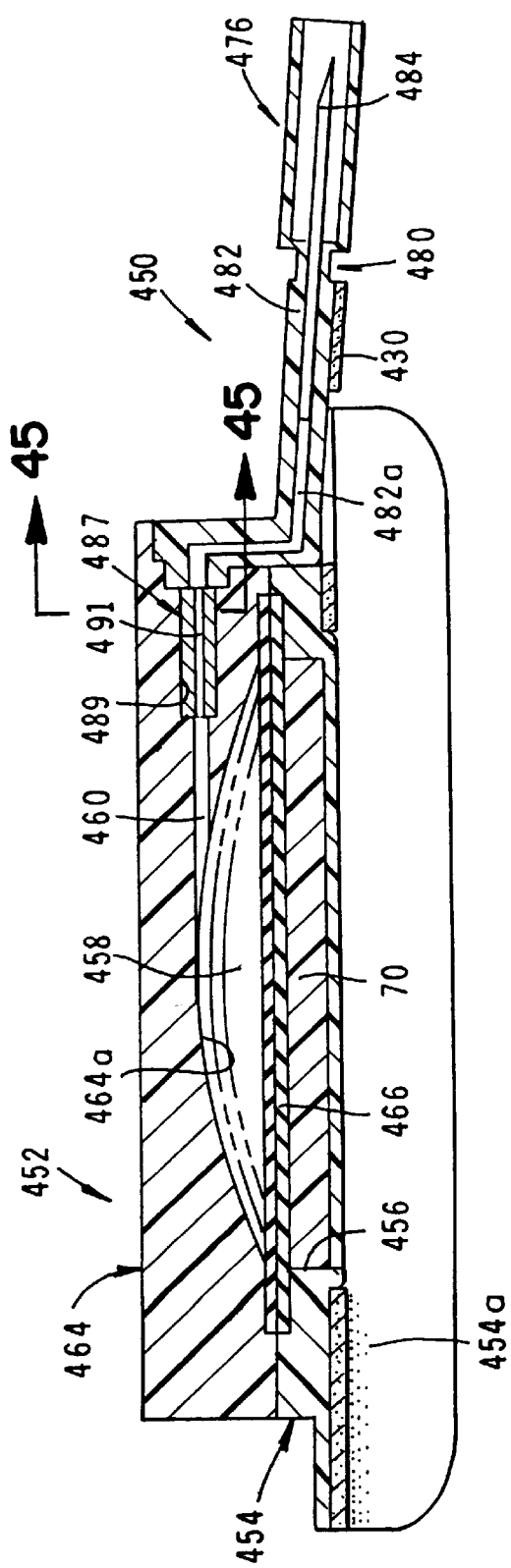
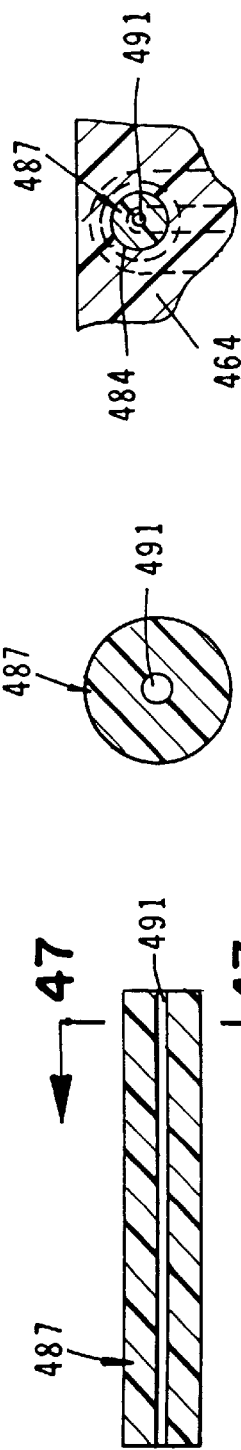
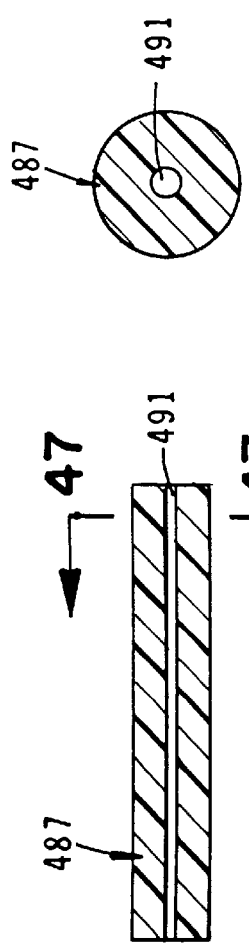

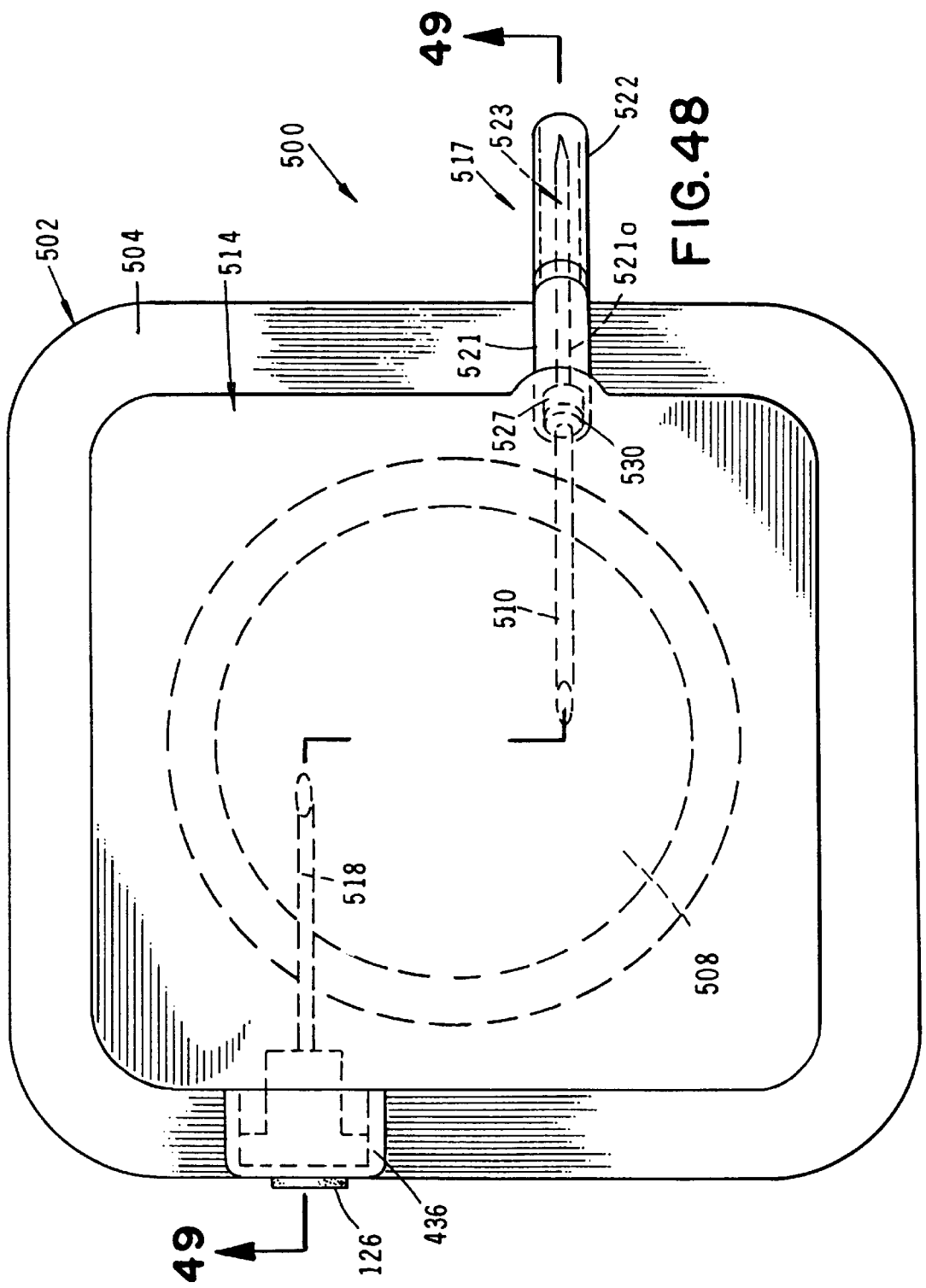

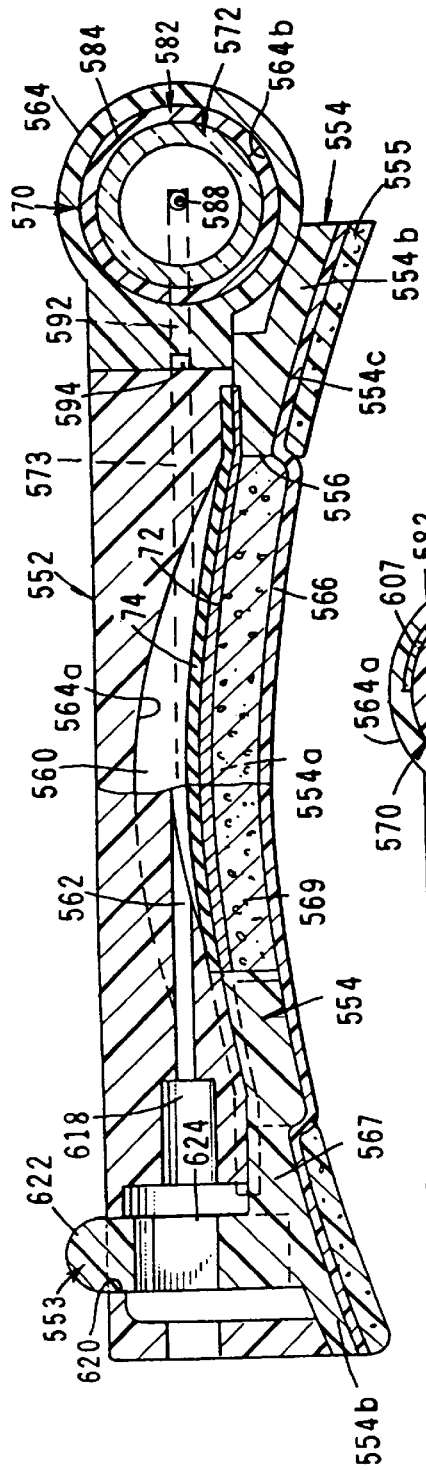
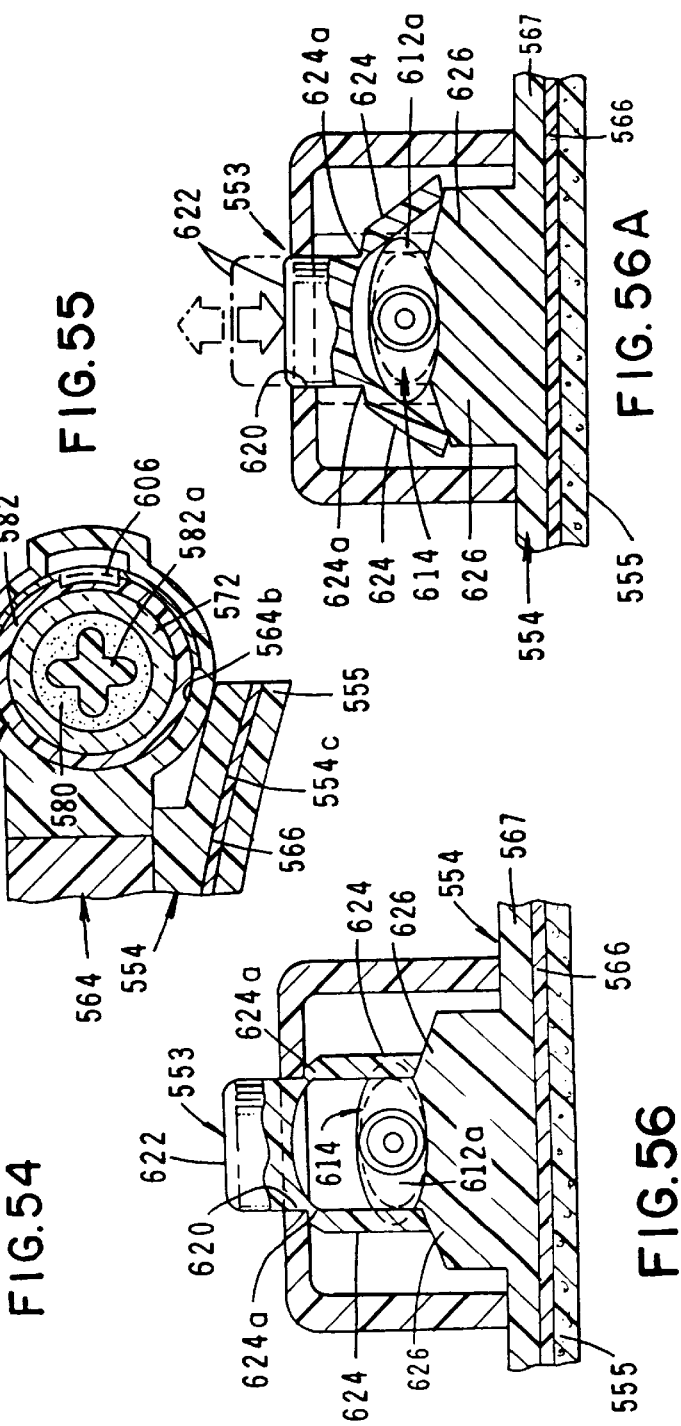
FIG.54
FIG.55
FIG.56
FIG.56A

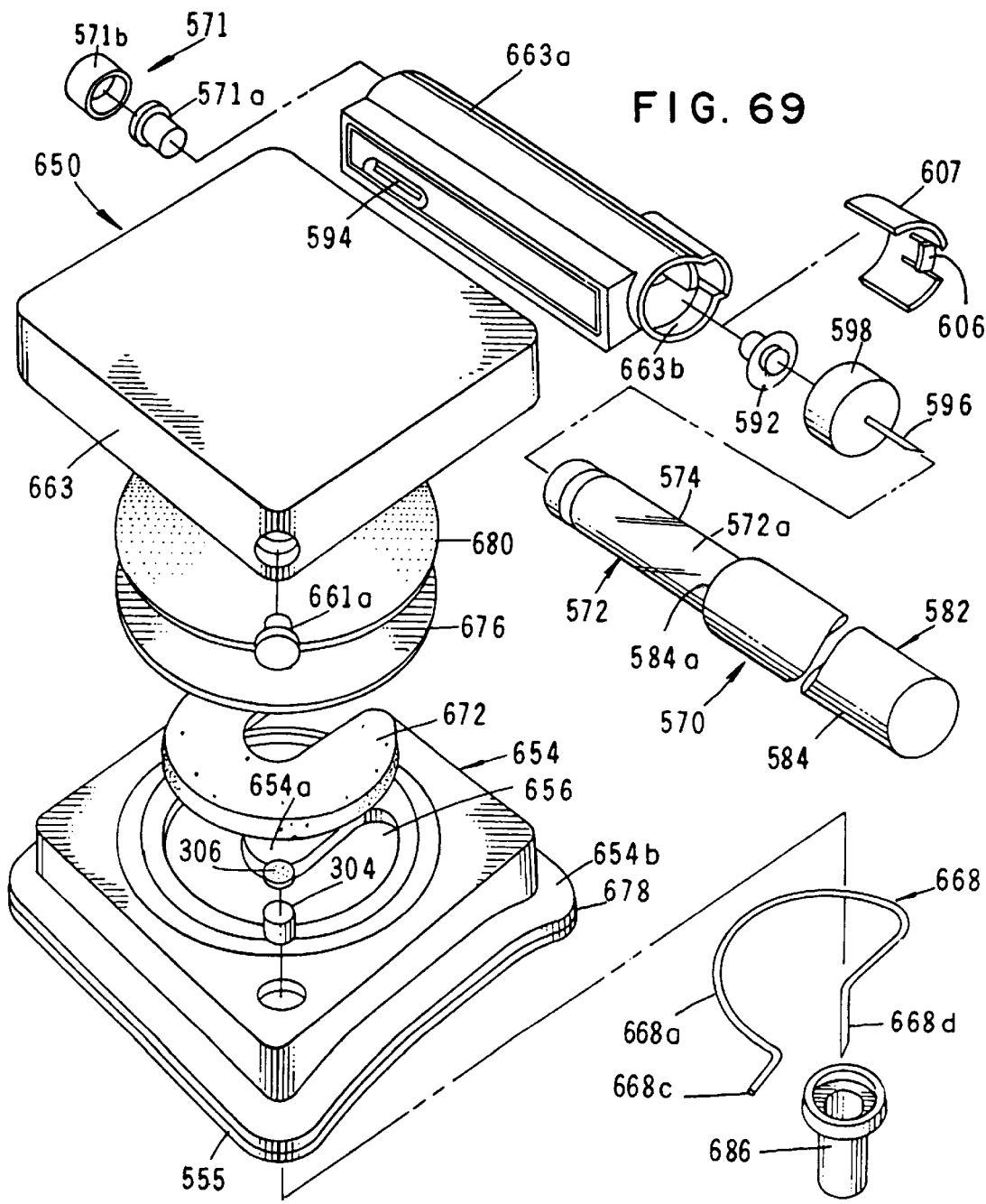

FLUID DELIVERY DEVICE WITH TEMPERATURE CONTROLLED ENERGY SOURCE

BACKGROUND OF THE INVENTION

This is a Divisional application of application Ser. No. 08/919,147 filed Aug. 27, 1997, now U.S. Pat. No. 5,961,942.

FIELD OF THE INVENTION

The present invention relates generally to fluid delivery devices. More particularly, the invention concerns an improved apparatus for infusing medicinal agents into an ambulatory patient at specific rates over extended periods of time.

DISCUSSION OF THE INVENTION

The oral route is the most frequent route of drug administration. Oral administration is relatively easy for most patients and rarely causes physical discomfort. However, many medicinal agents require a parenteral route of administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug my mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow means coupled with electronic based controls and typically involve the use of intravenous administration sets and the familiar bottle or solution bag suspended above the patient. Such methods are cumbersome, imprecise and, generally non-ambulatory requiring bed confinement of the patient. Periodic monitoring of the apparatus by the nurse or doctor is required to detect malfunctions of the infusion apparatus.

Devices of the character from which liquid is expelled from a relatively thick-walled bladder by internal stresses within the distended bladder have also been suggested for infusion of medicaments. For example, such bladder, or "balloon" type devices, are described in U.S. Pat. No. 3,469,578, issued to Bierman and in U.S. Pat. No. 4,318,400, issued to Perry.

A family of highly unique fluid delivery devices has been developed by the present inventor. These novel devices make use of recently developed elastomeric films, expandable foams and similar materials, which, in cooperation with a base define a fluid chamber that contains the fluid to be dispensed. The elastomeric film membrane or the expandable member controllably forces fluid within the chamber into outlet fluid flow channels provided in the device. Elastomeric film membrane devices are described in detail in U.S. Pat. No. 5,205,820 issued to the present inventor. U.S. Pat. No. 5,468,226, also issued to the present inventor, describes various types of expandable cellular elastomers and elastomeric foams used as the energy source of the fluid delivery device for expelling fluid from various physical forms of the fluid delivery device. Because of the pertinence of U.S. Pat. Nos. 5,205,820 and 5,468,226, these patents are hereby incorporated herein by reference in their entirety as though fully set forth herein. Co-pending U.S. application Ser. No. 08/541,030, filed Oct. 11, 1996 in which the present inventor is named as co-inventor, is also pertinent to one form of the apparatus of the invention which is described hereinafter. Accordingly, Ser. No. 08/541,030 is also hereby incorporated by reference as though fully set forth herein The apparatus of the present invention, which takes various physical forms, makes use of a novel temperature expansive material as an energy source. This family of devices can also be used with minimal professional assistance in an alternate health care environment, such as the home. By way of example, devices of the invention can be comfortably and conveniently removably affixed to the patient's body and can be used with or without remotely located infusion sets for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

One of the embodiments of the present invention comprises an ambulatory fluid dispensing system which includes a relatively thin body attached rigid base assembly and a uniquely designed stored energy means which cooperates with the base assembly for controllably expelling fluid from the reservoir of the device. In this form of the invention, the stored energy means is provided in the form of a heat expandable gel, the nature of which will be described in greater detail hereinafter. In this particular form of the invention, a novel, remotely located subcutaneous infusion set can be quickly coupled to the base assembly to enable precise infusion of fluid to a patient upon an increase in temperature of the expandable gel caused by the normal body temperature of the patient. Alternatively, in other embodiments of the invention, infusion is accomplished by infusion means integrally formed with the base assembly.

In still other embodiments of the invention which also use a heat expandable gel as an energy source, medicinal fluids are delivered to the patient from the fluid dispenser via various types of infusion means. By way of example, such dispensers can accomplish parenteral administration of a beneficial agent by the subcutaneous, subdermal, intradermal, intramuscular or intravenous routes. Subcutaneous injection places the drug into the tissues between the skin and the muscle. Drugs administered in this manner are absorbed somewhat slowly. When the beneficial agent is administered subcutaneously, the needle can be inserted at a 45 degree angle or, in some cases, as with obese patients, at a 90 degree angle. A beneficial agent administered by the intravenous route is given directly into the blood by a needle inserted into a vein. In such instances, action occurs almost immediately. An intramuscular injection is the administration of a beneficial agent into a muscle. Agents given by this route are absorbed more rapidly than those given by the subcutaneous route. In addition, a larger volume (1–5 mL) can be given at one site. The sites for intramuscular administration are the deltoid muscle (upper arm), the ventrogluteal or dorsogluteal sites (hip), and the vastus lateralis (thigh). When giving a beneficial drug by the intramuscular route, the needle of the infusion means is preferably inserted at a 90 degree angle.

The primary thrust of the various inventions described herein is to provide novel fluid delivery systems which are compact, easy to use, relatively low profile and are eminently capable of meeting even the most stringent of fluid delivery tolerance requirements. In this regard, medical and pharmacological research continues to reveal the importance of the manner in which a medicinal agent is administered. For example, certain classes of pharmacological agents possess a very narrow dosage range of therapeutic effectiveness, in which case too small a dose will have no effect, while too great a dose can result in toxic reaction. In other instances, some forms of medication require an extended delivery time to achieve the utmost effectiveness of a medicinal therapeutic regimen.

SUMMARY OF THE INVENTION

It is an object of the present invention to provide a technically advanced, fluid delivery apparatus for infusing medicinal fluids into a patient which is of a compact, low profile, laminate construction. More particularly, it is an object of the invention to provide an apparatus of such a character which embodies a novel thermal expanding polymer material which uniquely functions as an internal energy source for expelling the medicinal fluids from the device.

Another object of the invention is to provide an ambulatory fluid delivery apparatus which can conveniently be used for the precise infusion of various pharmaceutical fluids into an ambulatory patient at controlled rates over extended periods of time.

Another object of the invention is to provide an apparatus of the aforementioned character which is highly reliable and easy-to-use by lay persons in a non-hospital environment.

Another object of the invention is to provide an apparatus as described in the preceding paragraphs which can be used for subdermal, intradermal and intramuscular infusion of fluids. In this regard, in one form of the invention, the apparatus includes a novel and unique delivery cannula having a body portion disposed within a circuitous channel formed within the base superstructure of the apparatus and a pierceable portion which extends outwardly from the base of the apparatus. By constructing the cannula in a circuitous configuration and dynamically connecting it to the base assembly, movement of the cannula relative to the base assembly is permitted thereby minimizing needle related tissue necrosis.

Another object of the invention is to provide an apparatus which embodies as its stored energy source, a soft, pliable, semi-solid, heat-expandable mass which is heated by the patient's body temperature in a manner to controllably expel fluid from the device.

Another object of the invention is to provide an apparatus as described in the preceding paragraph in which the heat expandable mass is specifically tailored to provide precise, predictable protocol delivery of the medicinal agent stored within the reservoir of the device.

Another object of the invention is to provide an apparatus of the class described which includes novel means for indicating the presence of fluid within the reservoir and for also indicating fluid flow from the reservoir. A further object of the invention is to provide a low profile, body attaching fluid delivery device of laminate construction which can meet even the most stringent fluid delivery tolerance and flow signature requirements.

Another object of the invention is to provide an apparatus of the character described which includes a heat responsive, three dimensional polymer network which functions as a stored energy source and comprises one that can be constructed from various types of polymeric conformable materials such as phase transition gels.

Another object of the invention is to provide stored energy sources of the character described in the preceding paragraph which comprise blends or laminate constructions of phase transition gels that will enable the achievement of multi-rate delivery protocols.

Another object of the invention is to provide an apparatus of the character described which includes a novel, combination filter and rate control assemblage disposed intermediate the fluid reservoir and the outlet port of the device or intermediate outlet port of the device and the infusion means.

Another object of the invention is to provide an apparatus of the character described which, due to its unique construction, can be manufactured inexpensively in large volume by automated machinery.

Other objects of the invention are set forth in U.S. Pat. Nos. 5,205,820 and 5,468,226, which patents are incorporated herein by reference. Still further objects of the invention will become apparent from the discussion which follows.

BRIEF DESCRIPTION OF THE DRAWINGS

FIG. 1 is a top plan view of one form of the fluid delivery apparatus of the invention.

FIG. 2 is an enlarged, cross-sectional view taken along lines 2—2 of FIG. 1.

FIG. 3 is an enlarged, cross-sectional view similar to FIG. 2, but showing the heat expandable means of the device in an expanded configuration which will cause the fluid within the reservoir of the device to be controllably expelled therefrom.

FIG. 4 is an enlarged, cross-sectional view taken along lines 4—4 of FIG. 1, but showing the heat expandable means in an expanded configuration.

FIG. 6 is an enlarged, cross-sectional view taken along lines 6—6 of FIG. 1, but showing the heat expandable mass in an expanded configuration.

FIG. 6A is an enlarged view of the quick connect assembly.

FIG. 9 is an enlarged, cross-sectional view taken along lines 9—9 of FIG. 8.

FIG. 10 is a fragmentary, generally perspective view of the outlet portion of the device better showing the construction of the quick disconnect coupling mechanism of this particular form of the invention.

FIG. 11 is a fragmentary, side-elevational view of the apparatus, better showing the configuration of the fluid inlet port of the device.

FIG. 13 is a top plan view of still another form of the fluid delivery apparatus of the invention.

FIG. 14 is an enlarged, cross-sectional view taken along lines 14—14 of FIG. 13.

FIG. 17 is an enlarged, cross-sectional view taken along lines 17—17 of FIG. 16.

FIG. 18 is an enlarged, side-elevational, cross-sectional, exploded view of the device shown in FIG. 17.

FIG. 19 is a top plan view of still another alternate form of the device of the invention.

FIG. 20 is an enlarged, cross-sectional view taken along lines 20—20 of FIG. 19.

FIG. 20A is an enlarged fragmentary view of the area in FIG. 20 designated as 20A.

FIG. 21 is a top plan view of one embodiment of the infusion set of the invention shown interconnected with a quick coupler mechanism of the novel design as shown in FIG. 19.

FIG. 22 is a side-elevational, cross-sectional, exploded view of the apparatus shown in FIG. 20A.

FIG. 23 is an enlarged, cross-sectional view taken along lines 23—23 of FIG. 19.

FIG. 24 is an enlarged, cross-sectional view taken along lines 24—24 of FIG. 19.

FIG. 27 is a generally perspective, exploded view of the apparatus shown in FIG. 25.

FIG. 28 is a generally perspective bottom view of the form of the apparatus shown in FIG. 25.

FIG. 34 is a fragmentary view taken along lines 34—34 of FIG. 33.

FIG. 35 is a fragmentary view taken along lines 35—35 of FIG. 33.

FIG. 36 is a generally perspective, exploded view of the device shown in FIG. 30.

FIG. 37 is an enlarged, fragmentary, generally perspective view of the outlet and cannula cover portions of the apparatus shown in FIG. 36.

FIG. 38 is a side-elevational view of an alternate form of the cannula and flow control frit subassembly of the device.

FIG. 39 is a side-elevational view of another embodiment of the cannula subassembly of the invention.

FIG. 40 is a side-elevational view of still another form of the cannula and frit subassembly of the device.

FIG. 42 is an enlarged, cross-sectional view taken along lines 42—42 of FIG. 41.

FIG. 43 is a top plan view of yet another of the fluid delivery apparatus of the invention.

FIG. 44 is an enlarged, cross-sectional view taken along lines 44—44 of FIG. 43.

FIG. 45 is an enlarged, cross-sectional view taken along lines 45—45 of FIG. 44.

FIG. 46 is an enlarged cross-sectional view of the rate control member of this latest form of the invention.

FIG. 47 is a cross-sectional view taken along lines 47—47 of FIG. 46.

FIG. 48 is a top plan view of still another form of the fluid delivery apparatus of the invention.

FIG. 54 is a cross-sectional view taken along lines 54—54 of FIG. 53.

FIG. 55 is a cross-sectional view taken along lines 55—55 of FIG. 53.

FIG. 56 is an enlarged, cross-sectional view taken along lines 56—56 of FIG. 53.

FIG. 56A is a cross-sectional view, similar to FIG. 56, but showing the release button of the device in a depressed configuration.

FIG. 69 is a generally perspective, exploded view of the apparatus shown in FIG. 64.

DESCRIPTION OF THE INVENTION

Figure 5:
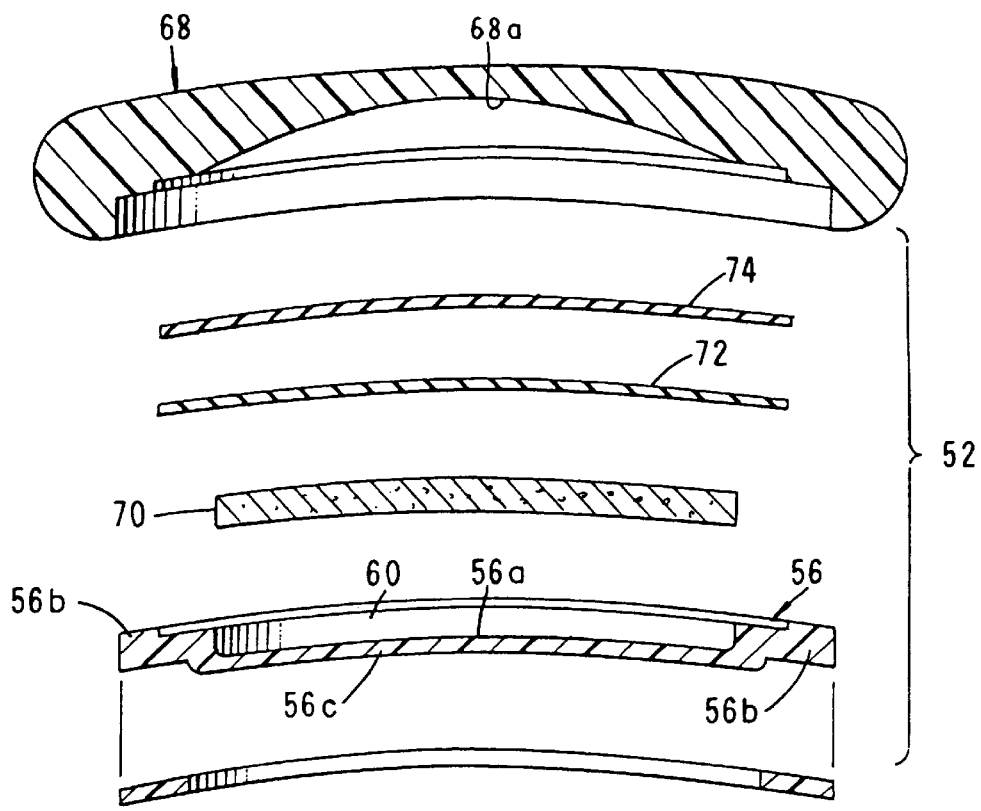
FIG. 5 is an enlarged, side-elevational, cross-sectional exploded view of the apparatus shown in FIG. 2.

Referring to the drawings and particularly to FIGS. 1 through 7, one form of the apparatus of the invention for use in the infusion of medicinal fluids into a patient is there shown and generally designated by the numeral 50. As best seen by referring to FIG. 1, the embodiment of the invention here shown comprises a low-profile, fluid storage device 52 and a cooperating, remotely located infusion means 54 for infusing the fluid stored in device 52 into the patient.

Turning particularly to FIGS. 2 and 5, it can be seen that fluid storage device 52 includes a thin base assembly 56 having a central portion 56a and peripheral portion 56b circumscribing central portion 56a. Base assembly 56 is provided with a curved lower surface 56c which is engagable with the patient when the device is taped or otherwise removably affixed to the patient such as by a pad-like member 58 having adhesive on both sides of the member. Formed within base 56 is a generally circular shaped chamber 60 (FIGS. 1 and 5), the purpose of which will presently be described. Forming an extremely important aspect of the apparatus of the present invention is a heat-expandable means which is carried within chamber 60 of base assembly 56 for causing the fluids contained within the sealed reservoir 64 of the device (FIG. 2) to flow outwardly through an outlet 66 formed in a cover 68 which is superimposed over and is connected to base 56 in the manner shown in FIGS. 1, 2, and 3. The heat-expandable means is here provided in the form of a thermal expandable polymer mass 70 which is disposed within chamber 60 in the manner best seen in FIG. 2.

Expandable mass 70 can take several forms, but a particularly attractive form for devices of the present invention comprises a semisolid form such as a gel. Unlike a liquid, which can offer no permanent resistance to change in shape and must be constrained within some type of container, expandable mass 70 is of a semisolid form which can advantageously be handled without external containment under ambient manufacturing conditions. From a technical viewpoint, gels are often characterized as soft solids which reside in a state between a liquid and a solid state. Frequently gels comprise a cross-linked network of long polymer molecules with liquid molecules trapped within the network. Many gels known in the prior art not only are capable of significantly large volume change in response to stimulus (phase-transition gels), but also exhibit physical characteristics that enable them to closely conform to the shape of an adjacent member such as a distendable membrane. Such gels are ideally suited for use as a stored energy means for of fluid delivery devices of the character described hereinafter and also of the character described in incorporated-by-reference application Ser. No. 08/541,030. As discussed in the aforementioned application, the conformable characteristics of the gel assist in insuring the complete and controlled expelling of fluids from the reservoir of the delivery device.

Phase transition gels best suited for use in constructing the heat expandable means of the present invention are gels which exhibit a large volume change at a given phase-transition condition. Unlike liquids, which exhibit a fixed temperature for state of vaporization to a known volume and with such vaporization point changing as a function of ambient pressure, the phase-transition gels in this invention are multicomponent polymers which can be made to respond with various volume changes to a singular external temperature stimuli.

Advantageously, the difference in volume between the expanded phase of these phase-transition gels and the contracted phase thereof can be orders of magnitude. Examples of suitable phase-transition gels are disclosed in Tanaka et al., U.S. Pat. No. 4,732,930; No. Re-35,068 and No. 5,403,893. Because of the pertinence of these patents, U.S. Pat. No. 4,732,930, U.S. Pat. No. 5,403,893 and U.S. Pat. No. Re-35,068 are all hereby incorporated by reference as though fully set forth herein.

While a number of the phase-transition gels described in the Tanaka et al patents can be used to construct the heat expandable stored energy means of the present invention, the ionized acrylamide gel compositions therein described are desirable in many applications because of the quite drastic volume change they exhibit in response to an external stimulus such as the body temperature of the patient. These ionized acrylamide gel compositions comprise a cross-linked, partially ionized polyacrylamide gel wherein between up to 20% of the amide groups are hydrolyzed to carboxyl groups. The gel includes a solvent of a critical concentration at which even a slight change in temperature, pH or salt concentration causes the gel to shrink or swell dramatically. As pointed out by Tanaka et al in the aforementioned patents, the particular critical concentration utilized in the gel composition depends upon the solvent employed, the temperature of the gel and the degree of hydrolysis of the gel. The gel also can contain a positive metal ion such as sodium or magnesium which has the effect of increasing the change in gel volume caused by change of solvent concentration, temperature, pH or, salt concentration.

Another form of phase-transition gel suitable for use in the apparatus of the present invention comprises interpenetrating polymer networks which include a first polymer and a second polymer wherein the second polymer interpenetrates the first polymer. Suitable first and second polymers include polymers which can interact during exposure to a phase-transition condition to thereby cause a significantly large volume change of the gel. Suitable interpenetrating polymer networks can also include more than two polymers. For example, additional polymers can be included in the network which interpenetrate the first and/or second polymers. The nature of these polymers as well as the nature of the interaction between the polymers is discussed in detail in Tanaka, U.S. Pat. No. 5,403,893, and will not here by repeated.

The responsive gels may also be reversibly responsive. For example, such gels experience certain environmental changes, the entire gel, or a component thereof will undergo a reversible volumeric change which typically involves a shift between two equilibrium states as, for example, expanded and collapsed. This reversible volume change of the entire gel, or a component of the gel may be either continuous or discontinuous. Typically, a continuous volume change is marked by a reversible change in volume that occurs over a substantial change in environmental condition. On the other hand, the gel, or a component thereof, may undergo a discontinuous volume change in which the reversible transition from expanded to collapsed states, and back again, typically occurs over a relatively small change in environmental condition. A gel undergoing a continuous phase-transition may have a similar order of magnitude total volume change as a gel undergoing a discontinuous phase-transition.

In a slightly different vein, the gel may be combined with a material that acts as a molecular transducer, converting an environmental condition into an appropriate trigger. For example, a dye or like material which is designed to absorb light and convert the light energy into heat may be introduced into a temperature responsive gel so as to trigger the gel to undergo a temperature induced rapid phase transition.

Typically, volumetric changes in the phase transition gels result from competition between intermolecular forces, usually electrostatic in nature. Such volumetric changes are believed to be driven primarily by four fundamental forces, that is ionic, hydrophobic, hydrogen bonding and van der Waals bonding interactions, either alone or in combination. Changes in temperature most strongly affect hydrophobic interactions and hydrogen bonding.

Of particular interest is the fact that gels consisting of copolymers of positively and negatively charged groups may be formulated so that the volume change is governed by more than one fundamental force. In these gels, polymer segments typically interact with each other through ionic interactions and hydrogen bonding.

By way of summary, gels suitable for use as the stored energy sources of the present invention include various cross-linked polymers and gels which can be synthesized from the polymerization of a monomer and a cross-linking agent.

More particularly, suitable gels can be made from any polymer with side groups that can react with a di-or multi-functional cross-linking molecule. However, the simplest system from which gels can be made are polymers with hydroxyl, acid or amine side groups.

By way of non-limiting example, suitable gels for use as the stored energy means may consist, in whole or in part, of polymers made by copolymerization/cross linking of mono-functional and polyfunctional polymerizable vinyl monomers. The monomer may include N,N-disubstituted acrylamides such as N,N-dialkylsubstituted acrylamides, or di-N,N substituted acrylamides where the dissubtitution form part of a ring, acrylate ethers, alkyl substituted vinyl ethers, glycol ethers, and mixtures thereof.

Exemplary polymeric gel networks thus may contain poly(N,N-dialkylacrylamide), poly(ethyl acrylate) and mixtures thereof, as well as polymers of N-alkylacrylamide (or analogous N-alkylmethacrylamide) derivatives such as N-ethylacrylamide, N-n-propylacrylamide, N-n-propylmethylacrylamide, or various acrylate copolymers.

Exemplary cross-linking agents may include ethylene glycol diacrylate (EGDA); di(ethylene glycol)bis(allyl carbonate) ("DEGBAC"); methylenebis(acrylamide) ("bis"); ethylene glycol dimethacrylate ("EGDMA"); magnesium methacrylate ("MgMA$_2$"); and mixtures thereof. Cross-linkers suitable for polymeric precursors may include diglycidyl ether, divinyl sulfone, epichlorohydrin, phosphoryl chloride, trimetaphosphate, trimethylomelamine, polyacrolein, and ceric ion redox systems, although the most preferred of these will not have active hydrogens. The cross-linking agent effects partial cross-linking of the polymer and provides a means to control the gel's mechanical strength, swelling degree, and intensity of volume change trigger by changing the cross-linking density. Cross-linking of linear polymers by chemical reagents is preferred for gels made from biological polymers such as cellulose ethers. Preferred cross-linkers for polysaccharide gels, especially cellulos ethers, are multifunctional carboxylic acids, such as adipic acid (hexanedioic acid: HOOC(CH$_2$)$_4$COOH), succinic acid (HOOC(CH$_2$)$_2$COOH), malonic acid (propanedioic acid: CH$_2$(COOH)$_2$, sebacic acid (decanedioic acid: HOOC(CH$_2$)COOH), glutaric acid (pentanedioic acid: HOOC(CH$_2$)$_3$COOH), or 1, 10 decanedicarboxylic acid.

Turning particularly to FIG. 2, it is to be noted that sealing means are superimposed over chamber 60 and expandable mass 70 to seal chamber 60. This sealing means here comprises a distendable membrane 72 which is sealably connected to the peripheral portion 56b of base 56 in the manner shown in FIGS. 2 and 3. Overlaying membrane 72 is a distendable membrane 74 which, in cooperation with a generally concave shaped cavity 68a formed in cover 68, forms fluid reservoir 64 (FIG. 2). It is to be understood that the reservoir defining cavity can be of any desired geometry. More particularly, as best seen in FIG. 2, membrane 72 sealably covers chamber 60 and mass 70 while membrane 74 overlays sealing membrane 72 and is bonded to cover 68. This constriction enables membrane slip, that is the ability of the membranes to move relative to each other. In a manner presently to be described, fill means are provided for introducing fluids into reservoir 64 through a fluid inlet 78 formed in cover 68 (FIG. 6). As mass 70 is heated, it will controllably expand from the configuration shown in FIG. 2 to the expanded configuration shown in FIG. 3 and, in so doing, will experience a change in volume. Mass 70 can be free standing or, if desired, can be encapsulated within a yieldably deformable covering made up of interconnected layers 70c of the character shown in FIG. 22.

With the construction of the fluid storage device 52 shown in FIG. 2, when the heat expandable mass 70 is heated causing it to expand into the configuration shown in FIG. 3 it will controllably force the fluid "F" which is contained within the reservoir 64 outwardly thereof through an outlet passageway 66. As mass 70 expands, it will distend both sealing membrane 72 and distendable membrane 74 in a direction toward inner wall 68a (FIG. 2). It is to be noted that as membrane 74 moves toward its distended configuration, it will closely conform to the shape of heat-expandable, conformable mass 70 resulting in a complete and controlled expelling of fluid from reservoir 64 through fluid outlet 66 and into the infusion means 54 of the apparatus, the details of construction of which will presently be described. It is to be understood that in certain embodiments of the invention only a single sealing membrane need be used to provide a barrier between mass 70 and reservoir 64.

As best seen in FIG. 2, cover 68, in cooperation with distendable membrane 74 forms reservoir 64. If desired, medicament and instruction labels 69 (FIG. 1) can be affixed to cover 68 to identify the medicinal fluid contained within reservoir 64 of the device.

For a discussion of the various materials that can be used to construct base 56, cover 68, and membranes 72 and 74, reference should be made to U.S. Pat. No. 5,205,820. This patent also discusses in greater detail techniques for labeling and venting of the fluid storage device where necessary.

Figure 7:
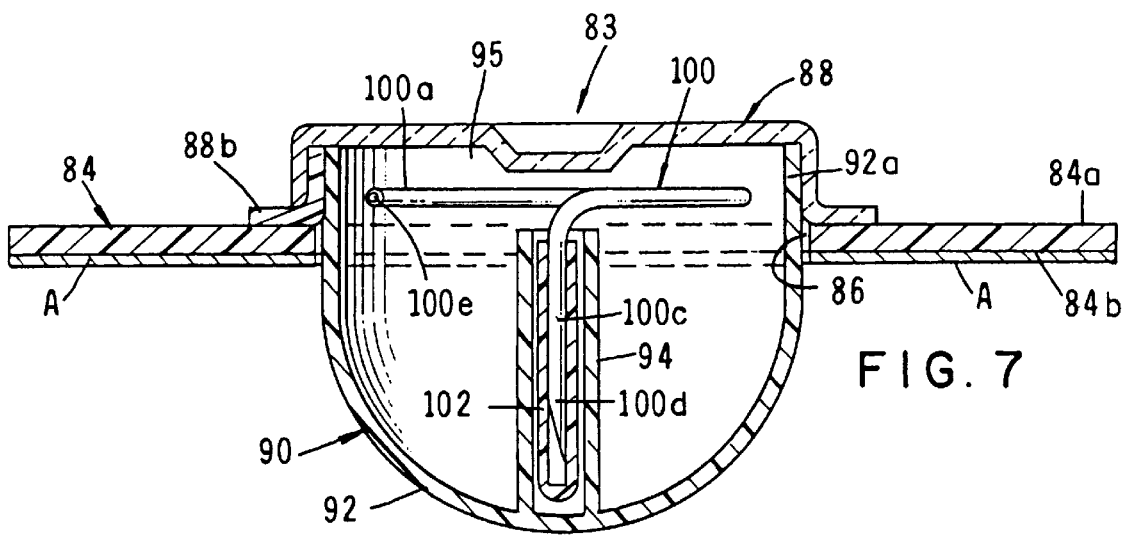
FIG. 7 is an enlarged, cross-sectional view taken along lines 7—7 of FIG.

Forming a unique aspect of the apparatus of the present invention is the previously identified, remotely located infusion means 54 for infusing medicinal fluids from fluid reservoir 64 into the patient. As best seen in FIGS. 1 and 7, the infusion means here comprises the subcutaneous infusion device 83 which includes a base 84 having upper and lower surfaces 84a and 84b and a generally circular-shaped opening 86 (FIG. 7). Connected to the upper surface 84a of base 84 is the cover 88 having a generally dome-shaped portion 88a, a flange portion 88b, and a stem portion 88c (FIG. 1). Removably receivable within opening 86 is a generally dome-shaped closure assembly 90 which includes an outer wall 92 which terminates in a generally cylindrically shaped skirt portion 92*a*. Formed internally of wall 92 is a tubular-shaped, socket-like portion 94 (FIG. 7), the purpose of which will presently be described.

Cover 88 and wall 92 cooperate to define a chamber 95 which houses the novel hollow cannula 100 of the invention. Cannula 100 includes a circuitously shaped body portion 100*a* which is disposed within chamber 95 and a stem portion 100*b* which is mounted within stem portion 88*c* of cover 88. Cannula 100 also includes an outlet end here provided in the form of a needle-like segment 100*c* which extends generally perpendicularly downward from surface 84*b* of base 84 and is used for subdermal infusion of medicinal fluids into the patient. For this purpose, segment 100*c* is provided with a sharp ground needle pointed extremity 100*d* (FIG. 7). Also shown in FIG. 7 is a twist-off protective sheath 102 which is telescopically received within socket-like portion 94. Sheath 102 surrounds and protects segment 100*c* of the cannula.

Preferably stem portion 100*b* of the very small diameter spiral cannula 100 is encased within the inboard end 108*a* of a fluid delivery administration tube 108 (FIG. 1) and the assembly thus formed is rigidly supported within stem 88*c* by encapsulation means such as a standard potting compound 110 of a character well known to those skilled in the art. Compound 110 rigidly supports the stem portion of the cannula within stem 88*c* so as to provide a secure interconnection of the cannula with base 84 and cover 88.

As best seen in FIGS. 1, 4, and 6A, a quick connect assembly 112 enables quick interconnection of the delivery administration tube or line 108 with cover 68 so that the delivery line is placed in fluid communication with outlet 66 of reservoir 64. Quick connect assembly 112 includes a body portion 114 having a hub 114*a* which is closely received within a socket 116 formed in cover 68 (FIG. 1). Formed on hub 114*a* is an enlarged diameter, bead-like protuberance 115 which sealably engages socket 116. A locking flange 118 is provided proximate hub 114 and is adapted to be lockably engaged by a pair of resiliently deformable locking arms 120 provided on cover 68. A pair of finger engaging locking levers 122, which are connected to body portion 114, can be squeezed together in a manner to spread the arms apart a distance sufficient to permit the removal of flange 118 from between the hook-like extremities 120*a* of arms 120. As indicated in FIG. 1, hook-like extremities 120*a* lockably grip flange 118 when socket portion 114 of the quick connect coupler is seated within a cavity 116 provided in housing 68 of the device. However, when it is desired to separate the infusion set 54 from the storage device 52, an inward finger pressure exerted on arms 122 will spread extremities 120*a* a distance sufficient to permit passage of flange 118 and removal of hub 114*a* from cavity 116.

In using the apparatus of the present invention, reservoir 64 is first filled with the beneficial agent to be infused into the patient. This is accomplished through use of the fill means of the invention, which here comprises a non-coring, elastomeric septum 126. As shown in FIG. 6, septum 126 is securely held in position within cover 68 by a clamping ring 128. Septum 126 is of standard construction and is penetrable by a cannula "C" of a filling syringe which is also of conventional construction. The conventional syringe (not shown) can be used to introduce the fluid to be dispensed to the patient into inlet passageway 78 and thence into reservoir 64. It is to be understood, however, that reservoir 64 can also be filled at the factory at the time of manufacture of the fluid storage device. Alternatively, the reservoir can be filled in the field shortly before use by means of the conventional syringe.

With reservoir 64 filled in the manner shown in FIG. 2 of the drawings, the infusion device can be interconnected with the fluid storage device 52 in the manner previously described. This done, closure assembly 90 of the infusion device 54 is then separated from the base 84 and protective sheath 102 is slipped from end 100*c* of cannula 100. With end 100*c* of cannula 100 thus exposed, the infusion device can be interconnected with the patient by penetrating the patient's skin with the sharp point 100*d* of the infusion cannula 100. As the infusion needle penetrates the patient's skin and tissue, the lower surface of base 84, which is preferably coated with an adhesive "A", or a suitable adhesive coated pad, will engage the patient's skin so as to hold the device securely in position. If desired, a peelable cover can be emplaced over a portion of the lower surface of the device to maintain the adhesive "A" in a sterile condition until time of use.

When the fluid storage device portion of the apparatus, that is portion 52 is affixed to the patient's body, such as to an arm, leg, or abdomen, the patient's body temperature acting through heat sink 56 will cause heat expandable mass 70 to expand thereby causing the fluid "F" contained within reservoir 64 to controllably flow under pressure toward outlet passageway 66. For this purpose, mass 70 should controllably expand within a temperature range of between about 70 to 100 degrees Fahrenheit. The fluid "F" entering outlet passageway 66 will flow through a fluid flow control means, shown here as flow control assembly 67, into delivery tube 108 and then into inlet 100*e* of cannula 100 (FIG. 7). Flow control assembly 67 is of a character well known to those skilled in the art and may comprise a rate control or impedance member 67*a* constructed from a porous ceramic, a plastic, a sintered metal or other suitable materials which will control the rate of fluid flow toward delivery tube 108. Also comprising a part of the flow control means is a filter 67*b* for filtering particulate materials from the fluid flowing outwardly of the device. Various filter materials of a character well known to those skilled in the art can be used to construct filter 67*b*.

While cannulas of conventional construction can be used as the infusion means, a novel feature of the present invention relates to the novel design of the circuitously shaped cannula and the unique manner of its interconnection with base 84 and cover 88. More particularly, with the novel construction shown in the drawings, when the device is connected to the patient so that the needle portion 100*c* of the cannula penetrates the patient's skin and tissue as, for example, that found on the patient's arm, leg, or abdomen, normal movement by the patient will permit the dynamically mounted portion of the cannula to move three dimensionally within chamber 95 while the base remains completely stationary. Without this important feature, normal movements by the patient causing flexing of the muscle or tissue can cause irritation and discomfort to the patient and could possibly cause needle related tissue neocrosis. However, the novel dynamic mounting of the cannula within chamber 95 positively prevents irritation to the patient as a result of normal muscle flexing by the patient.

Turning to FIGS. 8 through 12, an alternate form of the apparatus of the invention for use in the infusion of medicinal fluids into a patient is there shown and generally designated by the numeral 130. This alternate embodiment is similar in many respects to that shown in FIGS. 1 through 7 and like numerals are used in FIGS. 8 through 12 to identify like components. As best seen by referring to FIGS. 8 and 9, the apparatus here comprises a low-profile, fluid-storage device 132 and a cooperating, remotely located infusion means 54 for infusing the fluid stored in device 132 into the patient. While the infusion means 54 of the invention is identical to that previously described in connection with FIGS. 1 through 7, the fluid storage device 132 is of a somewhat different construction. More specifically, while fluid storage device 132 also comprises a thin base 136 having a central portion 136*a* and peripheral portion 136*b* circumscribing central portion 136*a*, unlike base 56 of the earlier described embodiment, base 136 for this application is provided with a curved lower surface 136*c* of the character shown in FIG. 9. Surface 136*c* is disposed proximate the patient when the device is taped or otherwise removably affixed to the patient, such as by using a foam tape 138 which has an adhesive "A" on both sides of the tape. Additionally, as will presently be discussed, this latest form of the invention includes a quick coupling mechanism of different design for coupling the infusion means with the fluid storage component.

Formed within base 136 is a generally circular shaped chamber 140 within which a heat-expandable means is carried. As before, this heat-expandable means functions to controllably force the fluids contained within the sealed reservoir 144 of the device to flow outwardly through an outlet 146 formed in a cover 148 which is superimposed over base 136 in the manner shown in FIGS. 9, 10, and 11. The heat-expandable means is of the character previously described herein and is covered by a sealing means comprising a membrane 72 which is sealably connected to the peripheral portion 136*b* of base 136 in the manner indicated in FIGS. 9 and 12. Overlaying membrane 72 is a distendable barrier membrane 74 which is bonded to the cover and which, in cooperation with a cavity 148*a* formed in cover 148, forms fluid reservoir 144 (FIG. 9). Fill means of the same character described in connection with the first embodiment of the invention are provided for introducing fluids into reservoir 144 through a fluid inlet 150 formed in cover 148. As the heat expandable means or semi-solid mass 70 is heated by the body heat of the patient, it will controllably expand causing any fluid contained within the reservoir to flow outwardly thereof through outlet passageway 146. As before, when mass 70 expands, it will distend sealing membrane 72 and distendable membrane 74 in a direction toward inner wall 148*a* of cavity 144 (FIG. 9). It is to be noted that as membrane 74 moves toward its distended configuration, it will closely conform to the shape of heat-expandable mass 70 resulting in a complete and controlled expelling of fluid from reservoir 144 through fluid outlet passageway 146 and into the infusion means 54 of the apparatus.

Figure 8:
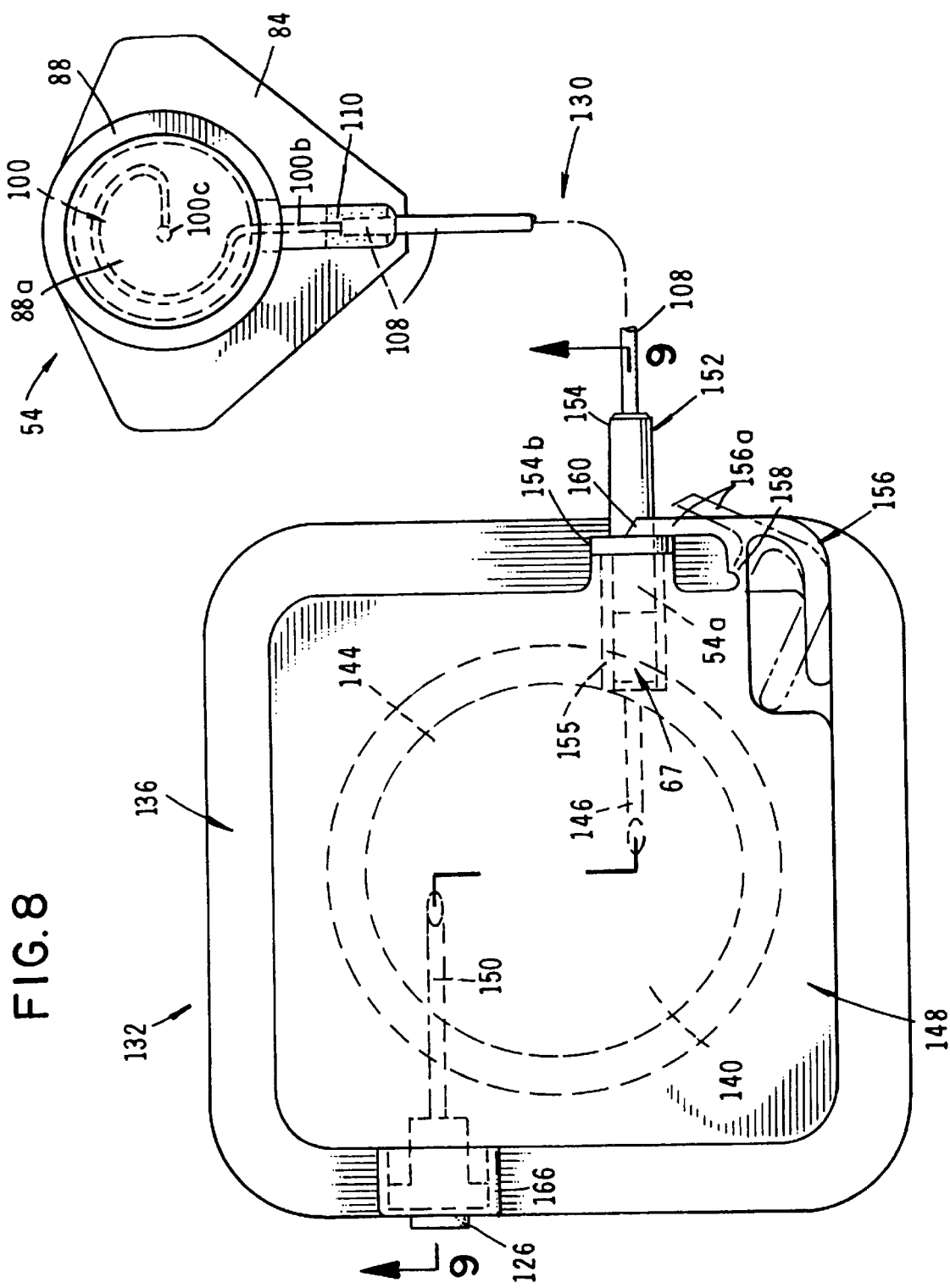
FIG. 8 is a top plan view of an alternate form of the fluid delivery apparatus of the invention.
Figure 12:
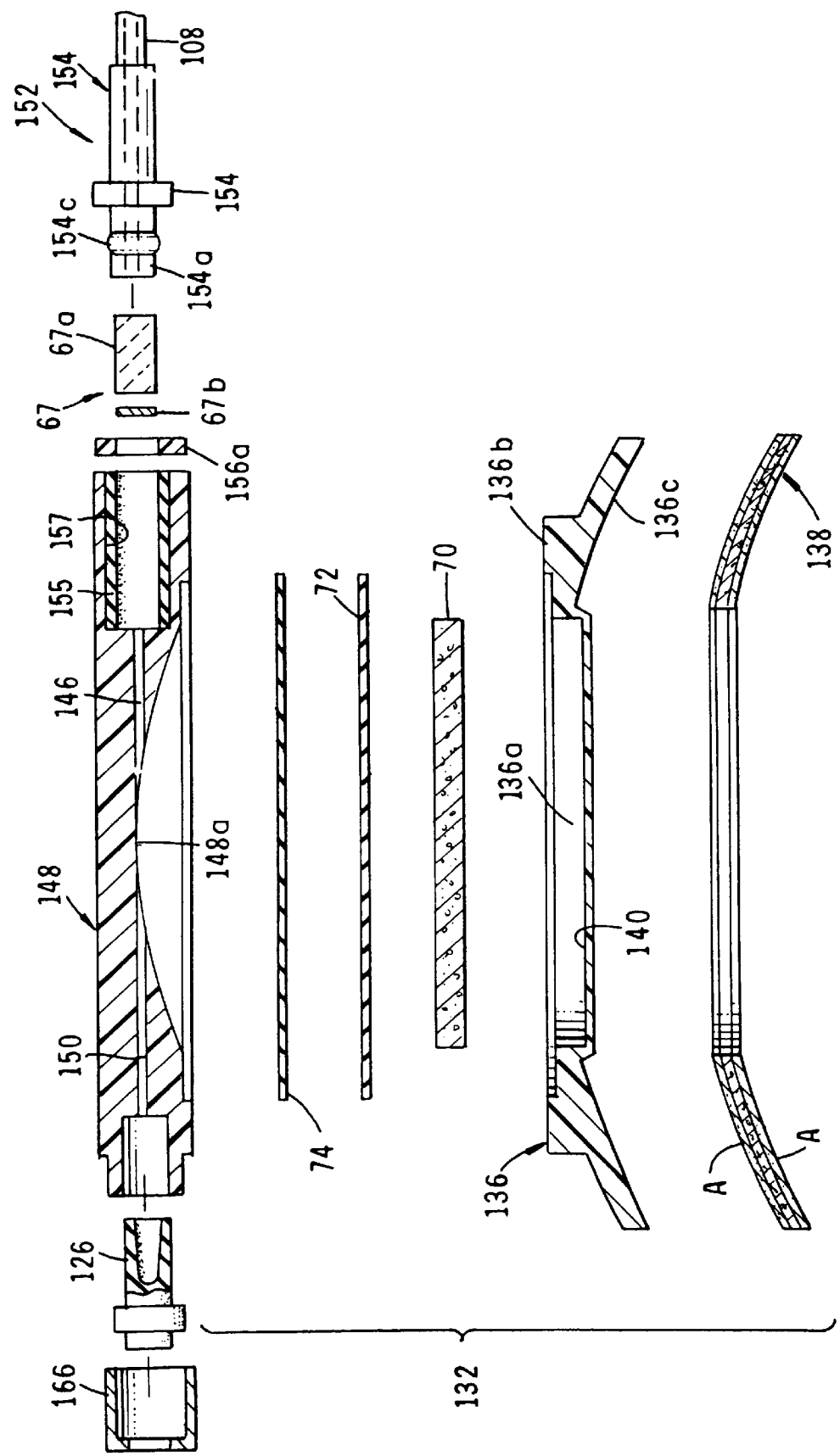
FIG. 12 is an enlarged, side-elevational, cross-sectional, exploded view of the apparatus shown in FIG. 9.

As shown in FIG. 8, a novel aspect of the apparatus of this latter form of the invention is the previously discussed infusion means or assembly 54. Assembly 54, which comprises a subcutaneous infusion device is of identical construction to that previously described and functions in an identical manner.

As best seen in FIGS. 8 and 10, the previously mentioned quick connect assembly 152 is of a slightly different construction from quick connect assembly 112. Assembly 152, enables quick interconnection of the infusion means and delivery tube 108 with cover 148 so that the delivery tube or administration line is placed in fluid communication with outlet fluid passageway 146. Quick connect assembly 152 here includes a body portion 154 having a hub 154*a* which is closely received within an elastomeric sleeve 155 carried within cover 148. Body portion 154 also includes an enlarged diameter flange 154*b*. Sleeve 155 is preferably formed of a co-molded elastomer which acts as a seal and hub 154*a* is provided with an enlarged diameter bead-like protuberance 154*c* (FIGS. 9 and 12) which sealably engages sleeve 155 to form a fluid tight seal. A locking member 156 functions to releasably maintain hub 154*a* seated within sleeve 155. Member 156 includes a centrally disposed, inwardly extending finger 158 (FIG. 10), which is either connected to, or integrally formed with, cover 148 in the manner shown in FIG. 10, to form a living hinge type construction. Formed proximate the inboard end 156*a* of locking member 156 is a locking collar 160 which lockably engages flange 154*b* of assembly 154. Provided proximate the opposite, or outboard, end 156*b* of the locking member is an inwardly extending actuating arm 162. When an inward force is imposed on arm 162, the locking member will pivot about finger 158 causing locking collar 160 to swing away from assembly 154 a sufficient distance to permit withdrawal of hub 154*a* from sleeve 155.

Using the fill means of the apparatus, reservoir 144 is filled with the beneficial agent to be infused into the patient. This fill means is of a similar construction to that described in connection with the embodiment of FIGS. 1 through 7 and includes an elastomeric septum 126 which comprises a non-coreable material that is held in position within cover 148 by a plastic septum cover 166 which is bonded to cover 148. As before, septum 126 is of standard construction and is penetrable by the cannula of a conventional type syringe which can be used to introduce into inlet passageway 150 and thence into reservoir 144 the beneficial agent or medicinal fluid which is to be infused into the patient.

With reservoir 144 thus filled, the infusion device 54 can be interconnected with the fluid storage device 132 through appropriate manipulation of the locking member 156 of the quick coupling mechanism. This done, the fluid storage device 132 can be interconnected with the patient in the same manner as previously described. As before, when the fluid storage device 132 is appropriately affixed to the patient's body, the patient's body temperature will cause heat expandable mass 70 to increase in volume causing the fluid contained within reservoir 144 to controllably flow under pressure toward outlet passageway 146. The fluid will then flow through a flow control means of the invention, which is housed within sleeve 155. In this regard, as best seen in FIG. 9, sleeve 155 is sealably disposed within a bore 157 formed in cover 148. The flow control means is of the character previously described and comprises a porous rate control member 67*a* and a filter 67*b* both of which are housed within sleeve 155 and both of which are in communication with delivery tube 108. With this construction, fluid flowing into outlet passageway 146 will flow through rate control assembly 67, into delivery tube 108 and then into the inlet of cannula 100. As before, rate control member 67*a* which is of the character previously described functions to regulate the rate of fluid flow toward delivery tube 108 and thence to the patient via the delivery cannula.

Figure 15:
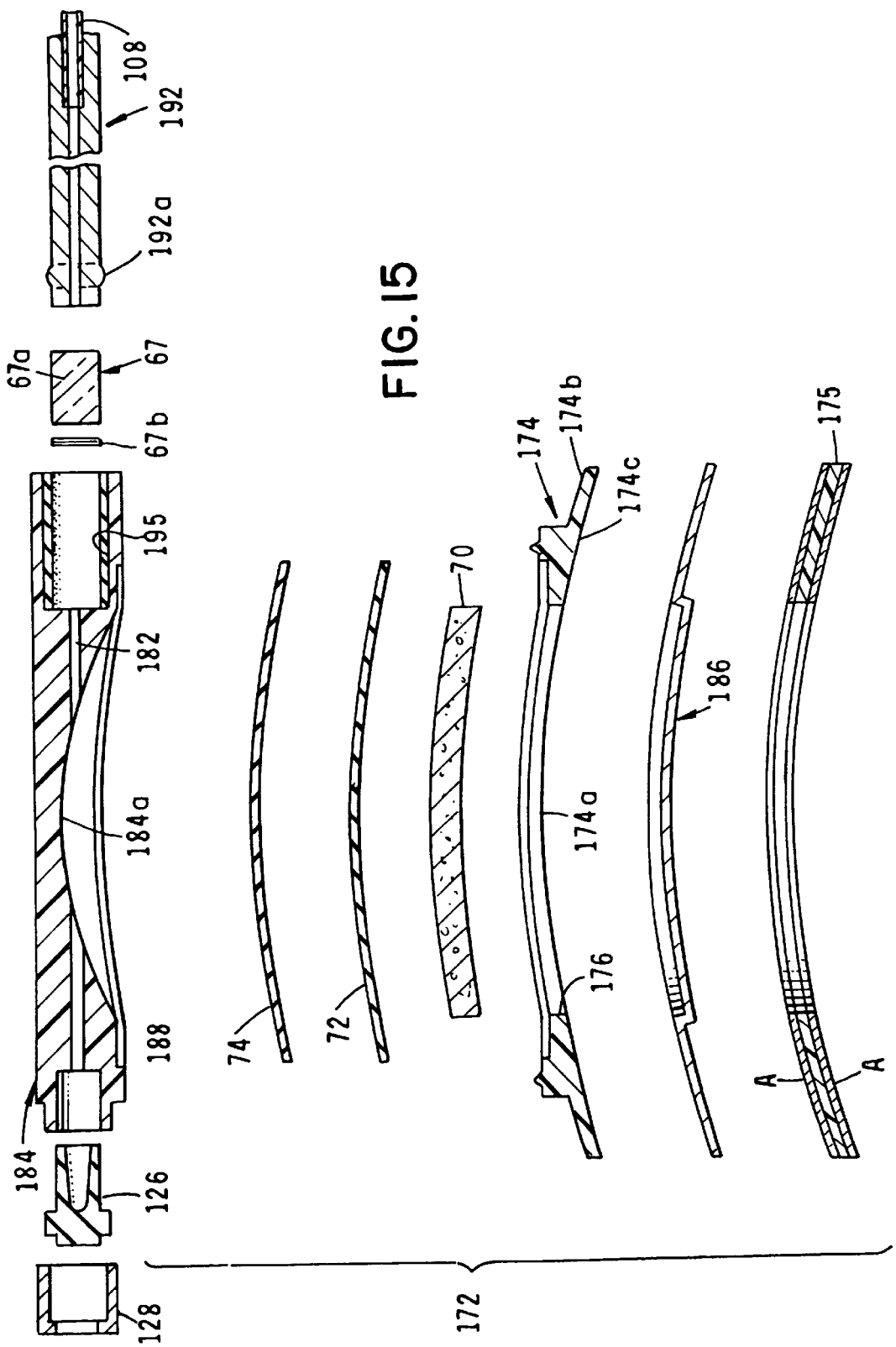
FIG. 15 is an enlarged, side-elevational, cross-sectional, exploded view of the device shown in FIG. 14.

Referring next to FIGS. 13 through 15, still another form of the apparatus of the invention is there shown and generally designated by the numeral 170. This alternate embodiment is quite similar to that shown in FIGS. 8 through 12 and once again like numerals are used in FIGS. 13 through 15 to identify like components. As best seen by referring to FIGS. 13 and 14, the apparatus here also comprises a low-profile, fluid-storage device 172 and a cooperating infusion means 54 for infusing the fluid stored in device 172 into the patient. Infusion means 54 is identical to that previously described in connection with FIGS. 1 through 7. However, fluid storage device 172 is of a slightly different construction in that it is designed to mate with a quick coupling mechanism of still a different, novel configuration.

Fluid storage device 172 here comprises a thin base 174 having a central portion 174a and peripheral portion 174b circumscribing central portion 174a. As before, base 174 is provided with a curved lower surface 174c of the character shown in FIGS. 9 and 14. When, surface 174c is positioned proximate the patient, the device can be taped or otherwise removably affixed to the patient using a foam adhesive tape 175 which has an adhesive "A" provided on both sides of the tape. Where appropriate peelable release liner can be provided over the lower surface of tape 175 to suitable protect the adhesive coating.

Formed within base 174 is a generally circular shaped opening 176 which receives a heat-expandable means of the character shown in FIG. 14. As before, this heat-expandable means functions to controllably force the fluids contained within the sealed reservoir 180 of the device (FIG. 14) to flow outwardly through an outlet passageway 182 formed in a cover 184 which is superimposed over base 174 in the manner shown in FIGS. 13 and 14. The heat-expandable means is of the character previously described herein and is held in position within opening 176 by a floor-like member 186 which is preferably insert molded to base 174. Member 186 may be is preferably constructed of a metal such as aluminum or stainless steel which can be stamped into the required configuration and can effectively function as a heat sink. The heat expandable means or mass is once again covered by a sealing means comprising a membrane 72 which is sealably connected to the peripheral portion 174b of base 174 by any suitable means such as thermal bonding in the manner indicated in FIG. 14. Overlaying membrane 72 and bonded to the cover by any suitable means is a distendable membrane 74 which, in cooperation with a generally concave-shaped cavity 184a formed in cover 184, forms fluid reservoir 180 (FIG. 14). Fill means of the same character described in connection with the earlier embodiments of the invention is provided for introducing fluids into reservoir 180 through a fluid inlet passageway 188 formed in cover 184.

When the fluid storage device 172 is affixed to the patient, the heat expandable means or mass 70 will be heated by the body heat of the patient and will controllably expand causing any fluid contained within the reservoir to flow outwardly thereof through outlet passageway 182. As before, when mass 70 expands, it will distend sealing membrane 72 and distendable membrane 74 in a direction toward inner wall 184a of cavity 180 (FIG. 14) and as the membranes move toward their distended configuration, they will closely conform to the resulting geometry of heat-expandable mass 70 causing in a complete and controlled expelling of fluid from reservoir 180 through fluid outlet passageway 182 and into the infusion means 54 of the apparatus.

As best seen in FIG. 13, a quick connect assembly 190 of a somewhat similar construction to quick connect assembly 112 is here provided. Once again, assembly 190, enables quick interconnection of the infusion means and administration line 108 with cover 184 so that the line is placed in fluid communication with outlet passageway 182. Quick connect assembly 190 includes a body portion 192 having an inboard end 192a which is closely received within a tubular member 194 which, in turn, is co-molded within a bore 195 formed in cover 184 (FIGS. 13 and 14). Formed in cover 184 are a pair of spaced apart locking notches 196 which are adapted to be lockably engaged by the specially configured, hook-like extremities of a pair of resiliently deformable locking arms 198 which are attached to body portion 192. Arms 198 include a pair of finger engaging portions 198a which can be squeezed together in a manner to spread the inboard ends of locking arms 198 apart a distance sufficient to permit the aforementioned hook-like extremities 198b to be removed from notches 196. As indicated in FIG. 13, hook-like extremities 198b are designed to securely grip notches 196 when inboard end 192 of body 190 of the quick connect coupler is seated within tubular member 194. However, when it is desired to separate the infusion set 54 from the storage device 172, an inward finger pressure exerted on arm portions 198a will spread hook-like extremities 198b a distance sufficient to permit removal of portion 192 from tubular member 194.

In using the apparatus of the present form of the invention, reservoir 180 is first filled with the beneficial agent to be infused into the patient using the fill means of the invention, As before, the fill means here comprises an elastomeric septum 126, which as shown in FIG. 14, is held in position within cover 184 by a clamping ring 128. Once again, septum 126 is of standard construction and is penetrable by a cannula "C" of a syringe of conventional construction. The conventional syringe (not shown) can be used to introduce fluid to be dispensed into inlet passageway 188 and thence into reservoir 180.

With reservoir 180 filled, either at the manufacturer, or in the manner described in the preceding paragraph, the infusion device can be interconnected with the fluid storage device 172 using the quick coupling mechanism in the manner described in the preceding paragraphs. This done, closure assembly 90 of the infusion device 54 (FIG. 7) is then separated from the base 84 and protective sheath 102 is slipped from end 100c of cannula 100 to permit the infusion device to be interconnected with the patient. When the fluid storage device 172 is next affixed to the patient's body, such as to an arm, leg, or abdomen the patient's body temperature will once again cause heat expandable mass 70 to expand thereby causing the fluid contained within reservoir 180 to controllably flow under pressure toward outlet passageway 182. The fluid entering outlet passageway 182 will flow through a fluid flow control means, shown here as the previously described porous rate control member 67, into delivery tube 108 and then into inlet 100e of cannula 100 (FIG. 13).

Figure 16:
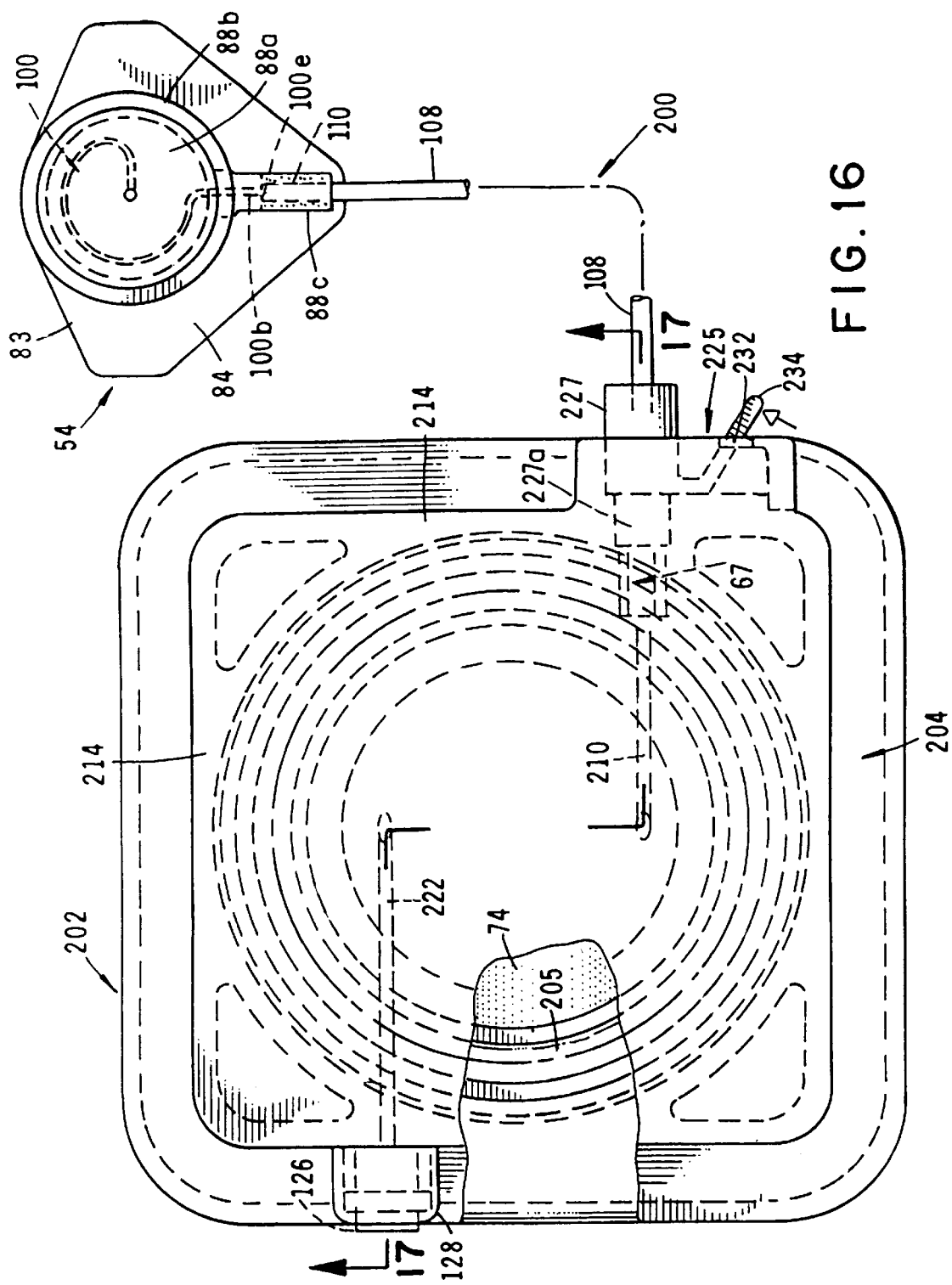
FIG. 16 is a top plan view of yet another of the fluid delivery apparatus of the invention.

Turning next to FIGS. 16 through 18, still another embodiment of the invention is there shown and generally designated by the numeral 200. This alternate embodiment is similar in many respects to that shown in FIGS. 13 through 15 and like numerals are used in FIGS. 16 through 18 to identify like components. As shown in FIGS. 16 and 17, the apparatus once again comprises a low-profile, ambulatory fluid-storage device 202 and a cooperating infusion means 54 for infusing the fluid stored in device 202 into the patient. Infusion means 54 is identical to that previously described in connection with FIGS. 1 through 7. The fluid storage device 202, on the other hand, is of a slightly different construction in that it includes a differently configured membrane 205 which overlays the heat expandable means of the invention. The fluid storage device 202 is also designed to mate with a quick coupling mechanism of a somewhat different design. Fluid storage device 202 here comprises a thin base 204 having a central portion 204a and peripheral portion 204b circumscribing central portion 204a. As before, base 204 is provided with a curved lower surface 204c of the character shown in FIGS. 17 and 18 so that when the lower peripheral portion of the base is disposed proximate the patient, the device can be conveniently taped or otherwise removably affixed to the patient, such as by using a double sided adhesive foam tape.

Formed within base 204 is a generally circular shaped opening 206 which closely receives a heat-expandable means which is of the character previously described. Once again, this heat-expandable means functions to controllably force the fluids "F" contained within the sealed reservoir 220 of the device (FIG. 17) to flow outwardly through an outlet passageway 210 formed in a cover 214 which is superimposed over and connected to base 204 in the manner shown in FIGS. 17 and 18. The heat-expandable means or mass 70 is held in position within opening 206 by floor-like member 209 which is connected to base 204. Member 209 is preferably constricted of metal such as aluminum, stainless steel or the like and functions as a heat sink.

In the present form of the invention, the heat expandable means or mass 70 is covered by a specially configured sealing means which here comprises a distendable membrane 205. Membrane 205 includes a peripheral sealing flange 205a which is sealably received within indexable grooves 217 formed in the peripheral portions of member 209 and cover 214. As best seen in FIG. 18, flange or bead 205a is generally circular in cross-section and grooves 217 cooperate to form a peripheral cavity which is also generally circular in cross-section. Bead 205a is preferably slightly larger than its receiving cavity so that, when held in compression between the cover and the base, a substantially leak-proof seal is formed.

Overlaying membrane 205 is a distendable drug barrier membrane 74 of the character previously described, which, in cooperation with a cavity 214a formed in cover 214, forms fluid reservoir 220 (FIG. 17). Fill means identical to that described in connection with the earlier embodiments of the invention is provided for introducing fluids into reservoir 220 through a fluid inlet passageway 222 formed in cover 214. As before, with this construction, as the heat expandable means or mass 70 is heated by the body heat of the patient via heat sink member 209, it will controllably expand causing any fluid contained within the reservoir to flow outwardly thereof through outlet passageway 210.

Operably coupled with device 202 is the previously discussed infusion means or assembly 54. Assembly 54, which comprises a subcutaneous infusion device is of identical construction to that previously described and functions in an identical manner. As best seen in FIG. 16, a quick connect assembly 225 of slightly different constriction enables quick interconnection of the infusion means and delivery tube 108 with cover 214 so that the delivery tube is placed in fluid communication with outlet passageway 210 and the flow control means. Quick connect assembly 225 here includes a body portion 227 having an inboard end 227a which is closely received within a stepped bore 230 formed in cover 214 (FIGS. 16 and 17). Formed on cover 214 is a locking gate 232 FIG. 16) which is adapted to lockably engage a resiliently deformable locking arm 234 which is, in turn, attached to body portion 227. With this construction, arm 234 can be urged inwardly toward body portion 227 a distance sufficient to permit the extremity of arm 234 to snap free of the locking gate and thereby permit removal of portion 227a from stepped bore 230. Locking gate 232 and arm 234 are of a conventional construction well understood by those skilled in the art.

In using the apparatus of this latest form of the invention, reservoir 220 is first filled with the beneficial agent to be infused into the patient using the fill means of the invention. The fill means here comprises an elastomeric septum 126, which is of substantially identical construction to that previously described and is held in position within cover 214 by a sonic, crush bonded ring 128. As before, a conventional syringe (not shown) can be used to introduce the fluid to be dispensed to the patient into inlet passageway 222 and thence into reservoir 220.

With reservoir 220 filled either at the manufacturer or in the manner described in the preceding paragraph, the infusion device can be interconnected with the fluid storage device 202 and infusion device 54 can be interconnected with the patient in the same manner as previously described herein. When the fluid storage device 202 is next affixed to the patient's body, the patient's body temperature will cause heat expandable mass 70 to expand thereby causing the fluid contained within reservoir 220 to controllably flow under pressure toward outlet passageway 210. The fluid entering outlet passageway 210 will flow through a fluid flow control means, shown here as the previously described filter 67b and porous rate control member 67a, into delivery tube 108 and then into inlet 100e of cannula 100 (FIG. 16).

Referring next to FIGS. 19 through 24, yet another form of the apparatus of the invention is there shown. This alternate form of the invention is somewhat similar to that shown in FIGS. 13 through 15 and like numerals are used in FIGS. 19 through 21 to identify like components. As best seen by referring to FIGS. 19, 20, and 21, the apparatus here comprises a low-profile, fluid-storage device 242 (FIG. 19) and a cooperating infusion means 54 (FIG. 21) for infusing the fluid stored in device 242 into the patient. Infusion means 54 is identical to that previously described. However, fluid storage device 242 is of a slightly different constriction in that it is designed to mate with a single lever arm type quick coupling mechanism 243 (FIG. 19).

Fluid storage device 242 here comprises a thin base 244 having a central portion 244a and peripheral portion 244b circumscribing central portion 244a. Base 244 is provided with a lower surface 244c of the character shown in FIGS. 20 and 21. As before, surface 244c is disposed proximate the patient when the device is taped or otherwise removably affixed to the patient, such as by using a pad 245 which may have an adhesive provided on both sides of the pad.

Formed within base 244 is a generally circular shaped cavity 246 which receives a heat-expandable means which, as before, functions to controllably force the fluids contained within the sealed reservoir 248 of the device (FIG. 20) to flow outwardly through an outlet 250 formed in a cover 252 which is superimposed over base 244 in the manner shown in FIGS. 20 and 23. The heat-expandable means is of the character previously described herein and is held in position within cavity 246 by a membrane 72 which is sealably connected to the peripheral portion 244b of base 244 in the manner indicated in FIG. 20. Overlaying membrane 72, which is of the character previously described, is a distendable membrane 249 which, in cooperation with a generally concave shaped cavity 252a (FIG. 22) formed in cover 252, forms fluid reservoir 248 (FIG. 20). Membrane 249 functions in substantially the same manner as previously discussed regarding membrane 74, but here comprises a laminate construction made up of two separate components 249a and 249b. For example, component 249a can be an elastomeric membrane, while component 249b can be a drug compatibility coating or a bonding membrane to enhance membrane bondability. Materials suitable for construction of components 294a and 294b include those materials which were previously discussed herein for use in the construction of membranes 72 and 74 as well as like elastomeric materials to which a suitable drug compatability coating and a suitable bonding membrane or coating can be affixed. Suitable drug compatibility coatings as well as suitable coatings to enhance membrane bonding are well known to those skilled in the art as are the methods for applying the coatings to the membranes.

With respect to membranes 72 and 249, ethylene-vinyl acetate comprises one material which is well suited for the construction of these membranes. Such material, known as "EVA" is commercially available from sources such as Toyo Soda Mfg. Co. and is sold by this company under the name and style NIPOFLEX. Other materials suitable for the construction of membranes 72 and 74 include thermoplastic rubber polymers and compounds sold by Shell Chemical Company under the name and style KRATON. Some of the characteristics of these polymers that make them attractive for the present application include dimensional stability, good vapor and gas transmission properties, ease of sterilization, chemical inertness and cleanliness. Still other material candidates for membranes 72 and 74 are various thermoplastic elastomers of the character available from Consolidated Polymer Technologies, Inc. of Largo, Fla. Fill means of the same character described in connection with the earlier embodiments of the invention is provided for introducing fluids into reservoir 248 through a fluid inlet 254 formed in cover 252 (FIGS. 19 and 23). As the heat expandable means or mass 70 is heated by the body heat of the patient, it will, as before, controllably expand causing fluids contained within the reservoir to flow outwardly thereof through outlet passageway 250 and thence into the infusion means 54 of the apparatus. As previously discussed, in the form of the invention shown in FIG. 22, mass 70 is encapsulated within a yieldably deformable covering 70c.

The cover 252 of this latest form of the invention can be constricted from various materials such as polypropylene, polyvinylidene, styrene and the like. Similarly, base 244 can be constructed from various metals and plastics. As before, where desired, medicament and instruction labels can be affixed to the cover 252 to identify the medicinal fluid contained within reservoir of the device.

The infusion means, or assembly 54 of the apparatus comprises a subcutaneous infusion device which is of identical construction and operation to that previously described and functions in an identical manner. However, assembly 54 is interconnected with fluid storage device 242 by means of a quick connect mechanism 243 which is of a somewhat different construction. Here mechanism 243 includes a body portion 259 having an inboard end 259a which is closely received within an elastomeric sleeve 260 which is mounted within a bore 262 formed in cover 252 (FIG. 23). In board end 259a includes a protuberance 259b which sealably engages sleeve 260 to form a fluid tight seal. Formed in cover 252 is a locking notch 264 which is adapted to be lockably engaged by a resiliently deformable locking arm 266 which is attached to body portion 259 by a living hinge connection 267. Arm 266 includes a finger engaging extremity 266a which can be urged inwardly toward body 259 in a manner to separate the inboard end of locking arm 266 from locking notch 264 by a distance sufficient to permit the hook-like extremity 266a formed on arm 266 to be separated from notch 264 thereby enabling separation of the infusion set 54 from the storage device 242.

The manner of use of the apparatus of this latest form of the invention, is virtually identical to that defined in connection with the earlier described embodiments, and therefore will not be discussed further at this time. Suffice to say that after the reservoir 248 is appropriately filled, the fluid delivery device 242 is operably connected to the infusion set 54 and the fluid storage device 242 is affixed to the patient's body, the patient's body temperature will cause heat expandable mass 70 to expand thereby causing the fluid contained within reservoir 248 to controllably flow under pressure toward outlet 250, through the previously described porous rate control member 67 and into delivery tube 108. The fluid will then flow into inlet 100e of cannula 100 for delivery to the patient (FIG. 21).

Figure 25:
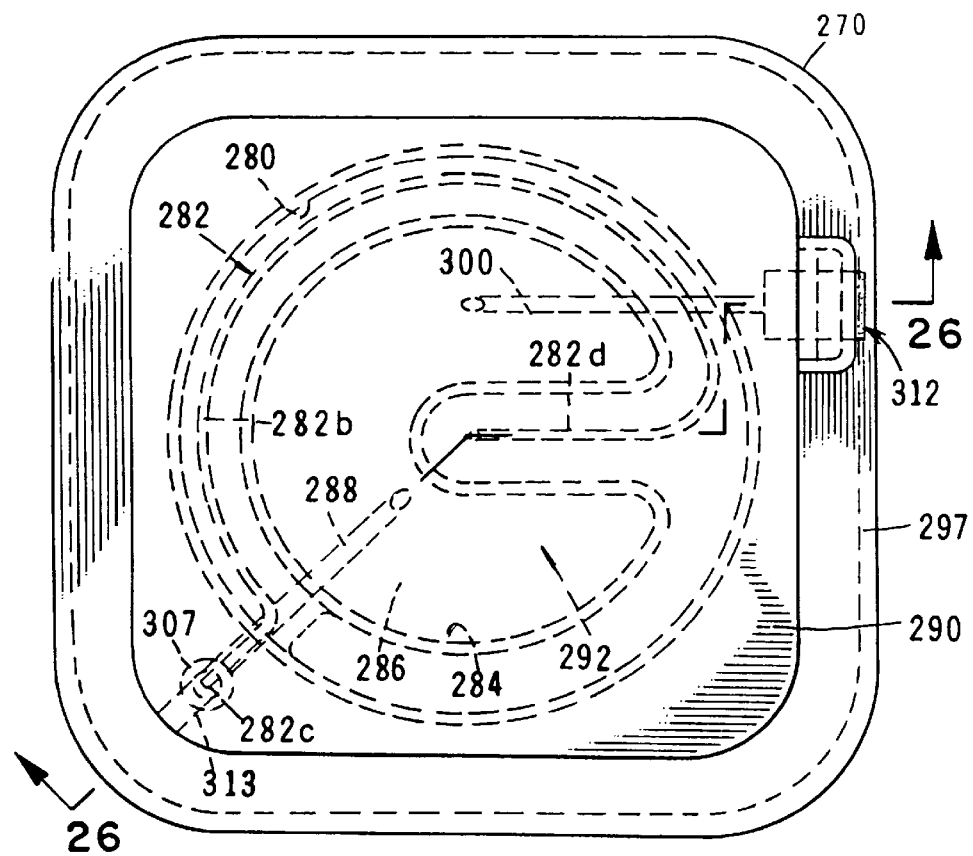
FIG. 25 is a top plan view of another form of the fluid delivery apparatus of the invention in which the delivery of fluid to the patient is accomplished through the use of a novel cannula subassembly carried by the base of the apparatus.
Figure 26:
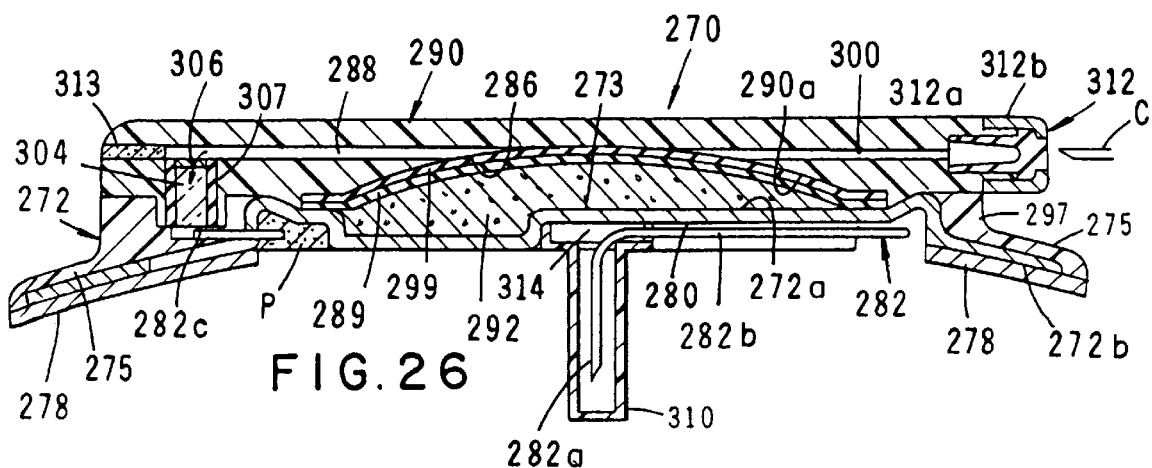
FIG. 26 is a cross-sectional view taken along lines 26—26 of FIG. 25.
Figure 29:
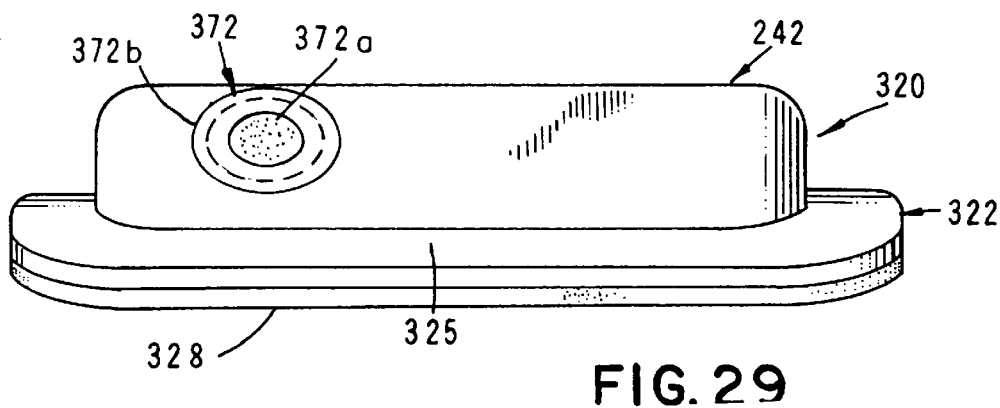
FIG. 29 is a side-elevational view of the apparatus shown in FIG. 25.
Figure 30:
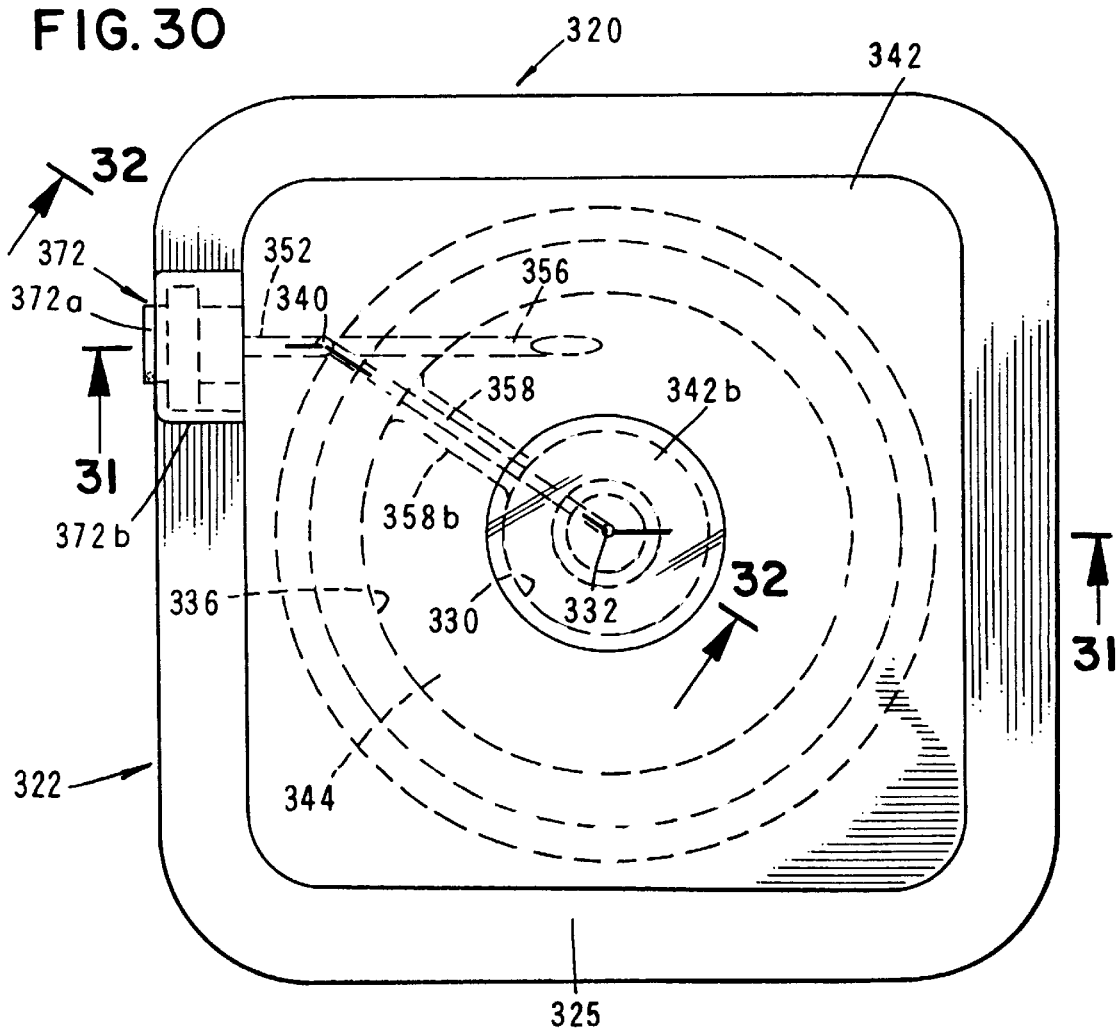
FIG. 30 is a top plan view of still another form of the fluid delivery apparatus of the invention.

Referring next to FIGS. 25 through 28, a quite different form of the apparatus of the invention for use in the infusion of medicinal fluids into a patient is there shown. As best seen by referring to FIGS. 25 and 26, this latest form of the invention comprises a low-profile, fluid delivery device 270 which incorporates as a part of the device an integral, rather than a separate, remotely disposed infusion means for infusing the fluid stored in the device into the patient. More particularly, as shown in FIGS. 26 and 27, fluid delivery device 270 includes a thin base assembly 272 having an upper surface 272a including a central portion 273 and peripheral portion 275 circumscribing central portion 273. Base 272 is also provided with a lower surface 272b which is disposed proximate the patient when the device is taped or otherwise removably affixed to the patient such as by a pad 278 having an adhesive on both sides of the pad.

Formed within base assembly 272 of this latest form of the invention is a cannula receiving channel 280 (FIGS. 25 and 28) within which the body portion of a novel spiral-like hollow cannula or capillary 282 is uniquely mounted in a manner presently to be described. Base 272 is also provided with a central, generally U-shaped cavity 284 formed in its upper surface 272a. Cavity 284 closely receives a specially shaped, heat-expandable means which, like the earlier described heat expandable means, functions to controllably expel the fluids contained within the sealed reservoir 286 of the device (FIG. 25). More particularly, as before, when the expandable means is heated by the body temperature of the patient, it will controllably increase in volume and, in so doing, will cause the medicinal fluid contained within the reservoir to flow outwardly through an outlet 288 formed in the cover 290 which is superimposed over and connected to base 272 (see FIGS. 26 and 27).

The heat expandable means is here provided in the form of a generally U-shaped member 292 which is disposed within cavity 284 in the manner best illustrated in FIG. 27. Member 292 here comprises a phase transition gel network having specific expansion characteristics when exposed to heat. Superimposed over cavity 284 and expandable member 292 is a sealing means for sealing cavity 284. This sealing means here comprises an elastomeric membrane 289 which is sealably connected to a strategically shaped floor 295 which forms a part of base assembly 272. Floor 295, which is preferably provided in the form of a metal stamping, is connected to an upper base member 297 which also forms a part of base assembly 272. With this construction, and for purposes presently to be described, floor 295 functions as an efficient heat sink. Overlaying membrane 289 is a distendable membrane 299 which, in cooperation with a generally concave shaped surface 290a formed on cover 290, forms the fluid reservoir 286 (FIG. 25). In a manner presently to be described, fill means are provided for introducing fluids into reservoir 286 through a fluid inlet 300 formed in cover 290 (FIGS. 25, 26 and 27). As member 292 is heated by the patient's body, it will controllably expand from the normal, relaxed configuration shown in FIG. 27 to the expanded configuration shown in FIG. 26. As heat expandable member 292 expands into the configuration shown in FIG. 26, it will distend sealing membrane 289 as well as distendable membrane 299 in a direction toward concave inner wall 290a of cover 290 (FIG. 26) and will cause the fluid contained within the fluid reservoir to flow outwardly through outlet 288. It is to be noted that as membrane 299 moves toward its distended configuration, it will closely conform to the shape of heat-expandable member 292 resulting in a complete and controlled expelling of fluid from reservoir 286 outwardly of the device through fluid outlet 288 and then into the infusion means, or cannula 282.

Once again, for a discussion of the various materials that can be used to construct base 272, cover 290, and membranes 289 and 299, reference should be made to U.S. Pat. No. 5,205,820 and to application Ser. No. 08/541,030 and to the discussion earlier set forth herein. The incorporated by reference patents also discuss in greater detail techniques for labeling and venting of the fluid delivery device.

Forming a unique aspect of this latest form of the apparatus of the invention is the novel infusion means for infusing medicinal fluids from fluid reservoir 286 into the patient. As shown in the drawings, the infusion means here forms an integral part of the fluid delivery device and is in direct communication with outlet 288. More particularly, the infusion means here comprises the previously identified circuitously shaped hollow cannula 282 as well as the earlier mentioned flow control means for controlling fluid flow into cannula 282. As best seen in FIG. 28, cannula 282 includes a piercing extremity 282a and a body portion 282b which is mounted within channel 280 in a novel manner presently to be described. The flow control means, which includes rate control means and cooperating filter means, here includes a porous rate control member 304 and a porous filter 306. As indicated in FIGS. 26 and 27, the flow control means is disposed between the outlet 288 of reservoir 286 and an inlet passageway 307 formed in the periphery of base 272. Cannula 282 includes an inlet end 282c which communicates with passageway 307 and also includes the previously mentioned outlet end 282a, which comprises a needle-like segment that extends generally perpendicularly downward from the lower surface of heat sink plate, or floor 295 for subdermal infusion of medicinal fluids into the patient. For this purpose, outlet end 282a is provided with a sharp, pointed extremity. To maintain the outlet end in a sterile condition, a protective sheath 310 is provided. Sheath 310 surrounds the outwardly extending cannula segment and is removably affixed to floor 295 of the base assembly in the manner shown in FIG. 26.

Filling of reservoir 286 is accomplished in the manner previously described by introducing fluid into the reservoir under pressure via a septum assembly 312 which is mounted in cover 290 (FIGS. 26 and 27). Septum assembly 312 includes a conventional elastomeric septum 312a and a deformable retaining ring 312b, both of which are of the general character previously described. During this fill step, the space between the upper surface of membrane 299 and the concave surface 290a of cover 290 is substantially filled with the fluid to be infused into the patient.

With the construction described in the preceding paragraphs, when the fluid is dispensed from the device as a result of the heating of expandable member 292, the member 292 will also function as a conformable ullage which, in cooperation with the distendable member 299 will, throughout the entire fluid delivery cycle, provide a constant fluid expelling pressure on the fluid contained within the reservoir, thereby avoiding undesirable delivery rate tail off at the end of the delivery period. This novel, substantially linear performance of the device enables it to meet even the most stringent medicinal fluid delivery requirements.

As best seen in FIG. 26, during the fluid delivery step, fluid will flow from reservoir 286 into passageway 288. A plug 313 provided in the outboard end of passageway directs fluid flow through the flow control means of the invention in the direction of the arrow of FIG. 26 and then into inlet end 282c of cannula 282. As before, the flow control means can be constructed from various porous materials including those described in Ser. No. 08/541,030 which is incorporated herein by reference. After flowing through the flow control means, the fluid will flow outwardly of the device via the hollow cannula 282.

Turning once again to FIG. 28, it is to be observed that part of the body portion 282b of spiral cannula 282 is uniquely supported within channel 280 of base assembly 272 by a cannula encapsulation means shown here as a standard potting compound "P". Compound "P" rigidly supports the body portion of the cannula within channel 280 and dynamically supports the outer extremity of the cannula body so that a spring-like extension 282d of the body portion is free to move three dimensionally within a hollow chamber 314 provided in the base assembly (FIG. 28). With this highly novel construction, when the device is connected to the patient using an adhesive coated pad 278 and with the needle portion 282a of the cannula penetrating the patient's body, as, for example, the patient's arm or leg, normal movement by the patient will permit the cannula to move within a portion of chamber 314 while the base components 295 and 297 remain completely stationary. Without this important feature, normal movements by the patient causing flexing of the muscle and tissue would impart loosening forces to the device which in time, could cause the adhesive pad 278, provided on the floor component 295 of the base to separate from the patient's skin. This important feature of the invention is discussed more fully in applicant Ser. No. 08/541,030 as are various other optional configurations of the spiral cannula 282.

Turning next to FIGS. 29 through 38, still another embodiment of the apparatus of the invention for use in the infusion of medicinal fluids into a patient are there shown. This latest form of the invention also comprises a low-profile, fluid delivery device generally identified by the numeral 320 which incorporates an integral, infusion means for infusing the fluid stored in the device into the patient. However, this latest embodiment of the invention also includes a novel fluid flow indicator means for indicating fluid flow from the device.

As illustrated in FIGS. 29, 30, 31, and 37, fluid delivery device 320 is of a substantially different configuration from the earlier described embodiments of the invention in that the heat expandable means is generally annular in shape. However, as before, the device includes a thin base assembly 322 having an upper surface 322a including a central portion 323 and peripheral portion 325 circumscribing central portion 323. Base 322 is also provided with a lower surface 322b which is located proximate the patient when the device is taped or otherwise removably affixed to the patient such as by a pad 328 having an adhesive "A" on at least the lower side of the pad.

Formed within base assembly 322 is a fluid delivery means receiving cavity 330 (FIGS. 31 and 32) within which the fluid delivery means of the invention for delivering medicinal fluids to the patient is received. Forming a part of the fluid delivery means is infusion means here shown as a hollow cannula or capillary 332 which is mounted within cavity 330 in a manner presently to be described. Base assembly 322 also has a central, generally annular-shaped cavity 336 which closely receives the previously mentioned, generally annular-shaped, heat-expandable means that functions to controllably expel the fluids contained within the sealed reservoir 338 of the device (FIG. 32). As will be discussed in greater detail hereinafter, when the heat expandable means is heated by the patient's body, it will cause the medicinal fluids contained within reservoir 338 to flow outwardly through an outlet 340 formed in the cover 342 which is superimposed over and connected to base assembly 322 in the manner shown in FIGS. 31 and 36).

The heat expandable means, which is here provided in the form of a generally annular-shaped temperature expandable member 344, is disposed within cavity 336 in the manner best illustrated in FIG. 36. Superimposed over cavity 336 and expandable member 344 is a sealing means for sealing cavity 336. This sealing means here comprises an elastomeric membrane 346 which is sealably connected to a generally circularly shaped floor 348 which forms a part of base assembly 322. Floor 348 circumscribes cavity 336 as well as fluid delivery means receiving cavity 320 in the manner shown in FIG. 36. Overlaying membrane 346 and connected to cover 342 (FIG. 33) is a second distendable membrane 350 which, in cooperation with a generally concave shaped surface 342a formed on cover 342, forms the fluid reservoir 338 (FIG. 32). As in the earlier-described embodiments, fill means are provided for introducing fluids into reservoir 338 through a fluid inlet 352 formed in cover 342 (FIG. 31).

Figure 31:
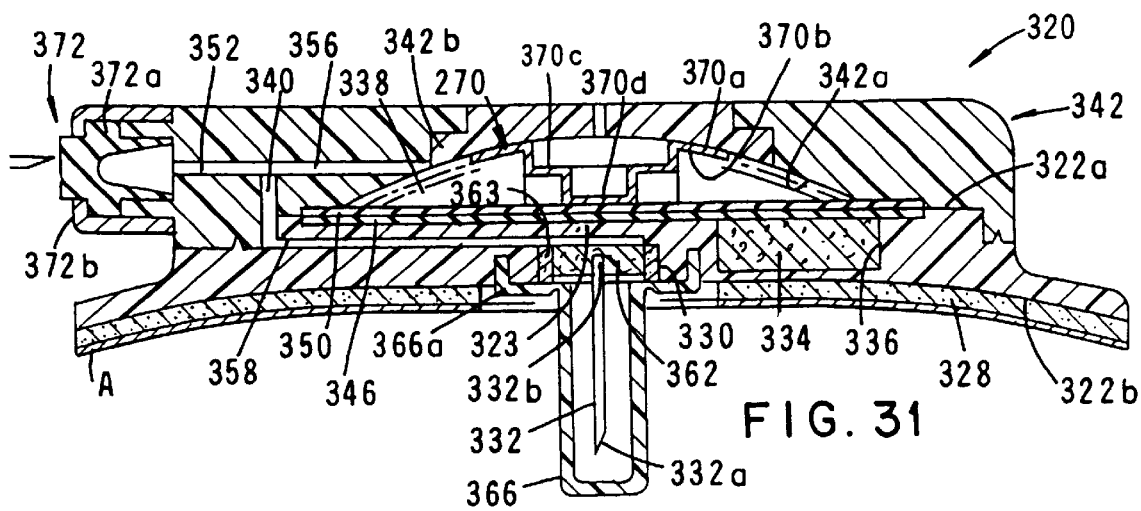
FIG. 31 is an enlarged, cross-sectional view taken along lines 31—31 of FIG. 30.
Figure 32:
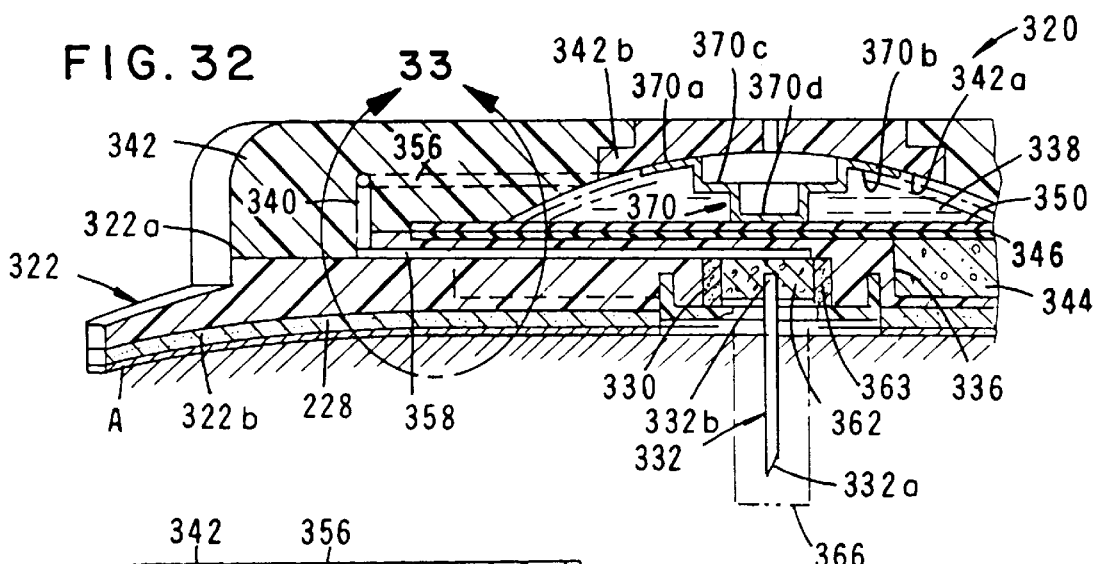
FIG. 32 is an enlarged, cross-sectional view taken along lines 32—32 of FIG. 30.
Figure 33:
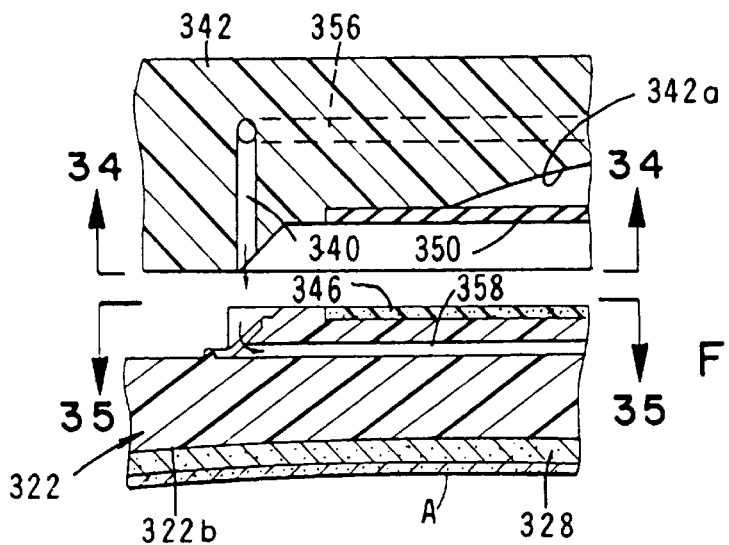
FIG. 33 is a fragmentary, cross-sectional view of the portion of the device identified in FIG. 32 by the numeral 33.

As member 344 is heated by the patient's body, it will controllably expand from the normal, relaxed configuration shown in FIGS. 31 and 32 into an expanded configuration. As heat expandable member 344 expands into the expanded configuration of increased volume, it will distend sealing membrane 346 as well as distendable membrane 350 in a direction toward concave inner wall 342a of cover 342 and will cause the fluid contained within the fluid reservoir to flow outwardly through a passageway 356 (FIG. 31). It is to be noted that passageway 356 is in communication with both passageways 340 and 352 and, therefore, can function both as an inlet to and an outlet from reservoir 338. As before as membrane 350 moves toward its distended configuration, it will closely conform to the shape of heat-expandable member 344 resulting in a complete and controlled expelling of fluid from reservoir 338. As fluid is forced from reservoir 338, it will flow into passageway 356, then into passageway 340 and finally into the infusion means, or cannula 332 via a passageway 358 formed in base assembly 322. Passageway 358 is formed within a radially extending protuberance 358a provided on base assembly 322 (FIG. 36) which protuberance extends through a gap 344a formed in expandable member 344. Once again, for a discussion of the various materials that can be used to construct base 322, cover 342, and membranes 346 and 350, reference should be made to U.S. Pat. No. 5,205,820 and to application Ser. No. 08/541,030. These disclosures also discuss in greater detail techniques for labeling and venting of the fluid delivery device.

Forming a unique aspect of this latest embodiment of the invention is the previously mentioned fluid delivery means for delivering medicinal fluids from fluid reservoir 338 into the patient. More particularly, the fluid delivery means here comprises the previously identified hollow cannula 332 as well as flow control means for controlling fluid flow into cannula 332 (see FIG. 38). As best seen in FIGS. 31 and 38, cannula 332 includes a piercing extremity 322a and an inboard inlet end 332b. The flow control means includes a rate control means comprising a porous rate control member 362 to which cannula 332 is connected as by laser welding. As indicated in FIGS. 31 and 32, the rate control means is disposed proximate outlet passageway 358 formed in base assembly 322. Cannula 332, along with rate control member 362, is held securely in position within cavity 330 in a potting compound 363 or by any suitable adhesive. In the instant form of the invention, cannula 332 extends generally perpendicularly downward from base assembly 322 for subdermal infusion of medicinal fluids into the patient. For this purpose, piercing extremity or outlet end 332a is provided with a sharp point and is maintained in a sterile condition by a tear away type protective sheath 366. As shown in FIGS. 31, 36, and 37, sheath 366 surrounds the outwardly extending cannula and is removably affixed to a collar 366a which is connected to base assembly 322 in the manner shown in FIG. 31.

Figures 31A, 31B, 31C:
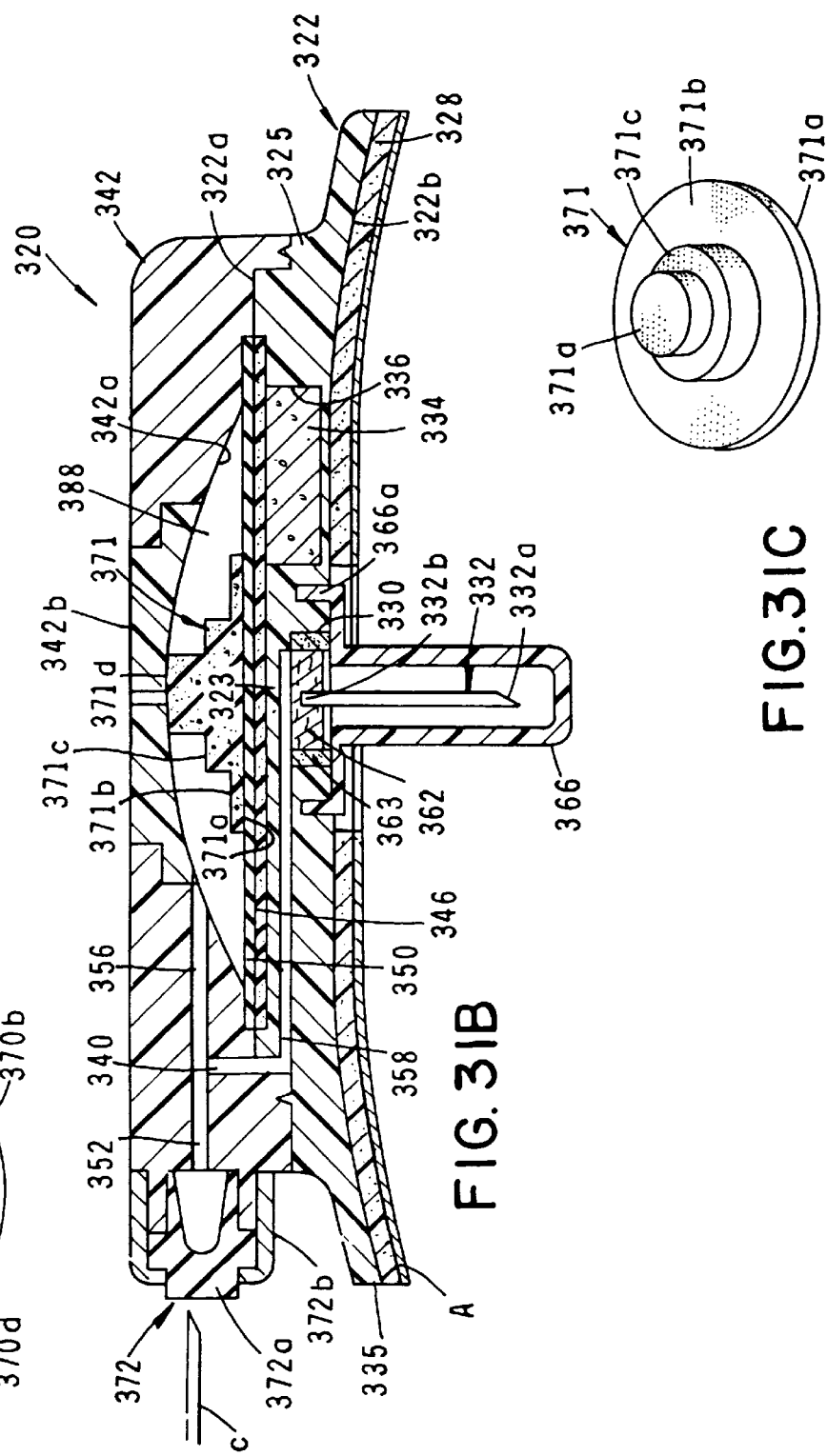
FIG. 31A is a generally perspective view of one form of the flow indicator element of the invention for indicating fluid flow from the reservoir of the device.
FIG. 31B is a cross-sectional view of a fluid delivery device similar to that shown in FIG. 31, but embodying a slightly different flow indicator element.
FIG. 31C is a generally perspective view of the flow indicator element shown in FIG. 31B.

A further novel aspect of the fluid delivery apparatus 320 of the invention is the provision of a flow indicator means for indicating fluid flow from reservoir 338. This flow indicator means is here provided in the form of a generally disk shaped indicator member 370 which is disposed within reservoir 338. As best seen in FIGS. 31 and 31A, member 370 includes a first surface 370a, a second surface 370b defined by a first stepped section, a third surface 370c defined by a second stepped section and a fourth surface 370d defined by a third stepped section. First surface 370a is of a first color, such as green; third surface 370c is of a second color, such as yellow; and fourth surface 370d is of a third color, such as red. For reasons presently to be described, disk shaped indicator member 370 is preferably formed of a yieldably deformable material, such as a sponge-like elastomer.

Centrally disposed within cover 342 is a clear or smoked plastic window element 342b. When reservoir 338 is appropriately filled, the sponge-like indicator member 370 is in a relaxed state as shown in FIG. 31 and surface 370a thereof is in engagement with window 342b. Thusly, the device displays through window 342b a green color indicating that the reservoir is filled. As heat distendable member 344 expands, indicator member 370 will be compressed to a degree such that surface 370c engages window 342b and in so doing will display a yellow color indicating that reservoir 388 is only partially full. Continued expansion of member 344 will cause still further compression of indicator member 370 to a degree that surface 370d of the member engages window 342b thereby showing a red color and indicating that reservoir 338 is empty.

Turning to FIGS. 31B and 31C, the same basic fluid delivery device as shown in FIGS. 31 through 35 is there illustrated and like numerals are used to identify like components. However, in this embodiment, a slightly different fluid flow indicator means is provided. This means, which is provided as a yieldably deformable, sponge-like member 371, is similar in construction to indicator member 370 in a slightly different manner.

As before the flow indicator means comprises a generally disk-shaped member which is disposed within reservoir 338. As best seen in FIG. 31B and 31C, member 371 includes a first surface 371a, a second surface 371b defined by a first stepped section, and a third surface 371c defined by a second stepped section, and a fourth surface 371d defined by a third stepped section. Second surface 371b is of a first color, such as red, third surface 371c is of a second color, such as yellow; and fourth surface 371d is of a third color such as green.

With the construction shown in FIGS. 31B and 31C, when reservoir 338 is filled, sponge indicator member 371 is in a relaxed state as shown in FIG. 31B and surface 371d is in engagement with window 342b so as to display a green indication that the reservoir is filled. As heat distendable member 344 expands, the indicator member will be compressed to a degree such that surface 371c engages window 342b and displays a yellow color indicating that reservoir 338 is only partially full. Continued expansion of member 344 will cause still further compression of indicator member 371 to a degree such that surface 371b thereof engages window 342b and reveals a red color indicating that reservoir 338 is empty.

Referring next to FIGS. 39 and 40, two alternate forms of fluid delivery means of the invention are shown. These fluid delivery means are similar in many respects to the fluid delivery means described in connection with FIGS. 29 through 38 and include a hollow delivery cannula for delivering fluid to the patient. However, in the fluid delivery means shown in FIG. 39, the hollow cannula 375 is provided with a flared inboard end 375a which communicates directly with the fluid reservoir of the device. Additionally, in this embodiment of the invention, the flow rate control member has been replaced with a stainless steel support collar 377 which is receivable within cavity 369 of the base assembly.

In the embodiment of the invention shown in FIG. 40, the cannula 379 is similar in configuration to cannula 375 in that it has a flared inlet end 379a. However, in this instance cannula 379 is supported within a porous rate control member 381 which is similar in character to rate control member 362.

Filling of reservoir 388 of the fluid storage device of this latest embodiment is accomplished in the manner previously described by introducing fluid into the reservoir under pressure via a filling means or septum assembly 372 which is mounted in cover 342 (FIGS. 31 and 36). Septum 372 includes a conventional elastomeric septum 372a and a deformable retaining ring 372b, both of which are of the general character previously described. During this fill step, the space between the upper surface of membrane 350 and the concave surface 342a of cover 342 is substantially filled with the fluid to be infused into the patient.

During the fluid delivery step, fluid will flow from reservoir 338 into passageway 356, into passageways 340 and 358 and then through the flow control means in a direction toward the inlet end 332b of cannula 332. After flowing through the flow control means, the fluid will flow outwardly of the device via the hollow cannula 332.

Figure 41:
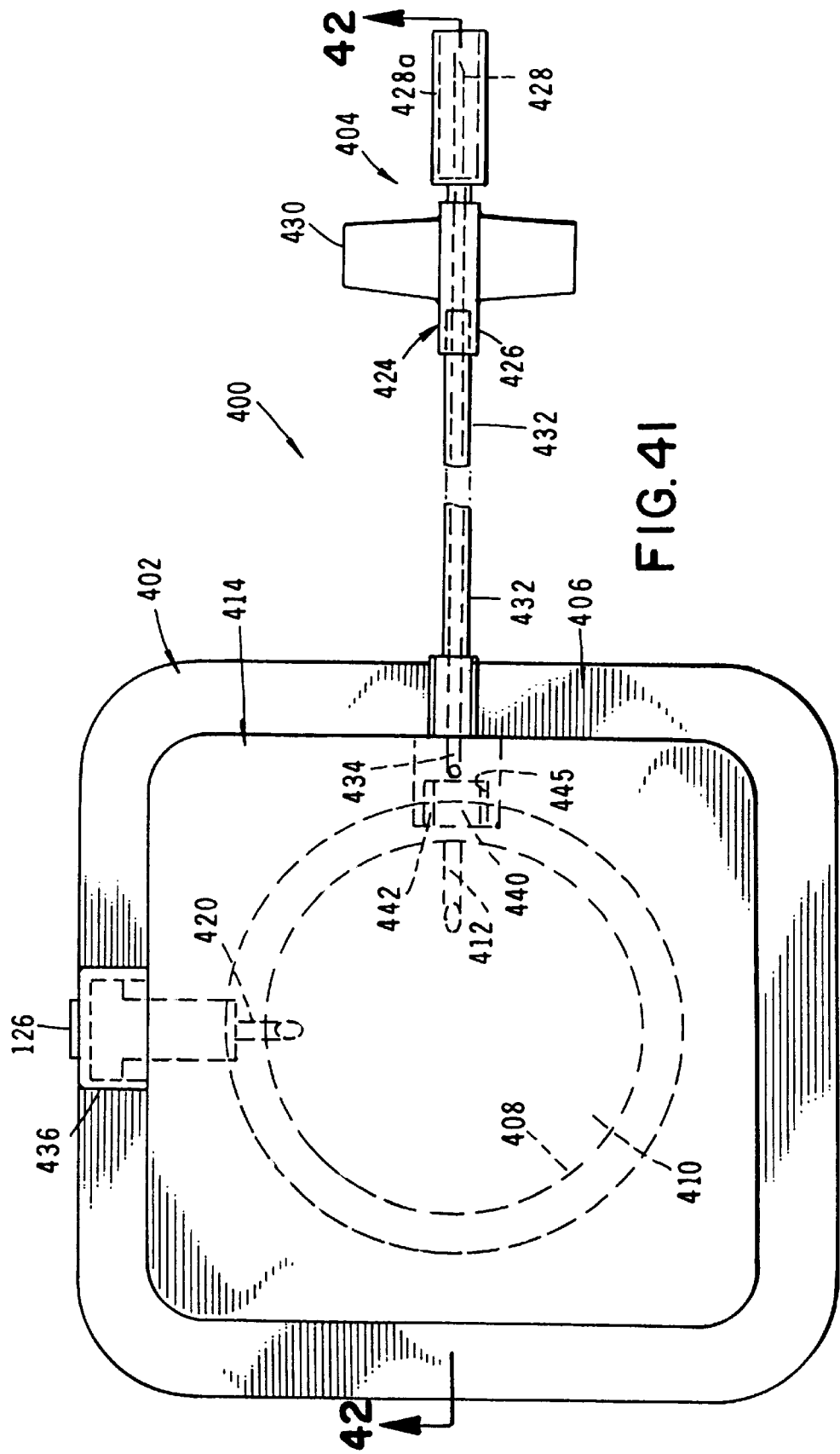
FIG. 41 is a top plan view of another form of the fluid delivery apparatus of the invention.

Referring next to FIGS. 41 through 42, still another form of the apparatus of the invention for use in the infusion of medicinal fluids into a patient is there shown and generally designated by the numeral 400. This alternate embodiment is similar in many respects to that shown in FIGS. 8 through 12 and like numerals are used in FIGS. 41 and 42 to identify like components. As shown in FIGS. 41 and 42, the apparatus here comprises a low-profile, fluid-storage device 402 and a cooperating infusion means 404 for infusing the fluid stored in device 402 into the patient. However, the infusion means 404 is of substantially different construction from that previously described in connection with FIGS. 8 through 12. Additionally, as will be apparent from the discussion which follows, the fluid storage device 402 is also of a somewhat different construction.

Fluid storage device 402, as before, comprises a thin base 406 having a curved lower surface 406a which is disposed proximate the patient when the device is taped or otherwise removably affixed to the patient. Formed within base 406 is a generally circular shaped chamber 408 (FIG. 42) within which the heat-expandable means is carried. This heat-expandable means is identical to that previously described and functions to controllably force the fluids contained within the sealed reservoir 410 of the device outwardly through an outlet passageway 412 formed in a cover 414 which is superimposed over and connected to base 406 in the manner best seen in FIG. 42. The heat-expandable means, or member 517 is covered by a sealing means which here comprises a single membrane 416 which is sealably connected to the peripheral portion of base 406 in the manner indicated in FIG. 42. In this embodiment of the invention, membrane 416 comprises a single distendable barrier membrane which take the place of the earlier described membranes 72 and 74. In cooperation with a surface 414a formed in cover 414, barrier membrane 416 forms the fluid reservoir 410 of the device. Fill means of the same character described in connection with the first embodiment of the invention are provided for introducing fluids into the reservoir 410 through a fluid inlet 420 formed in cover 414. As the heat expandable means or semi-solid mass 70 is heated by the body heat of the patient, it will controllably expand causing fluids contained within the reservoir to flow outwardly thereof through outlet passageway 412. When mass 70 expands, it will distend barrier membrane 416 in a direction toward a concave surface 414a formed in cover 414 (FIG. 42). As barrier membrane 416 moves toward its distended configuration, it will closely conform to the shape of heat-expandable mass 70 resulting in a complete and controlled expelling of fluid from reservoir 410 through fluid outlet passageway 412 and into the infusion means 404 of the apparatus.

As shown in FIG. 46, a novel aspect of the apparatus of this latter form of the invention is the previously mentioned intravenous infusion means or assembly 404. Assembly 404 comprises an intravenous needle assembly 424 which includes a needle support 426 and a hollow needle 428 supported thereby. Connected to support 426 is a conventional butterfly assembly 430 for use in affixing the needle assembly to the patient. A breakaway needle cover 428a surrounds and protects needle 428. An elongated administration line 432 interconnects the needle assembly with the fluid delivery device and functions to place reservoir 410 in communication with hollow needle 428 via a flow control means and a stub outlet passageway 434 (FIG. 42).

In using the apparatus of this latest form of the invention, reservoir 144 is filled with the beneficial agent to be infused into the patient using the fill means of the invention. This fill means is of a similar constriction to that described in connection with the embodiment of FIGS. 1 through 7 and includes a septum 126 which comprises a non-corable material. Septum 126 is held in position within cover 414 by a plastic septum cover 436 which is bonded to cover 414. As before, septum 126 is of standard construction and is penetrable by a cannula of a conventional type syringe which can be used to introduce beneficial agents into inlet passageway 420 and thence into reservoir 414.

With reservoir 410 filled in the manner described, and with the infusion device interconnected with the fluid storage device 402 in the manner shown in FIGS. 41 and 42, the fluid storage device 402 can be affixed to the patient. When so affixed, the patient's body temperature will cause heat expandable mass 517 to expand causing the fluid contained within reservoir 410 to controllably flow under pressure toward outlet passageway 412, through the flow control means and into stub passageway 434. The flow control means is of the character previously described and comprises a porous rate control member 440 and a filter 442 both of which are housed within a sleeve 444 disposed within a bore 445 formed in cover 414. With the construction shown in the drawings, fluid flowing into outlet passageway 412 will flow through filter 442, through rate control assembly 440, into stub passageway 434, into administration line 432 and then into the inlet of hollow cannula 428.

Turning next to FIGS. 41 through 44, yet another form of the apparatus of the invention for use in the infusion of medicinal fluids into a patient is there shown and generally designated by the numeral 450. This alternate embodiment is similar in many respects to that shown in FIGS. 41 through 42 and like numerals are used in FIGS. 43 through 47 to identify like components. As shown in FIGS. 43 and 44, the apparatus here comprises a low-profile, fluid-storage device which is substantially identical to fluid storage device 402. Coupled with the fluid storage device is a cooperating infusion means which is of somewhat similar construction to infusion means 404. However, in this latest embodiment, the cannula portion of the infusion means rather than being remotely located, is integrally formed with the fluid storage device.

Fluid storage device 452, as before, comprises a thin base 454 having a curved lower surface 454a which is disposed proximate the patient when the device is taped or otherwise removably affixed to the patient. Formed within base 454 is a generally circular shaped chamber 456 within which the heat-expandable means is carried. This heat-expandable means is identical to that previously described and functions to controllably force the fluids contained within the sealed reservoir 458 of the device to flow outwardly through an outlet passageway 460 formed in a cover 464. As before, cover 464 is superimposed over and connected to base 454 in the manner best seen in FIG. 44. The heat-expandable means, or gel network member 70 is covered by a sealing means which here comprises a distended membrane 466 which is sealably connected to the peripheral portion of base 454 in the manner indicated in FIG. 44. In this embodiment of the invention, a second distendable membrane 468 overlays membrane 466 and is affixed to a cover 464. In cooperation with a surface 464a formed in cover 464 in the manner shown in the drawings, membrane 468 forms the fluid reservoir 458 of the device.

Fill means of the same character described in connection with the first embodiment of the invention are provided for introducing fluids into the reservoir 458, through a fluid inlet 472 formed in cover 464. As the heat expandable means or semi-solid mass 70 is heated by the body heat of the patient, it will controllably expand causing any fluid contained within the reservoir to flow outwardly thereof through outlet passageway 460. When mass 70 expands, it will distend membranes 466 and 468 in a direction toward a surface 464a formed in cover 464 (FIG. 44). As barrier membrane 466 moves toward its distended configuration, it will closely conform to the shape of heat-expandable mass 70 resulting in a complete and controlled expelling of fluid from reservoir 458 through fluid outlet passageway 460 and into the infusion means of the apparatus.

As shown in FIGS. 43 and 44, a novel aspect of the apparatus of this latter form of the invention is the previously mentioned intravenous infusion means, which is shown here as an infusion assembly 476. Assembly 476 comprises an intravenous needle assembly 480 which includes a needle support 482 and a hollow needle 484 supported thereby. As best seen in FIG. 44, needle support 482 is connected directly to cover 464. Connected to support 482 is a conventional butterfly assembly 430 of the character previously described for use in affixing the needle assembly to the patient. As indicated in the drawings, the elongated administration line shown in FIGS. 41 and 42 has been eliminated and support 482 functions to place reservoir 458 in communication with hollow needle 484 via a different type of flow control means, the character of which will presently be described.

In using the apparatus of this latest form of the invention, reservoir 458 is filled with the beneficial agent to be infused into the patient using the fill means of the invention. This fill means is of identical construction to that described in connection with the embodiment of FIGS. 41 through 42 and includes a septum 126 which comprises a non-corable material and which is held in position within cover 464 by a plastic septum cover 436 which is bonded to cover 464.

With reservoir 458 appropriately filled and with the fluid delivery device interconnected with the patient in a manner such that cannula 484 pierces the patient's vein. The patient's body temperature will cause heat expandable mass 70 to expand causing the fluid contained within reservoir 458 to controllably flow under pressure toward outlet passageway 460 through the flow control means and into passageway 482a of support 482. The flow control means of this latest form of the invention comprises a novel rate control member 487 which is housed within a bore 489 formed in cover 464 (FIGS. 44 and 45). As best seen in FIGS. 46 and 47, member 487 is provided with a precision drilled microbore 491 which is in communication with fluid passageways 460 and 482a. With this constriction, fluid flowing into outlet passageway 460 will flow through microbore 491 which comprises the rate control means of the invention, into passageway 482a and then into the inlet of hollow cannula 484. It is, of course, apparent that by carefully controlling the size of microbore 491, the rate of fluid flow toward the infusion means can be precisely controlled.

Figure 49:
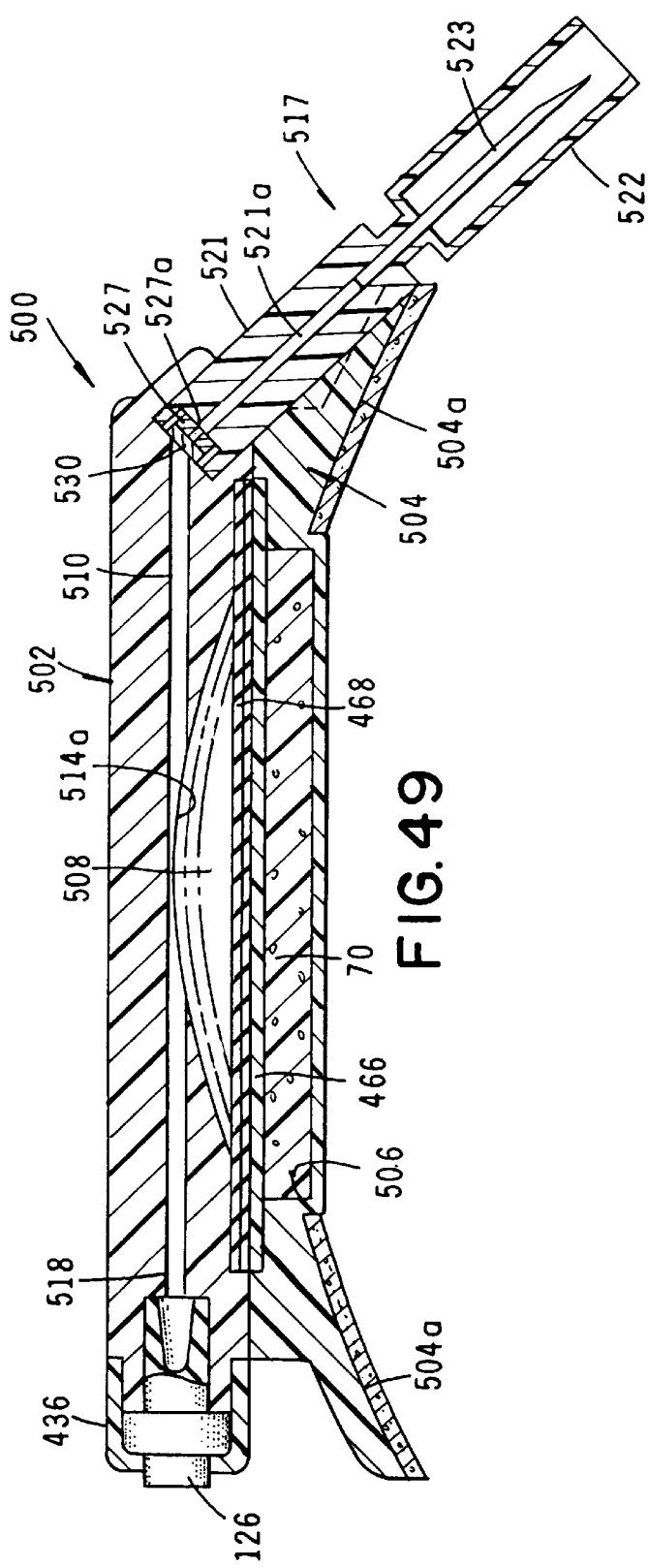
FIG. 49 is an enlarged, cross-sectional view taken along lines 49—49 of FIG. 48.

Turning to FIGS. 48 through 52, still another form of the apparatus of the invention for use in the infusion of medicinal fluids into a patient is there shown and generally designated by the numeral 500. This alternate embodiment is similar in many respects to that shown in FIGS. 43 through 47 and, once again, like numerals are used to identify like components. As shown in FIGS. 48 and 49, the apparatus here comprises a low-profile, fluid-storage device which is substantially identical to the fluid storage device just described. Once again, in this latest embodiment, the cannula portion of the infusion means is integrally formed with the fluid storage device.

Fluid storage device 502 comprises a thin base 504 having a curved lower surface 504a which is disposed proximate the patient when the device is taped or otherwise removably affixed to the patient. Formed within base 504 is a generally circular shaped chamber 506 within which the heat-expandable means is carried. This heat-expandable means is somewhat different from that previously described, but still functions to controllably force the fluids contained within the sealed reservoir 508 of the device outwardly through an outlet passageway formed in a cover 514 which is superimposed over and connected to base 504 in the manner best seen in FIG. 49. The heat-expandable means of this latest form of the invention, uniquely permits precise multi-rate staged delivery of fluid to the patient. The heat expandable means, or member 70, is covered by a sealing means which here comprises a distendable membrane 466 which is sealably connected to the peripheral portion of base 504 in the manner indicated in FIG. 49. In this latest embodiment of the invention a second distendable membrane 468 overlays membrane 466 and is affixed to cover 514. In cooperation with a curved surface 514a formed in cover 514 membrane 468 forms the fluid reservoir 508 of the device. Fill means of the same character described in connection with the first embodiment of the invention are provided for introducing fluids into the reservoir 508, through a fluid inlet 518 formed in cover 514. As the heat expandable means or semi-solid mass 70 is heated by the body heat of the patient, it will controllably expand causing any fluid contained within the reservoir to flow outwardly thereof through outlet passageway 510. When mass 70 expands, it will distend membranes 466 and 468 in a direction toward curved surface 514a which is formed in cover 514 (FIG. 49). As barrier membrane 466 moves toward its distended configuration due to the urging of expanding mass 70 fluid within reservoir 508 will be forced through fluid outlet passageway 510 and then into the infusion means 517 of the apparatus.

As shown in FIGS. 48 and 49, a novel aspect of the apparatus of this latter form of the invention is the previously mentioned intravenous infusion means which is shown here as an infusion assembly 517. Assembly 517 comprises an intravenous needle assembly 523 which includes a needle support 521 and a hollow needle 523 supported thereby. As best seen in FIG. 49, needle support 521 is connected directly to cover 514 but here extends angularly downward with respect to base 504. Once again, the administration line shown in FIGS. 41 and 42 has been eliminated and support 521 functions to place reservoir 508 in direct communication with hollow needle 523 via yet a different type of flow control means, the character of which will presently be described.

In using the apparatus of this latest form of the invention, reservoir 508 is filled using a fill means of identical construction to that described in connection with the embodiment of FIGS. 13 through 15. With reservoir 508 appropriately filled, and with a protective sheath 522 which covers needle 523 removed, the fluid delivery device can be interconnected with the patient in a manner such that cannula 523 pierces the patient's vein. Once the fluid delivery device is in position, the patient's body heat will cause heat expandable mass 70 to expand causing the fluid contained within reservoir 508 to controllably flow under pressure toward outlet passageway 510 through the flow control means and into passageway 521a of support 521. The flow control means of this latest form of the invention, uniquely comprises a novel, disk-like porous rate control member 527 having a central aperture 527a. Member 529 is housed within a bore 529 formed in cover 514 (FIG. 51) and is in fluid communication with fluid passageway 510 in the manner shown in the drawings. With this construction, fluid flowing into outlet passageway 460 will flow through a filter 530, through rate control member 527, and then into the inlet of hollow cannula 523. It is, of course, apparent that by carefully controlling the porosity of member 527 as well as the size of aperture 527a, the rate of fluid flow toward the infusion means can be precisely controlled.

Figure 52:
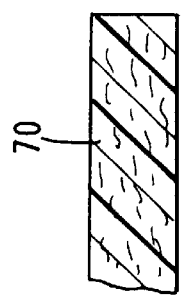
FIG. 52 is a greatly enlarged, fragmentary cross-sectional view of the heat expandable means of this latest form of the invention.

Referring particularly to FIG. 52, the heat expandable means there shown comprises a blend of two or more phase-transition gels of the character described in incorporated by reference U.S. Pat. Nos. 4,732,930 and 5,403,893. This blend can be precisely tailored to provide differential expansions of the gel blend over time and thereby permit patterned delivery of the beneficial agent to the patient via the infusion means. With this unique construction, the ratio of the blend components and the individual expansion rates thereof can be selected to achieve the desired multi-rate delivery protocol.

Figure 52A:
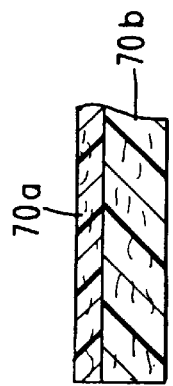
FIG. 52A is a greatly enlarged, fragmentary, cross-sectional view of an alternate form of the heat expandable means of the invention.
Figure 51:
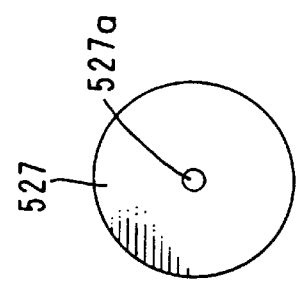
FIG. 51 is an enlarged, cross-sectional view taken along lines 51—51 of FIG. 50.
Figure 50:
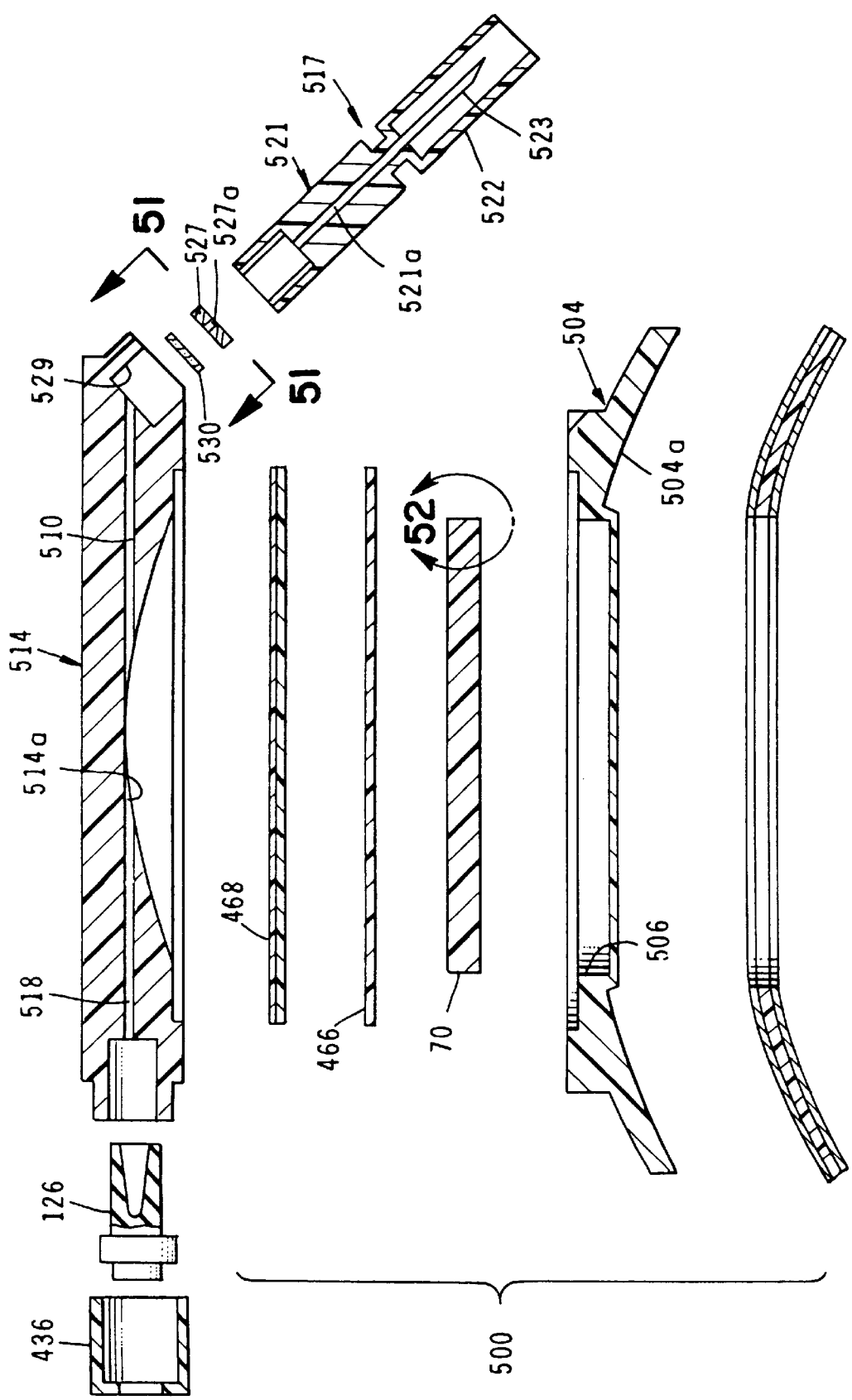
FIG. 50 is a side-elevational, cross-sectional, exploded view of the apparatus shown in FIG. 49.

Turning to FIG. 52A, the heat expandable means there shown comprises a laminate construction made up of two precisely formulated phase-transition gels 70a and 70b, each having different expansion characteristics over time. The respective thickness of the individual laminates 70a and 70b and the specific gel characteristics of each laminate can be specially tailored in a manner to achieve various multi-rate delivery protocols.

The phase transition gels 70a and 70b are preferably responsive gel networks, that is networks that are capable of incorporating a non-aqueous reactive material into the interstitial spaces of the network with an accompanying three-dimensional increase in gel volume. The gel networks are responsive to heat and can be made to expand or contract in volume by factors as large as several hundred.

Turning now to FIGS. 53 through 63, yet another form of the apparatus of the invention is there shown and generally designated by the numeral 550. This alternate embodiment is somewhat similar to those earlier discussed herein and, once again, like numerals are used in FIGS. 53 through 63 to identify like components. However, in sharp contradistinction to the earlier embodiments of the invention, this latest apparatus includes a novel fluid storage device having a fluid reservoir which can be filled either by a septum assembly or through use of a specially designed fluid container or vial fill subassembly of a character presently to be described.

Figure 53:
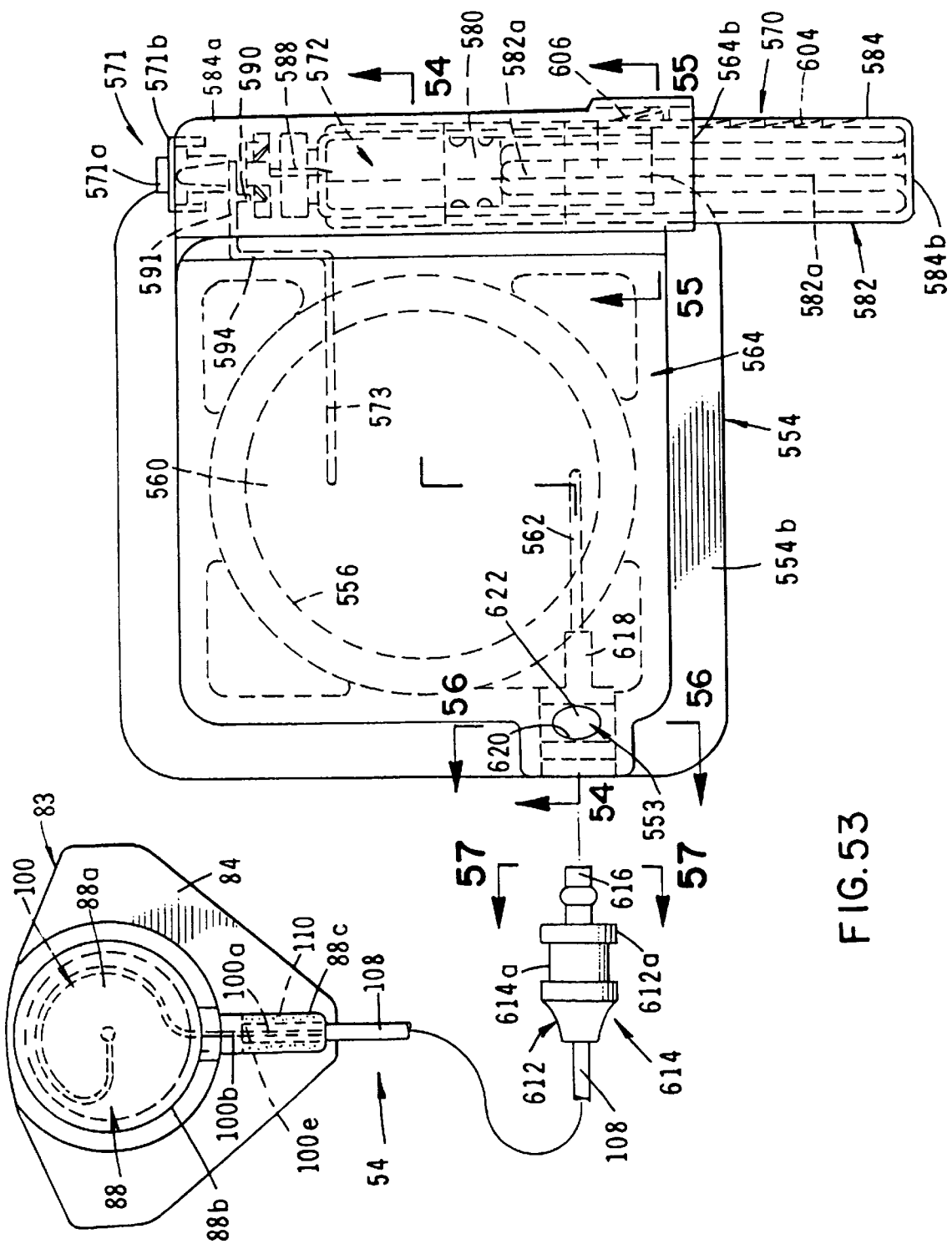
FIG. 53 is a top plan view of still another embodiment of the fluid delivery apparatus of the invention.
Figure 59:
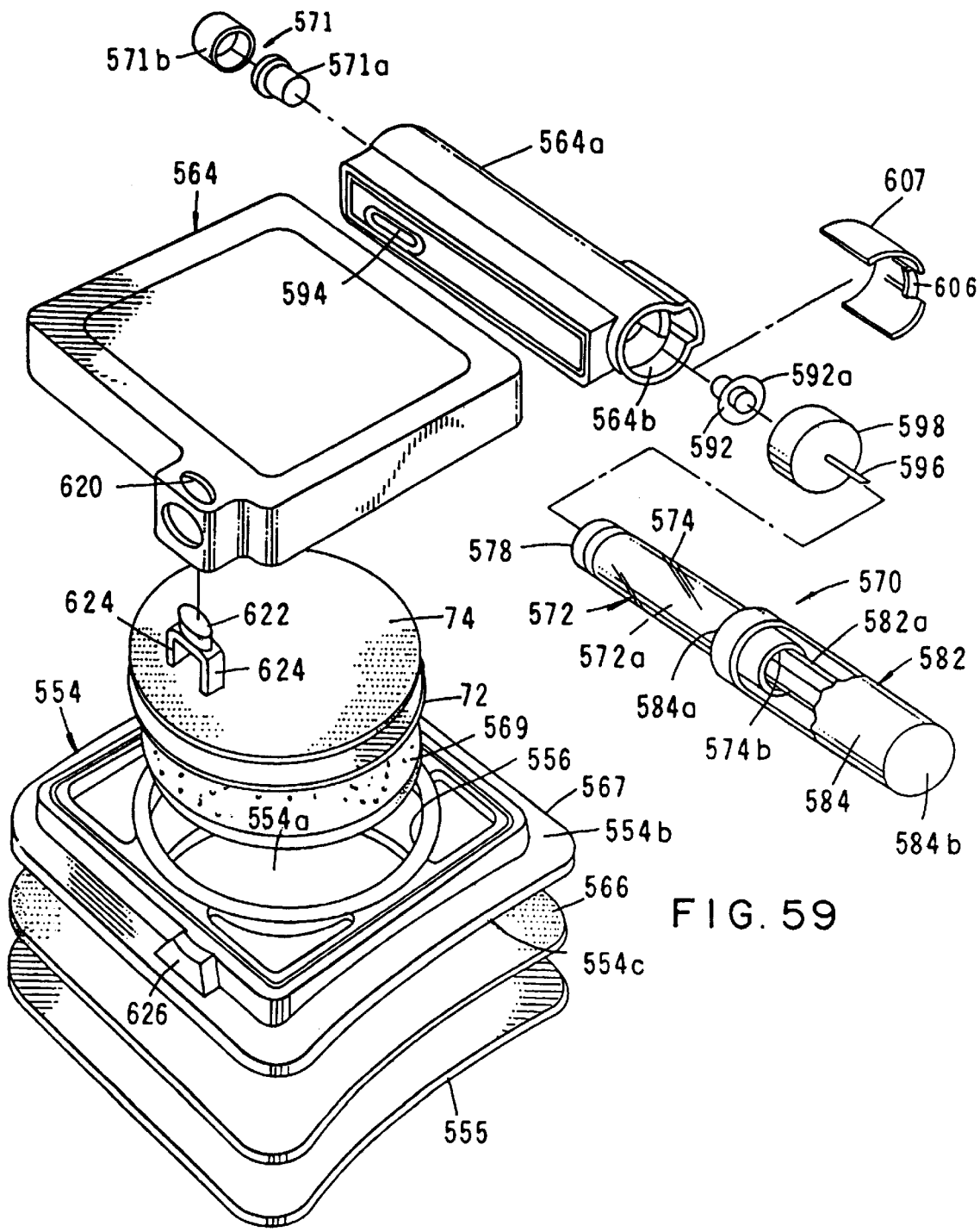
FIG. 59 is a generally perspective, exploded view of the apparatus shown in FIG. 53.

As best seen by referring to FIGS. 53, 54, and 59, the apparatus here comprises a low-profile, fluid-storage device 552 and a remotely located cooperating infusion means 54 for infusing the fluid stored in device 552 into the patient. Infusion means 54 is identical to that previously described in connection with FIGS. 1 through 7. The fluid storage device 552, on the other hand, is of quite a different construction in that it includes not only the previously mentioned vial fill feature, but also is designed to mate with a quick coupling mechanism of a different design, which is releasably connected to the fluid storage device by a push button type capture and release assembly 553.

Fluid storage device 552 here comprises a thin base assembly 554 having a central portion 554a and peripheral portion 554b circumscribing central portion 554a. As before, base assembly 554 is provided with a curved lower surface 554c of the character best seen in FIGS. 54 and 59. In use, surface 554c is disposed proximate the patient so that the device can be taped or otherwise removably affixed to the patient in the manner previously described.

Formed within base assembly 554 is a generally circular shaped opening 556 which receives a heat-expandable means of the general character previously described. As before, this heat-expandable means functions to controllably force the fluids contained within the sealed reservoir 560 of the device (FIG. 54) outwardly through an outlet passageway 562 formed in a cover 564 which is superimposed over and connected to base assembly 554 in the manner shown in FIGS. 54 and 59. The heat-expandable means is held in position within opening 556 by a floor-like member 566 which forms a part of the base assembly 554 and preferably is insert molded to a base component 567 which also forms a part of the base assembly. Member 566 is typically constructed of a heat conductive metal such as aluminum or stainless steel which can be stamped into the required configuration and can function as an effective heat sink.

As in the previously described embodiments, the heat expandable means or mass 569 is covered by a sealing means comprising the previously described membrane 72 which is sealably connected to the peripheral portion of the base assembly by any suitable means such as thermal bonding. Overlaying membrane 72 and bonded to a cover 564 by any suitable means is the previously described distendable membrane 74 which, in cooperation with a generally concave shaped cavity 564a formed in cover 564 forms fluid reservoir 560 (FIG. 54).

As previously mentioned, the fill means of the latest embodiment is of a totally different character from that described in connection with the earlier embodiments of the invention. While as in the earlier described embodiments, the fill means functions to introduce fluids into reservoir 560, the fill means here comprises a novel vial fill subassembly, generally identified in the drawings by the numeral 570 as well as and a pierceable septum subassembly which is generally designated as 571. Both of these fill subassemblies communicate with a fluid inlet passageway 573 formed in cover 564.

Figure 60:
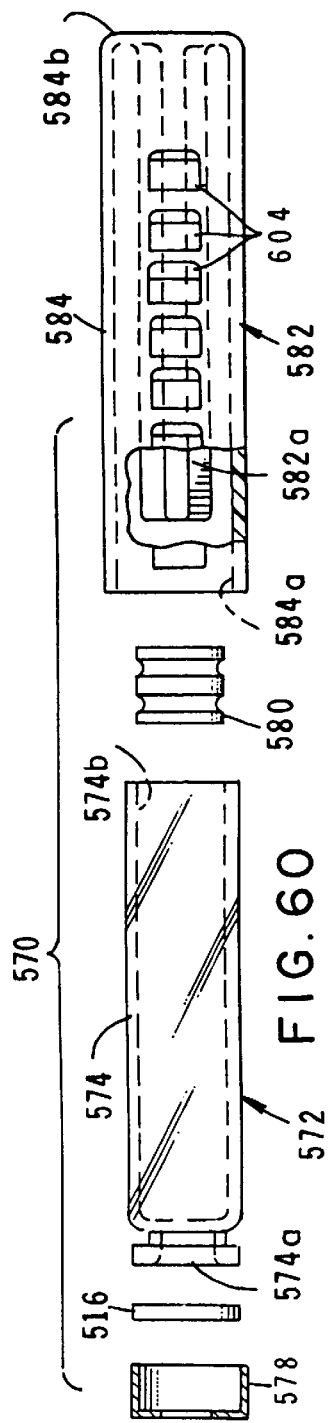
FIG. 60 is a top plan exploded view of the fill vial assembly of the invention.

Referring particularly to FIGS. 59 and 60, the vial fill subassembly 570 can be seen to comprise a container 572 which includes a hollow body portion 574, having first and second open ends 574a and 574b. First open end 574a is sealably closed by closure means, here provided in the form of a pierceable member 576 which is held in sealing engagement with body portion 574 by a clamping ring 578 (FIG. 60). A plunger 580 is telescopically movable within hollow body portion 574 from a first location proximate second open end 574b to a second location proximate first open end 574a. Body portion 574 can be constructed from various materials such as glass and plastic.

Figure 61:
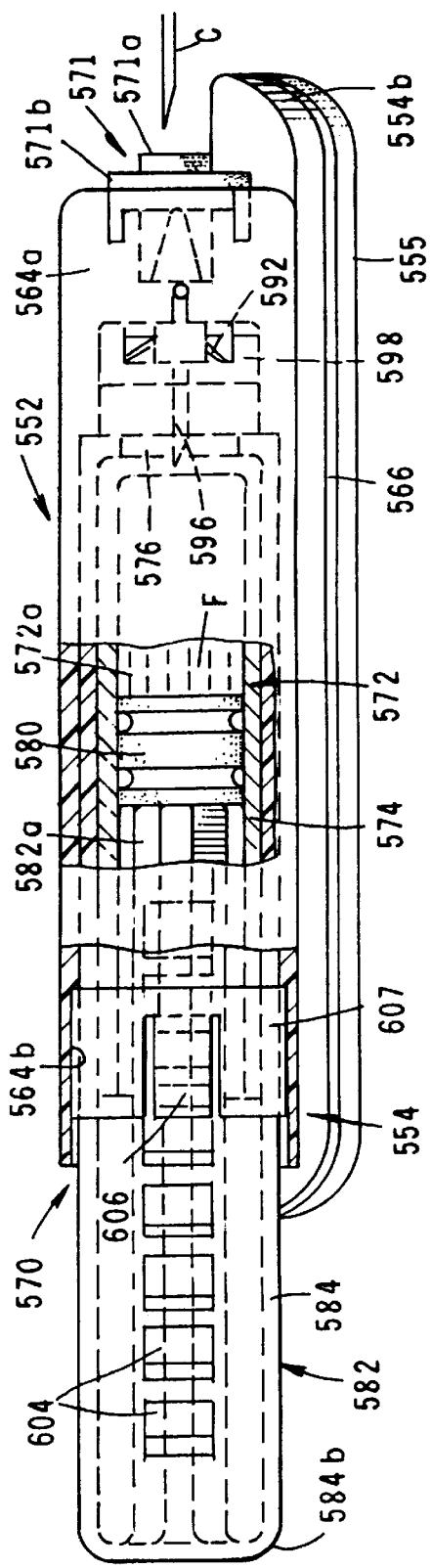
FIG. 61 is a side-elevational view of the fluid storage device of the invention shown in FIG. 53.
Figure 63:
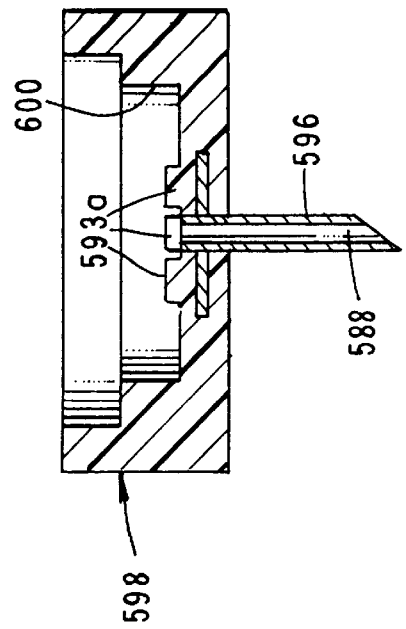
FIG. 63 is a cross-sectional view taken along lines 63—63 of FIG. 62.
Figure 62:
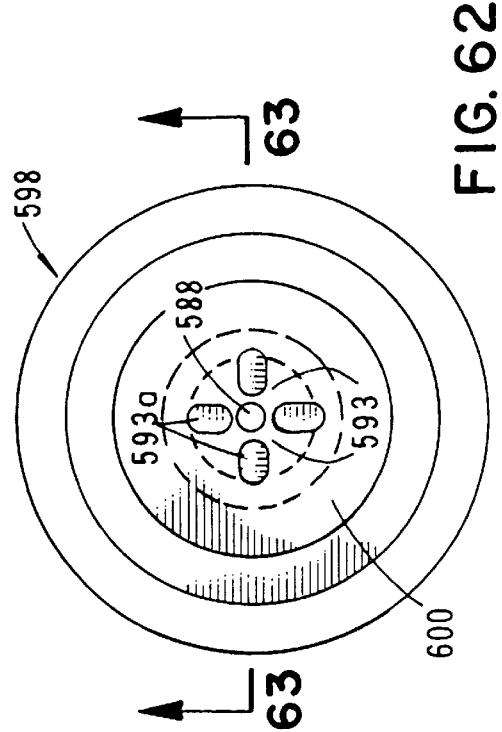
FIG. 62 is an enlarged top view of the cup-like fill needle portion of the fill means of the invention.

Also forming a part of the vial fill subassembly 570 of the invention, is an adapter component 582 which comprises a housing 584 having a first open end 584a and a second closed end 584b (FIG. 60). As indicated in FIGS. 53 and 61, container 572 is telescopically receivable within open end 584a of housing 584 so that the housing can be moved from the first extended position shown in FIG. 59 to a second, container encapsulation position wherein hollow body portion 574 is substantially encapsulated within the adapter component. Also forming a part of the adapter component 582 is pusher means shown here as a pusher member 582a (FIG. 61) which, in a manner presently to be described, functions to engage and controllably move plunger 580 longitudinally of body portion 574 from the first extended position to a second inserted position.

Figure 58:
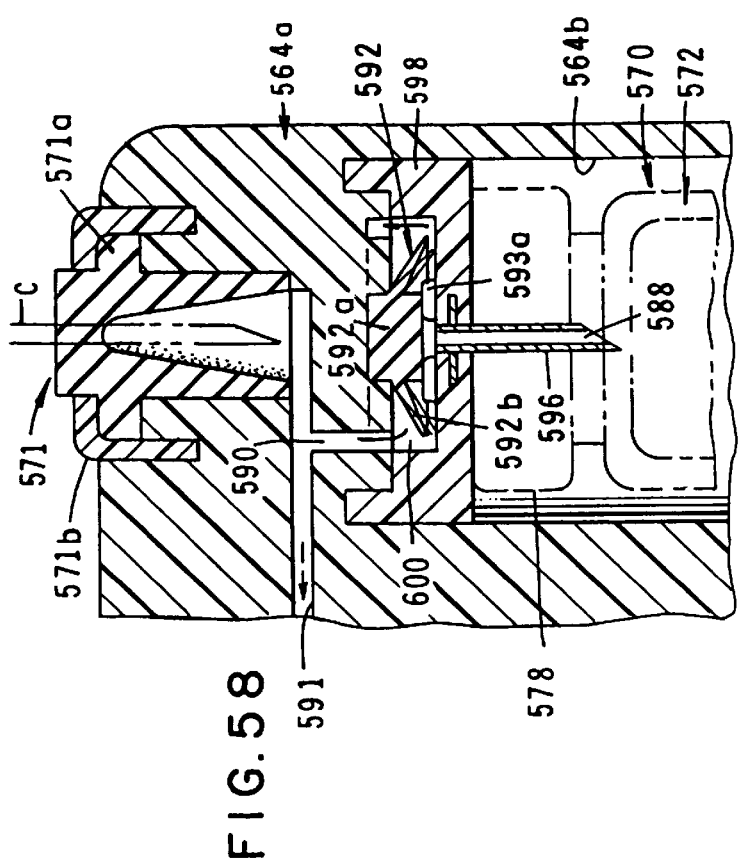
FIG. 58 is an enlarged fragmentary view of the upper right-hand portion of FIG. 53 showing the details of construction of a portion of the fill means of the invention.

Turning once again to FIGS. 53, 54, and 59, cover assembly 564 of the fluid storage device can be seen to include a side portion 564a having an elongated receiving chamber 564b which is adapted to receive the vial fill subassembly 570 of the invention. When the vial fill subassembly is in position within chamber 564b, the fluid chamber of the vial fill subassembly communicates with reservoir 560 via passageways 588, 590, 592, 594, and 573 (FIGS. 53 and 58). As shown in FIG. 58, passageways 590 and 592 are formed within cover portion 564a, while passageway 588 is formed within a cover mounted, piercing cannula 596 which is connected to and extends from a generally cup-shaped closure member 598. In the manner shown in the drawings, closure member 598 functions to close the inboard end of receiving chamber 564b. As best seen in FIG. 58, cannula passageway 588 communicates with a chamber 600 which, in turn, communicates with passageway 590 via valve means, shown here as an umbrella valve assembly 592. Valve assembly 592 includes a body portion 592a which is supported by closure member 598 and a resiliently deformable, umbrella-like member 592b which is disposed within chamber 600 and is movable in the manner indicated by the phantom lines in FIG. 58 from a valve closed position to a valve open position in response to fluid flowing through cannula 596, through passageways 593 formed between protuberances 593a formed on the inner wall of closure member 598, into chamber 600 and then toward passageway 590. However, it is to be noted that the construction of umbrella-like member 592b is such that it effectively blocks fluid flow in an opposite direction toward cannula 596.

In using the apparatus of the invention, with the fluid chamber 572a of container 572 filled with the desired beneficial agent "F" (FIG. 61), the vial fill subassembly 570 is telescopically inserted into receiving chamber 564b of cover 564 and is pushed inwardly with sufficient force to cause the piercing cannula 596 of closure member 598 to pierce sealing member 576 of the container assembly. Once a fluid flow path between the fluid chamber 572a of the container assembly and the fluid reservoir 560 of the fluid storage device is thus created, a continued inward movement of the adapter component over the container body 574 will cause pusher member 582a to engage and controllably move plunger 580 inwardly of hollow body 574. As plunger 580 moves inwardly of the container body, the fluid contained therewithin will flow toward end 574a, through passageway 588 of the piercing cannula 596 and then into chamber 600. The fluid flowing under pressure into chamber 600 will cause the umbrella valve 592 to open so that fluid can flow toward fluid reservoir 560 via passageways 590, 592, 594 and 573. Once reservoir 560 is filled, either with fluid introduced via the pierceable septum subassembly 571, or with fluid flowing from the vial fill subassembly 570 of the fill means or by a combination of both, the fluid will remain in the reservoir of the fluid storage device until time of use of the device.

Referring particularly to FIGS. 60 and 61, it is to be noted that adapter component 582 includes locking means for locking housing 584 within receiving chamber 564b of cover portion 564a after the vial fill subassembly has been mated with the fluid storage device. These locking means are here provided in the form of a series of longitudinally spaced locking teeth 604. These locking teeth are constructed so that as the adapter component is urged into chamber 564b the locking teeth will slide under a flexible locking tab 606, which is provided on a clip 607 that is connected to cover portion 564a at a location proximate the entrance of receiving chamber 564b (see also FIG. 55). However, once the adapter subassembly has reached the fully inserted position and the fluid contained within the container 574 has been transferred to reservoir 560, resilient locking tab 606 will return to its locking position and in so doing will engage teeth 604 in a manner to effectively prevent removal of the adapter component from chamber 546b. With this novel construction, once reservoir 560 has been filled with the fluid contained within container chamber 572a, the vial fill assembly cannot be removed from receiving chamber 564b and, therefore, cannot be reused thereby preventing system adulteration.

With reservoir 560 filled with the fluid to be infused into the patient and with the fluid storage device affixed to the patient, the body heat of the patient will cause the heat expandable means or mass 569 to controllably expand causing the fluid contained within the reservoir to flow outwardly thereof through outlet passageway 562. As before, when mass 569 expands, it will distend sealing membrane 72 and distendable membrane 74 in a direction toward inner wall 564a of cavity 560 (FIG. 54) causing a controlled flow of fluid from reservoir 560 through fluid outlet passageway 562 and into the infusion means 54 of the apparatus.

Figure 57:
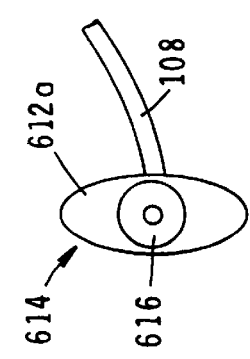
FIG. 57 is a cross-sectional view taken along lines 57—57 of FIG. 53.
Figure 58A:
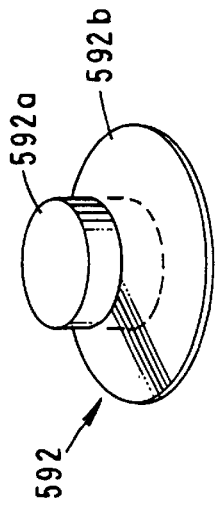
FIG. 58A is an enlarged, generally perspective view of the umbrella valve means of the invention.

As best seen in FIGS. 53, 56, and 57, the remotely located infusion means 54 is here interconnected with the fluid storage device by a novel quick connect and release means 572 of quite different construction from those previously described. This novel means, which includes the previously mentioned push button type capture and release assembly 553, enables quick interconnection of the administration line 108 of the infusion means with cover 564 so that the administration line is placed in fluid communication with outlet passageway 562 of reservoir 560. More particularly, as shown in FIG. 53, administration line 108 is here connected to a connector means which includes an oval body portion 614. Connected to or integrally formed with body portion 614 is a nipple 616 which is closely receivable within a socket 618 formed in cover 564 (FIGS. 53 and 54). Also formed in cover 564 is an oval aperture 620 which is adapted to receive a push button 622 of assembly 533. As best seen in FIG. 56, a pair of resiliently deformable, downwardly extending, spaced-apart arms 624 are attached to push button 622 by living hinges 624*a*. The extremities of arms 624 are adapted to slidably engage a wedge-like protuberance 626 formed on base assembly 554 so that when push button 622 is depressed, arms 624 will spread apart a distance sufficient to permit a shoulder 612*a* formed on connector 612 to pass between arms 624. As shown in FIG. 56A, when arms 624 are spread apart, shoulder 612*a*, which is also oval in cross section, will pass between the arms. When the arms resiliently spring back to their normal position, they will engage reduced diameter portion 614*a* of connector body 614 and thereby lock nipple 616 securely in position within socket 618. When it is desired to separate the infusion set 54 from the fluid storage device, a downward finger pressure exerted on push button 553 will once again spread arms 624 apart a distance sufficient to permit passage of shoulder 612*a* and removal of nipple 616 from socket 618.

After the fluid from reservoir 560 has been infused into the patient, the reservoir can, if desired, be refilled using the pierceable septum subassembly 571 of the fill means of the invention. As before, the elastomeric septum component 571*a* of the septum subassembly is held in position within cover 564 by a clamping ring 571*b* (FIG. 58). Once again, septum 571 is of a conventional non-coring elastomeric material construction and is penetrable by a cannula "C" of a syringe of conventional construction. A conventional syringe (not shown) can be used to introduce fluid to be dispensed into inlet passageway 592, into passageway 594, and thence into reservoir 560 via passageway 573.

Figure 64:
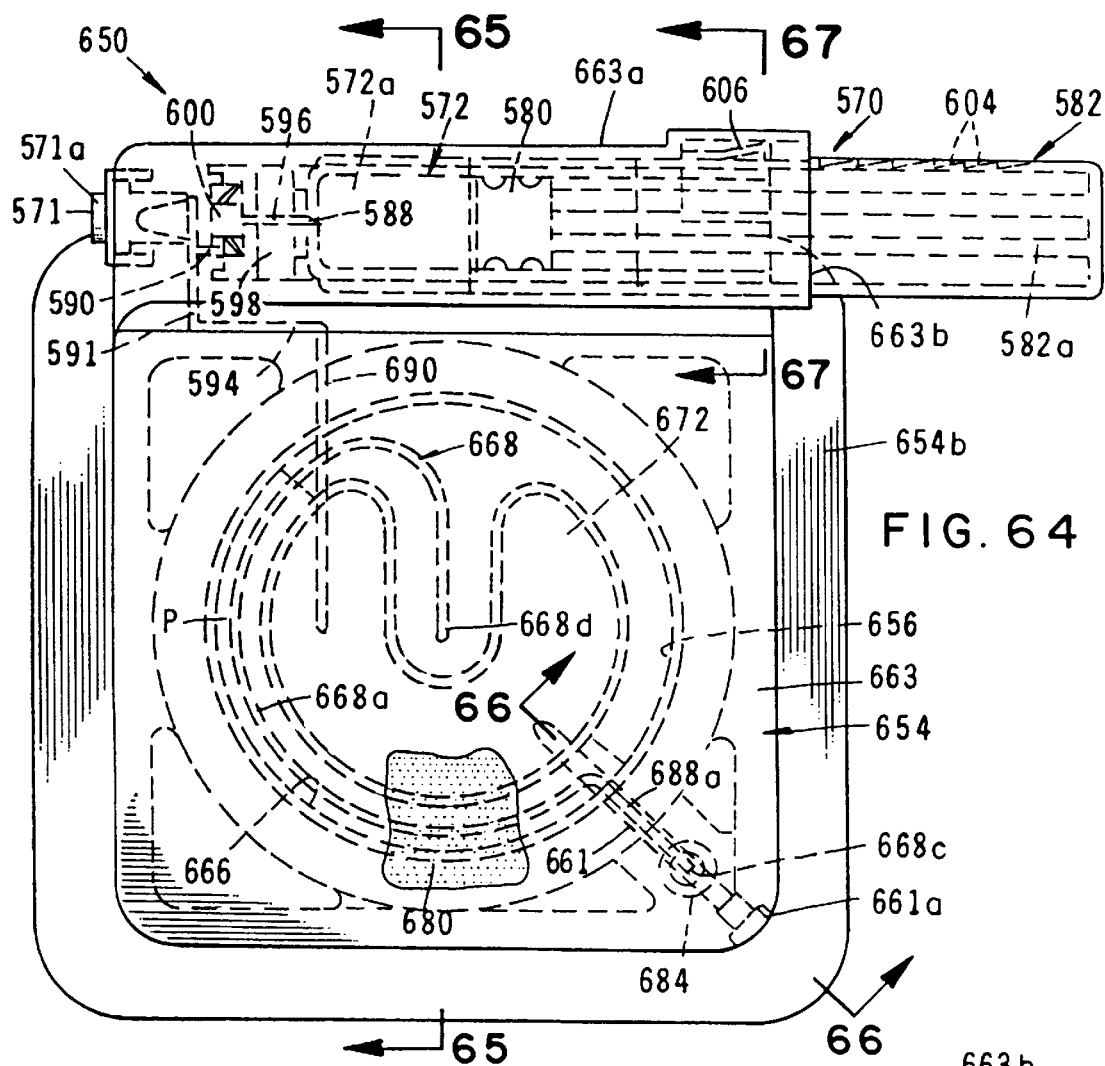
FIG. 64 is a top plan view of still another form of the fluid delivery apparatus of the invention which embodies a self-contained, dynamically mounted cannula.
Figure 65:
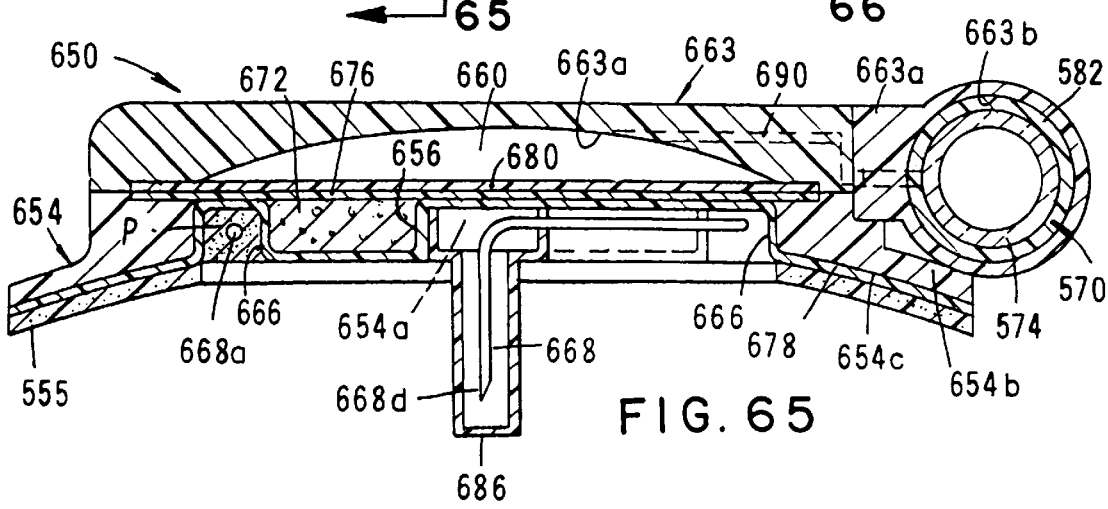
FIG. 65 is a cross-sectional view taken along lines 65—65 of FIG. 64.

Turning to FIGS. 64 through 69, still another form of the fluid delivery apparatus of the invention is there shown and generally designated by the numeral 650. This alternate embodiment of the invention is similar to that shown in FIGS. 53 through 63 and like numerals are used in FIGS. 64 through 69 to identify like components. As best seen in FIGS. 64 and 65, this latest apparatus also comprises a fluid storage device having a fluid reservoir which can be filled either by a septum assembly or by using a fluid container or vial assembly the character previously described. However, in this latest embodiment of the invention, the infusion means is provided as a part of the fluid storage device rather than comprising a remotely located infusion device such as the previously described infusion assemblage 54.

Like the embodiment of the invention shown in FIGS. 53 through 62, the fluid storage device here comprises a thin base assembly 654 having a central portion 654*a* and peripheral portion 654*b* circumscribing central portion 654*a*. As before, the base assembly is provided with a curved lower surface 654*c* which can be located proximate the patient so that the device can be taped or otherwise removably affixed to the patient, such as by using a foam adhesive tape 555.

Figure 66:
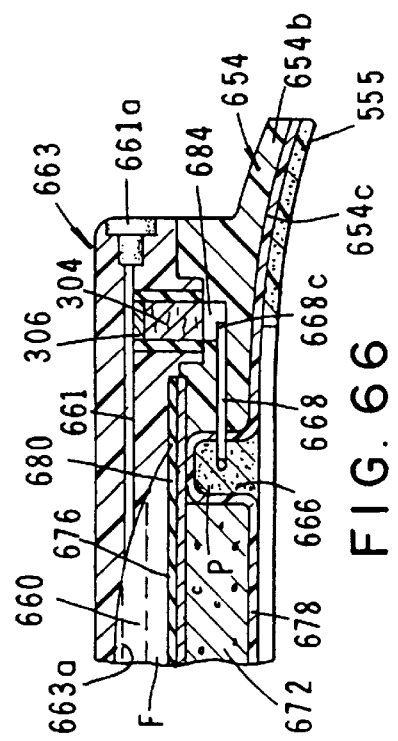
FIG. 66 is a cross-sectional view taken along lines 66—66 of FIG. 64.
Figure 68:
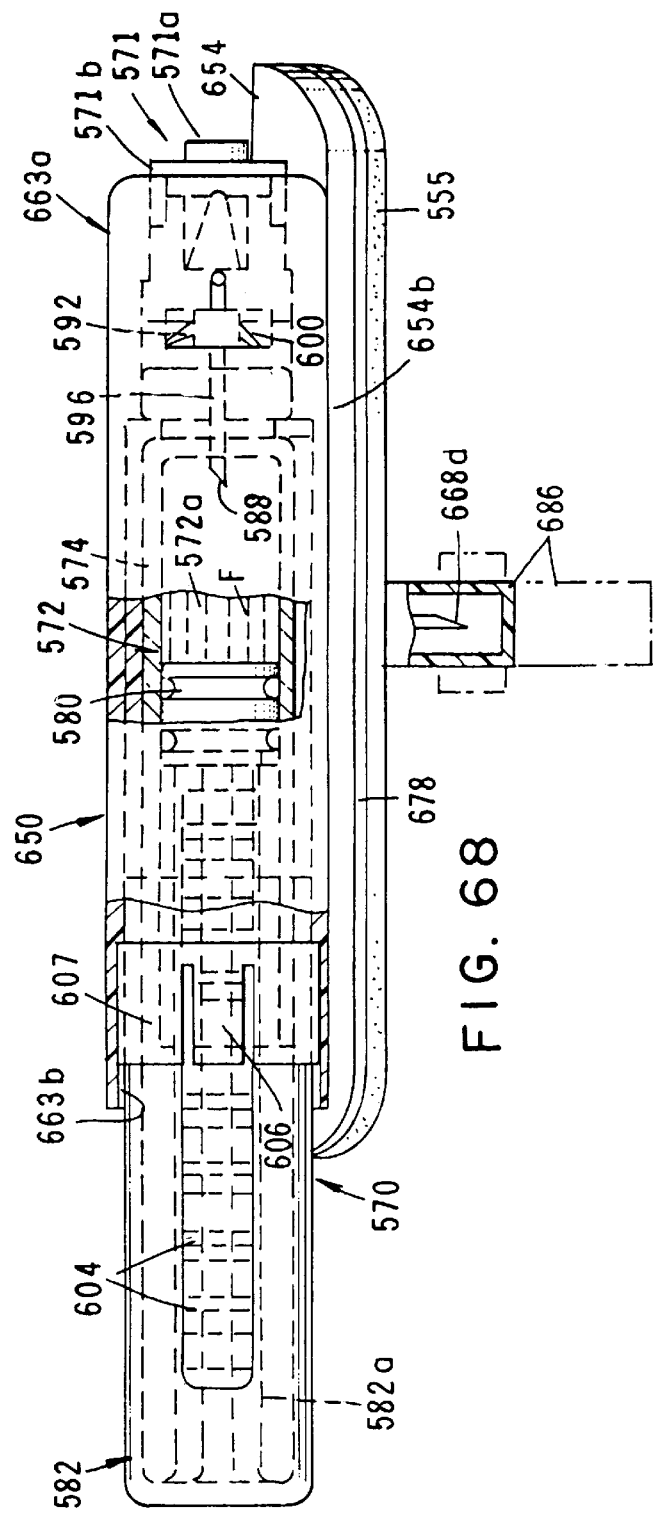
FIG. 68 is a side-elevational view of the apparatus of the invention shown in FIG. 64.

Formed within base assembly 654 is a generally U-shaped opening 656 (FIG. 69) which receives the heat-expandable means of the invention. Once again, this heat-expandable means upon being heated functions to controllably force the fluids contained within the sealed reservoir 660 of the device (FIG. 65) to flow outwardly through an outlet passageway 661 formed in a cover 663. As shown in FIG. 66 passageway 661 is closed at its outbound end by a small closure plug 661*a*. Also formed within base assembly 654 is a cannula receiving channel 666 (FIGS. 64 and 65) within which the body portion 668*a* of a novel spiral-like hollow cannula or capillary 668 is uniquely mounted in a manner presently to be described.

The previously mentioned heat expandable means is here provided in the form of a generally U-shaped heat expandable member 672 which is disposed within cavity 656 in the manner best illustrated in FIG. 69. Superimposed over cavity 656 and expandable member 672 is a sealing means which here comprises an elastomeric membrane 676 which is sealably connected to a strategically shaped floor. Floor 678, which is preferably provided in the form of a metal stamping, forms a part of the base assembly, and, as before, functions as an efficient heat sink to transfer heat to member 672. Overlaying membrane 676 is a distendable membrane 680 which, in cooperation with a generally concave shaped surface 663*a* formed on cover 663, forms the fluid reservoir 660. As in the earlier described embodiments, as expandable mass 672 is heated by the patient's body, it will controllably expand from its normal relaxed configuration to an expanded configuration. As member 672 expands into the expanded configuration, it will distend sealing membrane 676 as well as distendable membrane 680 in a direction toward concave inner wall 663*a* of a cover 663 and will cause the fluid contained within the fluid reservoir to flow outwardly toward the infusion means or cannula 668.

In addition to cannula 668, the infusion means also comprises flow control means for controlling fluid flow into cannula 668. This flow control means, which includes rate control means and cooperating filter means, is identical to that described in connection with the embodiment shown in FIGS. 25 through 28 and includes a porous rate control member 304 and a porous filter 306 (see also FIG. 27). As before, the flow control means is disposed between the outlet of the reservoir 660 and an inlet passageway 684 formed in the periphery of the base assembly 654. Cannula 668 includes an inlet end 668*c* which communicates with a passageway 684 (FIG. 66) and an outlet end 668*d* which comprises a needle-like segment that extends generally perpendicularly downward from base member 654 for subdermal infusion of medicinal fluids into the patient. For this purpose, outlet end 668*d* is provided with a sharp, pointed extremity. To maintain the outlet end in a sterile condition, a protective sheath 686 is provided. Sheath 686 surrounds the outwardly extending cannula segment and is removably affixed to floor 678 in the manner previously described and as shown in FIG. 65.

Turning once again to FIGS. 64 and 65, it is to be observed that part of the body portion 668*a* of spiral cannula 668 is uniquely supported within channel 666 of the base assembly by a cannula encapsulation means shown here as a standard potting compound "P". As in the earlier described embodiments of the invention, compound "P" rigidly supports the body portion of the cannula within channel 666 and dynamically supports the outer extremity of the cannula body so that the free end portion of the cannula can move three dimensionally within channel 666. With this construction, when the device is connected to the patient, normal movement by the patient will permit a portion of the cannula to move within a portion of channel 666 while the base and heat shield components of the base assembly remain completely stationary.

As previously mentioned, the fill means is substantially identical to the fill means of the embodiment shown in FIGS.

53 through 63 and comprises the vial fill subassembly 570 and the pierceable septum subassembly 571. Both of these fill subassemblies communicate with a fluid inlet passageway 690 formed in cover 663 (FIG. 64).

Figure 67:
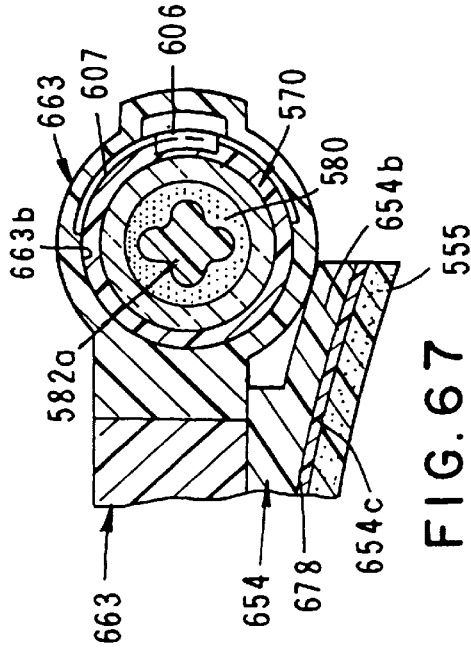
FIG. 67 is an enlarged, cross-sectional view taken along lines 67—67 of FIG. 64.

Referring particularly to FIGS. 65, 67, and 69, it can be seen that the vial fill subassembly 570 is identical to that previously described and includes a container component 572 and an adapter component 582. As before, container 572 is telescopically receivable within open end 584a of housing 584 of adapter component 582 so that the housing can be moved from a first extended position to a second, container encapsulation position.

As shown in FIGS. 64, 65 and 69, cover assembly 663 of the fluid storage device includes a side portion 663a having an elongated receiving chamber 663b which is adapted to receive the vial fill subassembly 570 of the invention. As before, when the vial fill subassembly is in position within receiving chamber 663b, the fluid chamber of the subassembly communicates with reservoir 660 via passageways 588, 590, 592, 594 and 690 (FIG. 64). As shown in FIG. 64, passageways 590 and 592 are formed within cover portion 663a, while passageway 588 is formed within the cover mounted piercing cannula 596 which is connected to and extends from a generally cup-shaped closure member 598 which functions to close the inboard end of receiving chamber 663b. As before, cannula passageway 588 communicates with a chamber 600 which, in turn, communicates with passageway 590 via valve means, or umbrella valve assembly 592 which is identical to that previously described.

During use of the apparatus of this latest form of the invention filling reservoir 660 can be accomplished either by using the vial fill subassembly or the septum fill subassembly. This filling step is basically the same as previously described in connection with the apparatus shown in FIGS. 53 through 63 and this reservoir filling step will not here be repeated.

Once the reservoir has been filled with the fluid "F" to be infused into the patient and the fluid storage device has been affixed to the patient by piercing the patient's skin and tissue with the downwardly depending cannula portion 668d, the body heat of the patient's body heat will cause the heat expandable means or mass 672 to controllably expand causing the fluid contained within the reservoir to flow outwardly thereof through outlet passageway 661. the fluid will then flow into the infusion means or cannula 668 via the flow control means which comprises filter 306 and rate control 304 (see FIG. 66).

After the fluid from reservoir 660 has been infused into the patient, the reservoir can, in the manner previously described, be refilled using the pierceable septum subassembly 571 of the fill means of the invention. Additionally, if desired fluid can at any time be removed from the reservoir using a suitable syringe and the pierceable septum subassembly 571.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

What is claimed is:

1. A device for use in infusing medicinal fluid into a patient at a controlled rate comprising:
   (a) a housing having a rigid surface and including a base defining a heat sink and a cover superimposed over said base;
   (b) distendable means for forming, in conjunction with said rigid surface of said housing, a fluid reservoir having an inlet and an outlet, said distendable means comprising at least one distendable membrane at least a portion of which is movable within said housing from a first position to a second position;
   (c) heat expandable means disposed within said housing between said heat sink and said cover and in proximity to said distendable membrane, said heat expandable means comprising a semi-solid, which, upon being heated, will act upon said distendable membrane to move said membrane toward said second position to cause fluid within said reservoir to flow outwardly of said outlet of said reservoir; and
   (d) infusion means in communication with said outlet of said reservoir for infusing fluid from said fluid reservoir into the patient.

2. A device as defined in claim 1 in which said infusion means comprises a hollow cannula connected to said base and extending therefrom.

3. A device as defined in claim 1 further including flow control means carried by said housing for controlling fluid flow from said fluid reservoir toward said infusion means.

4. A device as defined in claim 1 in which said heat expandable means is carried by said base and in which said distendable membrane overlays said heat expandable means and is connected to said base.

5. A device as defined in claim 4 further including a second distendable membrane overlaying said first distendable membrane, said second distendable membrane being connected to a selected one of said base and said cover.

6. A device for use in infusing medicinal fluid into a patient at a controlled rate comprising:
   (a) a housing having surface and a fluid flow channel, said housing comprising a base and a cover superimposed over said base;
   (b) distendable means for forming, in conjunction with said surface of said housing, a fluid reservoir having an outlet, said distendable means comprising at least one distendable membrane disposed between said cover and said base, at least a portion of said membrane being movable within said housing from a first position to a second position;
   (c) heat expandable means disposed within said housing in proximity with said distendable membrane, said heat expandable means, upon being heated, acting upon said distendable membrane to move said membrane toward said second position to cause fluid within said reservoir to flow outwardly of said outlet of said reservoir;
   (d) infusion means in communication with said outlet of said reservoir for infusing fluid from said fluid reservoir into the patient; and
   (e) flow indicator means disposed within said reservoir for indicating fluid flow from said reservoir.

7. A device for use in infusing medicinal fluid into a patient at a controlled rate comprising:
   (a) a housing having a rigid surface;
   (b) distendable means for forming, in conjunction with said rigid surface of said housing, a fluid reservoir having an inlet and an outlet, said distendable means comprising at least one distendable membrane at least a portion of which is movable within said housing from a first position to a second position;
   (c) a heat expandable gel disposed within said housing in proximity to said distendable membrane, said heat expandable gel, upon being heated, acting upon said distendable membrane to move said membrane toward said second position to cause fluid within said reservoir to flow outwardly of said outlet of said reservoir; and (d) fill means in communication with said inlet of said fluid reservoir for filling said reservoir with fluid, said fill means comprising a liquid container interconnectable with said housing; and (e) infusion means in communication with said outlet of said reservoir for infusing fluid from said fluid reservoir into the patient.

8. A device as defined in claim 7 in which said housing includes a receiving chamber for telescopically receiving said liquid container.

9. A device as defined in claim 8 in which said receiving chamber is provided with a piercing cannula in communication with said reservoir and in which said liquid container includes a sealing membrane pierceable by said piercing cannula.

10. A device for use in infusing medicinal fluid into a patient at a controlled rate comprising:

(a) a housing having a rigid surface and a socket (b) distendable means for forming, in conjunction with said rigid surface of said housing, a fluid reservoir having an inlet and an outlet, said distendable means comprising at least one distendable membrane at least a portion of which is movable within said housing from a first position to a second position;

(c) heat expandable means disposed within said housing between said rigid surface and said distendable membrane, said heat expandable means comprising a semi-solid, which, upon being heated, will act upon said distendable membrane to move said membrane toward said second position to cause fluid within said reservoir to flow outwardly of said outlet of said reservoir;

(d) infusion means in communication with said outlet of said reservoir for infusing fluid from said fluid reservoir into the patient, said infusion means comprising an elongated fill tube and a subcutaneous infusion device connected to and spaced apart from said housing for infusing fluid from said reservoir into said patient; and (e) means for interconnecting said infusion means with said housing, said means comprising a quick connect mechanism for quickly interconnecting said fill tube with said housing, said quick connect mechanism comprising:

(i) a hub at least partially receivable in said socket in said housing; and (ii) at least one yieldably deformable arm connected to said hub for releasably gripping said housing.

11. A device for use in infusing medicinal fluid into a patient at a controlled rate comprising:

(a) a housing having a rigid surface and a socket (b) distendable means for forming, in conjunction with said rigid surface of said housing, a fluid reservoir having an inlet and an outlet, said distendable means comprising at least one distendable membrane at least a portion of which is movable within said housing from a first position to a second position;

(c) heat expandable means disposed within said housing between said rigid surface and said distendable membrane, said heat expandable means comprising a semi-solid, which, upon being heated, will act upon said distendable membrane to move said membrane toward said second position to cause fluid within said reservoir to flow outwardly of said outlet of said reservoir;

(d) infusion means in communication with said outlet of said reservoir for infusing fluid from said fluid reservoir into the patient, said infusion means comprising an elongated fill tube and a subcutaneous infusion device connected to and spaced apart from said housing for infusing fluid from said reservoir into said patient; and (e) means for interconnecting said infusion means with said housing, said means comprising a quick connect mechanism for quickly interconnecting said fill tube with said housing, said quick connect mechanism comprising:

(ii) a hub at least partially receivable in said socket in said housing; and (ii) release means for releasably locking said hub in position within said socket.

12. A device as defined in claim 11 in which said release means comprises a push button assembly connected to said cover.

13. A device for use in infusing medicinal fluid into a patient at a controlled rate comprising:

(a) a housing having a rigid surface;

(b) distendable means for forming, in conjunction with said rigid surface of said housing, a fluid reservoir having an inlet and an outlet, said distendable means comprising at least one distendable membrane at least a portion of which is movable within said housing from a first position to a second position;

(c) heat expandable means disposed within said housing between said rigid surface and said distendable membrane, said heat expandable means comprising a plurality of polymers disposed in a laminated assemblage, each of said polymers, upon being heated, acting upon said distendable membrane to move said membrane toward said second position to cause fluid within said reservoir to flow outwardly of said outlet of said reservoir; and (d) infusion means in communication with said outlet of said reservoir for infusing fluid from said fluid reservoir into the patient.

14. A device as defined in claim 13 in which said heat expandable means comprises a blend of said polymers which expand at different rates as a function of time.

15. A device as defined in claim 13 in which said plurality of polymers comprise at least two phase transition gel laminates of different thickness.

16. A device for use in infusing medicinal fluid into a patient at a controlled rate comprising:

(a) a housing having a rigid surface;

(b) distendable means for forming, in conjunction with said rigid surface of said housing, a fluid reservoir having an inlet and an outlet, said distendable means comprising at least one distendable membrane at least a portion of which is movable within said housing from a first position to a second position;

(c) a heat-expandable, three-dimensional gel network disposed within said housing in proximity to said distendable membrane, said heat expandable gel, upon being heated, changes in volume so as to act upon said distendable membrane to move said membrane toward said second position to cause fluid within said reservoir to flow outwardly of said outlet of said reservoir;

(d) fill means in communication with said inlet of said fluid reservoir for filling said reservoir with fluid;

(e) infusion means in communication with said outlet of said reservoir for infusing fluid from said fluid reservoir into the patient; and (f) flow control means disposed between said outlet of said reservoir and said infusion means for controlling fluid flow toward said infusion means.

17. A device as defined in claim 16 in which said flow control means comprises a filter and a flow rate control means.

18. A device as defined in claim 16 in which said flow control means comprises a capillary having a fixed length and diameter mounted between said reservoir and said infusion means.

19. A device as defined in claim 16 in which flow control means comprises a micro-porous membrane mounted within said housing.

20. A device as defined in claim 16 in which said flow control means comprises a permeable membrane mounted within said housing.

21. A device as defined in claim 16 in which said flow control means comprises a membrane having an aperture of a fixed diameter.

* * * * *